(12) United States Patent
Hultgren et al.

(10) Patent No.: US 10,449,242 B2
(45) Date of Patent: Oct. 22, 2019

(54) COMPOSITIONS AND METHODS FOR THE TREATMENT AND PREVENTION OF EBP PILUS-RELATED DISEASES

(71) Applicant: Washington University, St. Louis, MO (US)

(72) Inventors: Scott J. Hultgren, St. Louis, MO (US); Michael G. Caparon, St. Louis, MO (US); Jerome Pinkner, St. Louis, MO (US); Ana L. Flores-Mireles, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 15/811,250

(22) Filed: Nov. 13, 2017

(65) Prior Publication Data
US 2018/0055923 A1 Mar. 1, 2018

Related U.S. Application Data

(62) Division of application No. 14/851,805, filed on Sep. 11, 2015, now Pat. No. 9,839,682.

(60) Provisional application No. 62/049,703, filed on Sep. 12, 2014.

(51) Int. Cl.
*A61K 39/09* (2006.01)
*C07K 16/12* (2006.01)
*A61K 39/00* (2006.01)

(52) U.S. Cl.
CPC .......... *A61K 39/09* (2013.01); *C07K 16/1267* (2013.01); *A61K 2039/505* (2013.01); *A61K 2039/55566* (2013.01)

(58) Field of Classification Search
CPC ..................................................... A61K 39/09
See application file for complete search history.

(56) References Cited

U.S. PATENT DOCUMENTS

2004/0101919 A1  5/2004 Hook et al.

OTHER PUBLICATIONS

Ackland, "Prevalence, Detection, Evaluation and Management of Chronic Kidney Disease," BMJ, 2014, pp. 1-16, vol. 348.
Altschul et al., "Basic Local Alignment Search Tool," J. Mol. Biol., 1990, pp. 403-410, vol. 215.
Arias et al., "Emergence and management of drug-resistant enterococcal infections," Expert Rev. Anti Infect. Ther., 2008, pp. 637-655, vol. 6, No. 5.
Arias et al., "The rise of the Enterococcus: beyond vancomycin resistance," Nat Rev Microbiol., 2012, pp. 266-278, vol. 10, No. 4.
Budzik et al., "Pili prove pertinent to enterococcal endocarditis," The Journal of Clinical Investigation, 2006, pp. 2582-2584, vol. 116, No. 10.
Cardoso et al., "Additional risk factors for infection by multidrug-resistant pathogens in healthcare-associated Infection: a large cohort study," BMC Infectious Diseases, 2012, pp. 1-9, vol. 12, No. 375.
Currie et al., "Proteinuria and its relation to cardiovascular disease," International Journal of Nephrology and Renovascular Disease, 2014, pp. 13-24, vol. 7.
Cusumano et al., "Bacterial adhesion—A source of alternate antibiotic targets," IDrugs, 2009, pp. 699-705, vol. 12.
Davalos et al., "Fibrinogen as a key regulator of inflammation in disease," Semin Immunopathol., 2012, pp. 43-62, vol. 34.
Delnay et al., "Bladder Histological Changes Associated with Chronic Indwelling Urinary Catheter," The Journal of Urology, 1999, pp. 1106-1109, vol. 161.
Dunny et al., "Induced cell aggregation and mating in *Streptococcus faecalis*: Evidence for a bacterial sex pheromone," Proc. Natl. Acad. Sci. USA, 1978, pp. 3479-3483, vol. 75, No. 7.
Gao et al., "*Enterococcus faecalis* mjB is Required for Pilin Gene Expression and Biofilm Formation," Journal of Bacteriology, 2010, pp. 5489-5498, vol. 192, No. 20.
Guiton et al., "*Enterococcus faecalis* Overcomes Foreign Body-Mediated Inflammation to Establish Urinary Tract Infections," Infection and Immunity, 2013, pp. 329-339, vol. 81, No. 1.
Guiton et al., "Contribution of Autolysin and Sortase a during *Enterococcus faecalis*, DNA-Dependent Biofilm Development," Infection and Immunity, 2009, pp. 3626-3638, vol. 77, No. 9.
Guiton et al., "Enterococcal Biofilm Formation and Virulence in an Optimized Murine Model of Foreign Body-Associated Urinary Tract Infections," Infection and Immunity, 2010, pp. 4166-4175, vol. 78, No. 10.
Hannan et al., "Early Severe Inflammatory Responses to Uropathogenic *E. coli* Predispose to Chronic and Recurrent Urinary Tract Infection," PLoS Pathogens, 2010, e1001042, pp. 1-19, vol. 6, Issue 8.
Hidron et al., "Antimicrobial-Resistant Pathogens Associated with Healthcare-Associated Infections: Annual Summary of Data Reported to the National Healthcare Safety Network at the Centers for Disease Control and Prevention, 2006-2007," Infection Control and Hospital Epidemiology, 2008, pp. 996-1011, vol. 29, No. 11.
Hung et al., "A murine model of urinary tract infection," Nat Protoc., 2009, pp. 1230-1243, vol. 4, No. 8.
Jennewein et al., "Novel Aspects of Fibrin(ogen) Fragments during Inflammation," Mol Med, 2011, pp. 568-573, vol. 17, No. 5-6.
Kelley et al., "Protein structure prediction on the Web: a case study using the Phyre server," Nature Protocols, 2009, pp. 363-371, vol. 4, No. 3.
Khudaier et al., "Epidemiology and molecular characterization of vancomycin resistant Enterococci isolates in India," Scandinavian Journal of Infectious Diseases, 2007, pp. 662-670, vol. 39, No. 8.
Kurosaka et al., "A Non-Surgical Rat Model of Foreign Body-Associated Urinary Tract Infection with Pseudomonas aeruginosa;" Microbiol. Immunol., 2001, pp. 9-15, vol. 45, No. 1.

(Continued)

*Primary Examiner* — Albert M Navarro
(74) *Attorney, Agent, or Firm* — Polsinelli PC

(57) ABSTRACT

The present invention relates to compositions comprising EbpA and methods of use thereof. Specifically, methods useful in the treatment and prevention of EbpA-associated infections.

12 Claims, 37 Drawing Sheets
(23 of 37 Drawing Sheet(s) Filed in Color)
Specification includes a Sequence Listing.

(56) References Cited

OTHER PUBLICATIONS

Langermann et al., "Prevention of Mucosal *Escherichia coli* Infection by FimH-Adhesin-Based Systemic Vaccination," Sci., 1997, pp. 607-611, vol. 276.
Maki et al., "Engineering Out the Risk for Infection with Urinary Catheters," Emerging Infectious Diseases, 2001, pp. 342-347, vol. 7, No. 2.
Molinos et al., "Detection of ebp (endocarditis- and biofilm-associated pilus) genes in enterococcal isolates from clinical and non-clinical origin," International Journal of Food Microbiology, 2008, pp. 123-126, vol. 126.
Mora et al., "Group a *Streptococcus* produce pilus-like structures containing protective antigens and Lancefield T antigens," PNAS, 2005, pp. 15641-15646, vol. 102, No. 43.
Mosesson, "Fibrinogen and fibrin structure and functions," Journal of Thrombosis and Haemostasis, 2005, pp. 1894-1904, vol. 3.
Mount, "Using the Basic Local Alignment Search Tool (BLAST)," Cold Spring Harbor Protocols, 2007, pp. 1-5.
Murcia et al., "Functional and computational studies of the ligand-associated metal binding site of $\beta 3$ integrins," Proteins, 2008, pp. 1779-1791, vol. 71, No. 4.
Nallapareddy et al., "Endocarditis and biofilm-associated pili of Enterococcus faecalis," The Journal of Clinical Investigation, 2006, pp. 2799-2807, vol. 116, No. 10.
Nallapareddy et al., "Relative Contibutions of Ebp Pili and the Collagen Adhesin Ace to Host Extracellular Matrix Protein Adherence and Experimental Urinary Tract Infection by Enterococcus faecalis OG1RF," Infection and Immunity, 2011, pp. 2901-2910, vol. 79, No. 7.
Nicolle, "The Chronic Indwelling Catheter and Urinary Infection in Long-Term-Care Facility Residents," Infection Control and Hospital Epidemiology, 2001, pp. 316-321, vol. 22, No. 5.
Nielsen et al., "The Metal Ion-Dependent Adhesion Site Motif of the Enterococcus faecalis EbpA Pilin Mediates Pilus Function in Catheter-Associated Urinary Tract Infection," MBio, 2012, e00177-12, pp. 1-10, vol. 3, Issue 4.
Nielsen et al., "Pilin and Sortase Residues Critical for Endocarditis- and Biofilm-Associated Pilus Biogenesis in Enterococcus faecalis," Journal of Bacteriology, 2013, pp. 4484-4495, vol. 195, No. 19.
Paganelli et al., "Optimizing future treatment of enterococcal infections: attacking the biofilm?", Trends in Microbiology, 2012, pp. 40-49, vol. 20, No. 1.
Parker et al., "Nursing Interventions to Reduce the Risk of Catheter-Associated Urinary Tract Infection, Part 1: Catheter Selection," J Wound Ostomy Continence Nurs., 2009, pp. 23-34, vol. 36, No. 1.
Parker et al., "Catheter-Associated Urinary Tract Infections: Fact Sheet," J Wound Ostomy Continence Nurs., 2009, pp. 156-159, vol. 36, No. 2.
Pinkston et al., "Targeting Pili in Enterococcal Pathogenesis," Infection and Immunity, 2014, pp. 1540-1547, vol. 82, No. 4.
Sarwar et al., "Markers of inflammation and risk of coronary heart disease," Disease Markers, 2009, pp. 217-225, vol. 26.
Sillanpaa et al., "Contribution of Individual Ebp Pilus Subunits of Enterococcus faecalis OG1RF to Pilus Biogenesis, Biofilm Formation and Urinary Tract Infection," PLoS ONE, 2013, e68813, pp. 1-20, vol. 8, Issue 7.
Singh et al. "Importance of the Endocarditis and Biofilm-associated Pilus (ebp) Locus in the Pathogenesis of Enterococcus faecalis Ascending Urinary Tract Infection," J Infect Dis., 2007, pp. 1671-1677, vol. 195, No. 11.
Snyder et al., "Detection and Evaluation of Chronic Kidney Disease," American Family Physician, 2005, pp. 1723-1732, vol. 72, No. 9.
Vaidyanathan et al., "Prevention of pressure sore caused by indwelling urinary catheters," Spinal Cord, 2002, 1 page, vol. 40:489.
Vaidyanathan et al., "Problems in early diagnosis of bladder cancer in a spinal cord injury patient: Report of a case of simultaneous production of granulocyte colony stimulating factor and parathyroid hormone-related protein by squamous cell carcinoma of urinary bladder," BMC Urology, 2002, pp. 1-10, vol. 2, No. 8.
van Opijnen et al., "A tine scale phenotype-genotype virulence map of a bacterial pathogen," Genome Research, 2012, pp. 2541-2551, vol. 22.
Webb et al., "Plasticizers Increase Adhesion of the Deteriogenic Fungus Aureobasidium pullulans to Polyvinyl chloride," Applied and Environmental Microbiology, 1999, pp. 3575-3581, vol. 65, No. 8.
Willson et al., "Nursing Interventions to Reduce the Risk of Catheter-Associated Urinary Tract Infection, Part 2: Staff Education, Monitoring, and Care Techniques," J Wound Ostomy Continence Nurs., 2009, pp. 137-154, vol. 36, No. 2.
Zandbergen et al., "PPARα in atherosclerosis and inflammation," Biochim Biophys Acta., 2007, pp. 972-982, vol. 1771, No. 8.
Office Action dated Dec. 13, 2016 from related U.S. Appl. No. 14/851,805; 10 pgs.

Treatment

COMPOSITIONS AND METHODS FOR THE TREATMENT AND PREVENTION OF EBP PILUS-RELATED DISEASES

CROSS REFERENCE TO RELATED APPLICATIONS

This application claims the priority of U.S. provisional application No. 62/049,703, filed Sep. 12, 2014, and is a divisional of application Ser. No. 14/851,805, filed Sep. 11, 2015, each of which are hereby incorporated by reference in their entirety.

GOVERNMENTAL RIGHTS

This invention was made with government support under AI1108749, DK051406, and DK064540 awarded by the National Institutes of Health. The government has certain rights in the invention.

FIELD OF THE INVENTION

The present invention relates to compositions comprising EbpA and methods of use thereof. Specifically, methods useful in the treatment and prevention of EbpA-associated infections.

BACKGROUND OF THE INVENTION

Catheter-associated urinary tract infections (CAUTIs) are the most common cause of hospital-acquired infections with the incidence of conversion from sterile urine to bacteriuria occurring at the rate of 3 to 10% per day. Furthermore, 3% of all patients with chronic indwelling urinary catheters will develop bacteremia within 30 days, and virtually all patients will develop an infection once the catheter has been in place >30 days. Drug resistance has become a critical concern for treatment of CAUTIs, particularly for infections caused by Gram-positive bacteria in the genus Enterococcus, which account for 15% of all CAUTIs. Because of their tolerance to heat, aseptic solutions, and intrinsic antibiotic resistance, enterococci have been difficult to control in the hospital environment. Of concern, their intrinsic resistances have been augmented by the emergence of strains resistant to nearly all antibiotics commonly used in treatment, including vancomycin. Treatment now has few options and often requires frequent removal and replacement of the catheter. Thus, the development of alternative therapies and prophylactic strategies is required. As such, there is a need in the art for a new strategy for the treatment and prevention of catheter-associated urinary tract infections.

SUMMARY OF THE INVENTION

In an aspect, the present invention encompasses a vaccine composition. The vaccine composition comprises the N-terminal domain of EbpA.

In another aspect, the present invention encompasses a method of treating an EbpA-associated infection in a subject. The method comprises administering an effective amount of a vaccine composition comprising EbpA NTD, administering an effective amount of a composition comprising an anti-EbpA NTD antibody, or a combination thereof.

In still another aspect, the present invention encompasses a method for detecting an EbpA-associated infection. The method comprises obtaining a biological sample from a subject; measuring the amount of EbpA NTD in the sample using an anti-EbpA NTD antibody; comparing the amount of EbpA NTD in the sample to a reference value; and classifying the subject as having a high or low amount of EbpA NTD based on the amount of EbpA NTD measured in the sample.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) *E. faecalis* strains with deletions (Δ) of Ebp pilus subunits and Gram-positive bacterial assembly proteins were evaluated for biofilm formation in a standard in vitro polyvinyl chloride coverslip assay after 48 hours by staining with crystal violet. The EbpA MIDAS motif mutant was designated as EbpA$^{AWAGA\ (SEQ\ ID\ NO:1)}$. (FIG. 1B and FIG. 1C) Adherence of the indicated whole bacterial strains to (FIG. 1B) collagen I (Col I)—coated or (FIG. 1C) fibrinogen (Fg)—coated surfaces was assessed by ELISA using a rabbit anti-group D streptococcal antibody. (FIG. 1D) EbpA domain structure, as predicted by PHYRE2 software (47). S, signal sequence; CWSS, C-terminal cell wall sorting signal; vWA, von Willebrand factor A domain containing a MIDAS motif. Shown below the figure are the regions included in the indicated EbpA subdomain proteins. (FIG. 1E) ELISA assay to quantitate binding of the indicated purified proteins to immobilized fibrinogen using a mouse anti-EbpA$^{Full}$ antisera. All assays used human collagen I and fibrinogen. Data represent means ±SEM derived from at least three independent experiments with differences between mean values evaluated for significance using a paired t test: *P<0.05; P<0.005; *P<0.0005; ns (differences not significant), P>0.05.

(FIG. 3A) Mice were infected with *E. faecalis* OG1 RF (wild type) (representative images). (FIG. 3B) Mice were infected with *E. faecalis* OG1 RF (wild type) or by mutants that did not express pili (ΔEbpABCΔSrtC) or that expressed EbpA with a defective MIDAS motif (EbpA$^{AWAGA}$ $^{(SEQ\ ID\ NO:\ 1)}$) Bacterial EbpA colocalization with fibrinogen was compared to that for mock-infected mice (PBS control) (representative images). The white broken line separates the bladder lumen (L) from the urothelium surface (U).

(FIG. 4A) Cultures were inoculated to an initial density of ~5×10$^5$ CFU/ml. (FIG. 4B, FIG. 4C, FIG. 4D) Growth curves in urine over a range of concentrations of fibrinogen (FIG. 4B), BSA (FIG. 4C), or CA (FIG. 4D). (FIG. 4E) Examination of uninoculated fibrinogen-supplemented urine by negative staining with 1% uranyl acetate and electron microscopy revealed lattice-like structures that were consumed after 24 hours of culture with *E. faecalis*. Scale bar, 500 nm. (FIG. 4F) Biofilm formation in vitro on 1-cm silicon catheters in urine supplemented with fibrinogen and BSA. Scale bar, 500 nm. (FIG. 4G, FIG. 4H, FIG. 4I) Biofilm formation in a standard 96-well polystyrene plate assay comparing wild-type (OG1 RF) and MIDAS mutant (EbpA$^{AWAGA}$ $^{(SEQ\ ID\ NO:1)}$) strains in fibrinogen-supplemented (FIG. 4G, FIG. 4H) or either BSA- or CA-supplemented urine (FIG. 4I). Biofilm formation in a standard growth medium (TSGB) was included for comparison. Values represent means ±SEM derived from at least three independent experiments with differences between mean values evaluated for significance using a paired t test: *P<0.05; P<0.005; *P<0.0005; ns, P>0.05. Human urine was pooled from three healthy female donors, clarified by centrifugation, and adjusted to pH 6.5 before use.

(FIG. 5C) The presence and distribution of bacteria and fibrinogen were assessed in catheters recovered from three mice taken randomly in the indicated treatment groups by immunofluorescence staining using antibody staining to detect fibrinogen (anti-Fg) and *E. faecalis* (anti-group D). (FIG. 5F) Ability of sera recovered from immunized mice to block binding of purified EbpA proteins to a fibrinogen-coated surface was evaluated by ELISA. Mouse anti-EbpA$^{Full}$ was used to detect all species of EbpA. Rabbit anti-EbpA$^{CTD}$ was used as a negative control. Rabbit anti-fibrinogen was used to block fibrinogen before adding the proteins. Values represent means ±SEM. Mann-Whitney U test was used for mouse experiments and paired t test for binding assays. P<0.05 was considered statistically significant. *P<0.05; P<0.005; *P<0.0005; ns, values were not statistically different. The horizontal bar represents the median value. The horizontal broken line represents the limit of detection of viable bacteria. Animals that lost the catheter were not included in this work.

(FIG. 6A) *E. faecalis* biofilm on catheters under urine condition by staining with crystal violet. Data presented represent the mean ±SEM derived from at least 3 independent experiments with differences between mean values evaluated for significance using a paired t-test: *, P<0.05; , P<0.005; *, P<0.0005; ns, P>0.05. TSGB standard medium was used as a positive control for biofilm formation. (FIG. 6B) *E. faecalis* was grown in the urine supplemented or not with glucose, TSBG and BHI media were used as positive growth control.

(FIG. 7A) Purified Ebp subunits and EbpA domains; and (FIG. 7B) Purified of EbpA$^{Full}$ and EbpA$^{AWAGA}$ $^{(SEQ\ ID\ NO:1)}$. Proteins were loaded into 4-20% SDS-PAGE gel and visualized by Coomassie staining.

(FIG. 10A and FIG. 10B) Sera collected over time (weeks of immunization) were pooled from each group of mice immunized with the indicated dose of EbpA. Pooled sera was diluted 1:100 upon collection and then was subjected to additional dilution as indicated at the right of the Figure. Aliquots of each dilution were then reacted with purified EbpA in an ELISA assay. Shown is the A540 value obtained following 5 min of reaction. (FIG. 10C) Anti-EbpA activity of pooled sera from mice immunized with the indicated EbpA dose or mock-immunized (PBS) collected over 12 weeks and following 24 hours post-infection (24 hpi) analyzed by ELISA. All sera are analyzed at a dilution of 1:1,000,000. Values represent the mean ±SEM derived from at least 3 independent determinations of each pooled sample.

(FIG. 13A) Mice were passively immunized with EbpA$^{Full}$ or EbpA$^{NTD}$ mouse sera 4 hours prior to infection with *E. faecalis* and catheter implantation. At 12 hours post-infection, a portion of the mice were boosted with EbpA$^{Full}$ or EbpA$^{NTD}$ mouse sera. Animals were sacrificed at 24 hours post-infection and bacterial counts in the bladder and on the catheter were enumerated. (FIG. 13B) Bacterial counts in the bladder revealed a significant reduction in bacterial numbers in both the single dose and two dose treatment regimen following immunization with either EbpA$^{Full}$ or EbpA$^{NTD}$ mouse sera. (FIG. 13C) Bacterial counts on the catheter revealed a significant reduction in bacterial numbers in both the single dose and two dose treatment regimen following immunization with either EbpA$^{Full}$ or EbpA$^{NTD}$ mouse sera.

(FIG. 14A) Mice were implanted with catheters and infected with *E. faecalis*. At 12 hours post-infection, mice were immunized with EbpA$^{Full}$, EbpA$^{NTD}$ or EbpA$^{CTD}$ mouse sera (red arrow). Animals were sacrificed at 24 hours post-infection and bacterial counts in the bladder and on the catheter were enumerated. (FIG. 14B) Bacterial counts in the bladder revealed a significant reduction in bacterial numbers following immunization with either EbpA$^{Full}$ or EbpA$^{NTD}$ mouse sera, however a significant reduction in bacterial counts was not observed following immunization with the EbpA$^{CTD}$ mouse sera. (FIG. 14C) Bacterial counts on the catheter revealed a significant reduction in bacterial following immunization with either EbpA$^{Full}$ or EbpA$^{NTD}$ mouse sera, however a significant reduction in bacterial counts was not observed following immunization with the EbpA$^{CTD}$ mouse sera.

(FIG. 16A) Mice were implanted with catheters and infected with various Enterococci clinical isolates. At 12 hours post-infection, mice were immunized with EbpA$^{NTD}$ mouse sera. Animals were sacrificed at 24 hours post-infection and bacterial counts in the bladder were enumerated. (FIG. 16B) In each Enterococci clinical isolate tested, immunization with EbpA$^{NTD}$ mouse sera significantly reduced bacterial counts in the bladder.

DETAILED DESCRIPTION OF THE INVENTION

Figure 1A:
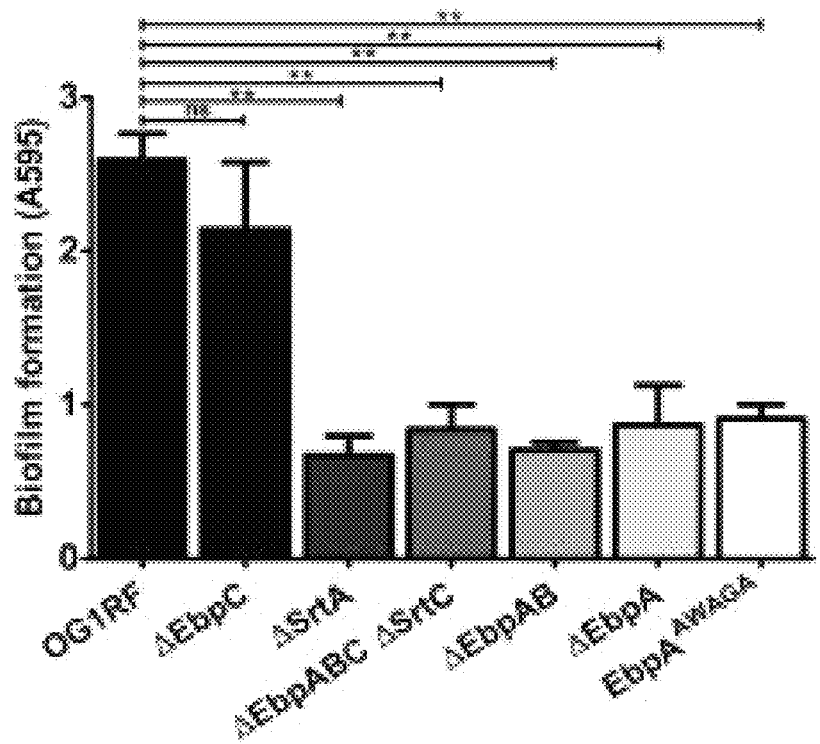
FIG. 1A, FIG. 1B, FIG. 1C, FIG. 1D and FIG. 1E depicts graphs and a schematic showing that EbpA$^{NTD}$ is critical for biofilm formation and fibrinogen recognition.
Figure 1B:
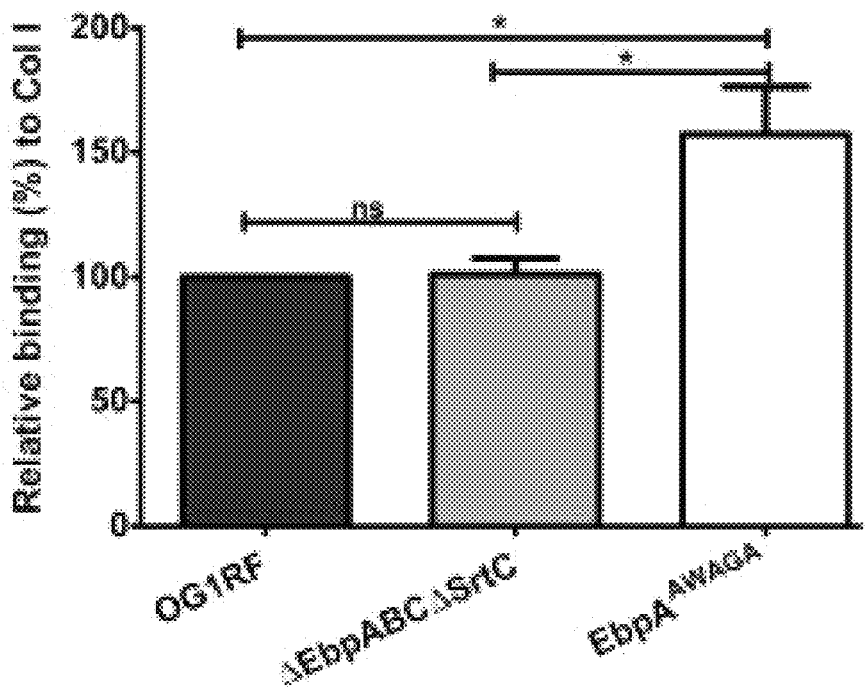

The present disclosure encompasses compositions and methods for preventing and treating EbpA-associated infections. Specifically, the present disclosure encompasses compositions and methods for preventing and treating *Enterococcus*-mediated catheter-associated urinary tract infections (CAUTIs). The inventors unexpectedly discovered that a vaccine composition comprising EbpA effectively prevents CAUTIs. Prior to this disclosure, the mechanism of *Enterococcus*-mediated CAUTIs was unknown. Accordingly, it was unpredictable that a vaccine comprising EbpA could potentially treat or prevent CAUTIs. What the inventors discovered is that host fibrinogen coats indwelling catheters and that EbpA is essential for binding to fibrinogen-coated catheters. Further, the inventors surprisingly discovered that the N-terminal domain of EbpA is essential to induce protective immunity and that neither the C-terminal domain of EbpA nor the other pilus subunits (EbpC and EbpB) result in any amount of protective immunity.

I. Compositions

Compositions of the invention are directed to vaccine compositions comprising the N-terminal domain of endocarditis- and biofilm-associated pilus (Ebp) subunit A. Compositions of the invention are also directed to anti-EbpA N-terminal domain antibodies and compositions comprising said antibodies. Various aspects of the invention will be described in further detail below.

(a) EbpA NTD

In an aspect, the present invention encompasses a vaccine composition, wherein the vaccine composition comprises the N-terminal domain of EbpA. The term "vaccine composition" as used herein means a composition that when administered to a subject, typically elicits a protective immune response, where a protective immune response is one that ameliorates one or symptoms of the target disorder. As used herein, "EbpA" refers to the minor subunit at the tip of the endocarditis- and biofilm-associated pilus (Ebp). The Ebp pilus is a member of the sortase-assembled pilus family and is a heteropolymer composed of three subunits: the major shaft subunit (EbpC) and the minor subunits at the base (EbpB) and tip (EbpA) of the fiber. The inventors have discovered that EbpA is an adhesin that mediates bacterial attachment to host fibrinogen. The nucleotide sequence of *Enterococcus faecalis* may be found in GenBank accession number CP002491.1, of which position 1495416 . . 1498727 represents the ebpA nucleotide sequence. The amino acid sequence of *Enterococcus faecalis* EbpA may be found in GenBank accession number ADX79769.1 or GenBank accession number YP_005705502.1. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details.

In some embodiments, a homolog has at least 80%, at least 81%, at least 82%, at least 83%, at least 84%, at least 85%, at least 86%, at least 87%, at least 88%, or 89% identity to EbpA. In another embodiment, a homolog has at least 90%, at least 91%, at least 92%, at least 93%, at least 94%, at least 95%, at least 96%, at least 97%, at least 98%, at least 99%, or at least 100% identity to EbpA. In yet another embodiment, EbpA may be a truncation or variant that has the same activity as the full length EbpA.

A vaccine composition of the invention comprises the N-terminal domain (NTD) of EbpA. The "NTD of EbpA" or "EbpA NTD" may also be referred to as the "antigen" or "antigenic component" of the vaccine composition. In an embodiment, the NTD of EbpA may comprise from about amino acid 1 to about amino acid 650 relative to the full length EbpA sequence (SEQ ID NO:5). In another embodiment, the NTD of EbpA may start at about amino acid 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 relative to the full length EbpA sequence (SEQ ID NO:5). In still another embodiment, the NTD of EbpA may end at about amino acid 575, 580, 585, 590, 595, 600, 605, 610, 615, 620, 625 or 630 relative to the full length EbpA sequence (SEQ ID NO:5). In other embodiments, the NTD of EbpA may comprise about amino acids 85 to 600, or about amino acids 90 to 595, or about amino acids 95 to 590, or about amino acids 100 to 585, or about amino acids 105 to 580, or about amino acids 110 to 577, or about amino acids 115 to 577, or about amino acids 120 to 577, or about amino acids 125 to 577, or about amino acids 130 to 577, or about amino acids 130 to 577, or about amino acids 135 to 577, or about amino acids 140 to 577, or about amino acids 145 to 577, or about amino acids 150 to 577, or about amino acids 155 to 577, or about amino acids 160 to 577, or about amino acids 165 to 577, or about amino acids 170 to 577, or about amino acids 175 to 577, or about amino acids 180 to 577, or about amino acids 185 to 577, or about amino acids 190 to 577, or about amino acids 195 to 577, or about amino acids 200 to 577. In a specific embodiment, the NTD of EbpA comprises amino acids 115-577. Amino acids 115-577 comprise SEQ ID NO:3 (PEKITV PENTKETNKN DSAPEKTEQP TATEEV- TNPF AEARMAPATL RANLALPLIA PQYTTDNSGT YPTANWQPTG NQNVLNHQGN KDGSAQWDGQ TS- WNGDPTNR TNSYIEYGGT GDQADYAIRK YARETT- TPGL FDVYLNVRGN VQKEITPLDL VLVVDWSGSM NENNRIGEVQ KGVNRFVDTL ADSGITNNIN MGYV- GYSSDG YNNNAIQMGP FDTVKNPIKN ITPSSTRGGT FTQKALRDAG DMLATPNGHK KVIVLLTDGV PTF- SYKVSRV QTEADGRFYG TQFTNRQDQP GSTSYISG- SY NAPDQNNINK RINSTFIATI GEAMALKQRG IEIH- GLGIQL QSDPRANLSK QQVEDKMREM VSADEN- GDLY YESADYAPDI SDYLAKKAVQ ISGTVVNGKV VDPIAEPFKY EPNTLSMKSV GPVQVQTLPE VSLT- GATINS NEIYLGKGQE IQIHYQV). In an embodiment, the present invention encompasses the NTD of EbpA comprising at least 80% identity to SEQ ID NO:3. For example, the NTD of EbpA may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:3.

The NTD of EbpA comprises a MIDAS-containing vWA domain, which is important for adhesion to extracellular matrix (ECM) proteins, and a fibrinogen-binding SdrG-like domain. A SdrG domain is a domain of an adhesin found only on the cell walls of bacteria. More specifically, SdrG is only found in gram-positive bacteria. This particular domain binds to a glycoprotein named fibrinogen. SdrG stands for serine-aspartate dipeptide repeats, which as its name suggests, contains repeats of two amino acids, serine and aspartate. In a specific embodiment, the EbpA NTD comprises a fibrinogen-binding domain. Structural features common to a fibrinogen-binding domain may be core beta-sandwich topologies. The fibrinogen-binding domain may comprise about amino acid 175 to about amino acid 575. One of skill in the art will be able to determine the amino acids encompassing the fibrinogen-binding domain. In another specific embodiment, the EbpA NTD comprises a MIDAS motif. A MIDAS motif is a sequence motif representing a metal-ion-dependent adhesion site (MIDAS) that confers divalent metal (usually Mg2+)-dependent binding. In a specific embodiment, the MIDAS motif sequence is DxSxS (SEQ ID NO:4). For example, the MIDAS motif sequence may be DWSGS (SEQ ID NO:2). In an exemplary embodiment, the MIDAS motif comprises amino acids 275-279.

In an aspect, a vaccine composition of the invention may comprise more than one EbpA N-terminal domain. For example, the vaccine composition may comprise 2, 3, 4, 5, 6, 7, 8, 9 or 10 EbpA N-terminal domains. Additionally, the vaccine composition may comprise more than 10 EbpA N-terminal domains. The EbpA NTDs may be the same or different. The EbpA N-terminal domains may be linked together by various methods known in the art. Suitable linkers include amino acid chains and alkyl chains functionalized with reactive groups for coupling to 2 or more EbpA NTDs. In an embodiment, the linker may include amino acid side chains, referred to as a peptide linker. Accordingly, additional amino acid residues may be added at the amino terminus of a EbpA NTD of the invention for the purpose of providing a linker by which the EbpA NTDs of the present invention can be conveniently affixed to a label or solid matrix, or carrier. Amino acid residue linkers are usually at least one residue and can be 40 or more residues, more often 1 to 10 residues, but do not comprise the EbpA NTD. Typical amino acid residues used for linking are tyrosine, cysteine, lysine, glutamic and aspartic acid, or the like.

In another embodiment, an alkyl chain linking group may be coupled to the EbpA NTD by reacting the amino group of the N-terminal residue of the EbpA NTD of the invention with a first functional group on the alkyl chain, such as a carboxyl group or an activated ester. Subsequently the second EbpA NTD is attached to the alkyl chain to complete the formation of the complex by reacting a second functional group on the alkyl chain with an appropriate group on the second EbpA NTD. The second functional group on the alkyl chain is selected from substituents that are reactive with a functional group on the EbpA NTD while not being reactive with the N-terminal residue of the first EbpA NTD. The process may be repeated for the addition of subsequent EbpA NTDs.

An alternative chemical linking group to an alkyl chain is polyethylene glycol (PEG), which is functionalized in the same manner as the alkyl chain described above. The EbpA NTDs of the invention may be PEGylated for improved systemic half-life and reduced dosage frequency. In an embodiment, PEG may be added to a linker. As such, an EbpA NTD of the invention may comprise a linker and PEG.

The vaccine compositions of the invention may include a pharmaceutically acceptable excipient such as a suitable adjuvant. Suitable adjuvants include an aluminium salt such as aluminium hydroxide or aluminium phosphate, but may also be a salt of calcium, iron or zinc, or may be an insoluble suspension of acylated tyrosine, or acylated sugars, or may be cationically or anionically derivatised saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the invention include cytokines such as interleukins (e.g. IL-1, IL-2, IL-4, IL-5, IL-6, IL-7, IL-12, etc), macrophage colony stimulating factor (M-CSF), tumour necrosis factor (TNF), granulocyte, macrophage colony stimulating factor (GM-CSF) may also be used as adjuvants. In an exemplary embodiment, the adjuvant is selected from the group consisting of Freund's complete adjuvant and Freund's incomplete adjuvant.

Vaccines of the invention will typically, in addition to the antigenic and adjuvant components mentioned above, comprise one or more "pharmaceutically acceptable carriers or excipients", which include any excipient that does not itself induce the production of antibodies harmful to the individual receiving the composition. Suitable excipients are typically large, slowly metabolised macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, 20$^{th}$ edition, ISBN: 0683306472.

Compositions of the invention may be lyophilised or in aqueous form, i.e. solutions or suspensions. Liquid formulations of this type allow the compositions to be administered direct from their packaged form, without the need for reconstitution in an aqueous medium, and are thus ideal for injection. Compositions may be presented in vials, or they may be presented in ready filled syringes. The syringes may be supplied with or without needles. A syringe will include a single dose of the composition, whereas a vial may include a single dose or multiple doses (e.g. 2 doses).

Liquid vaccines of the invention are also suitable for reconstituting other vaccines from a lyophilized form. Where a vaccine is to be used for such extemporaneous reconstitution, the invention provides a kit, which may comprise two vials, or may comprise one ready-filled syringe and one vial, with the contents of the syringe being used to reconstitute the contents of the vial prior to injection.

Vaccines of the invention may be packaged in unit dose form or in multiple dose form (e.g. 2 doses). For multiple dose forms, vials are preferred to pre-filled syringes. Effective dosage volumes can be routinely established, but a typical human dose of the composition for injection has a volume of 0.5 mL.

In one embodiment, vaccines of the invention have a pH of between 6.0 and 8.0, in another embodiment, vaccines of the invention have a pH of between 6.3 and 6.9, e.g. 6.6±0.2.

Vaccines may be buffered at this pH. Stable pH may be maintained by the use of a buffer. If a composition comprises an aluminium hydroxide salt, a histidine buffer may be used (WO03/009869). The composition should be sterile and/or pyrogen free.

Compositions of the invention may be isotonic with respect to humans.

Vaccines of the invention may include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

Vaccines of the invention may comprise a detergent e.g. a Tween (polysorbate), such as Tween 80. Detergents are generally present at low levels e.g. <0.01%.

Vaccines of the invention may include sodium salts (e.g. sodium chloride) to give tonicity. The composition may comprise sodium chloride. In one embodiment, the concentration of sodium chloride in the composition of the invention is in the range of 0.1 to 100 mg/mL (e.g. 1-50 mg/mL, 2-20 mg/mL, 5-15 mg/mL) and in a further embodiment the concentration of sodium chloride is 10±2 mg/mL NaCl e.g. about 9 mg/mL.

Vaccines of the invention will generally include a buffer. A phosphate or histidine buffer is typical.

Vaccines of the invention may include free phosphate ions in solution (e.g. by the use of a phosphate buffer) in order to favor non-adsorption of antigens. The concentration of free phosphate ions in the composition of the invention is in one embodiment between 0.1 and 10.0 mM, or in another embodiment between 1 and 5 mM, or in a further embodiment about 2.5 mM.

(b) Antibodies

In another aspect, the present invention encompasses an antibody, wherein the antibody is generated from EbpA NTD. Methods of generating an antibody to a protein are well known in the art. For example, monoclonal antibodies may be generated using a suitable hybridoma as would be readily understood by those of ordinary skill in the art. In the preferred process, a protein in accordance with the invention is first identified and isolated. Next, the protein is isolated and/or purified in any of a number of suitable ways commonly known in the art, or after the protein is sequenced, the protein used in the monoclonal process may be produced by recombinant means as would be commonly used in the art and then purified for use. In one suitable process, monoclonal antibodies may be generated from proteins isolated and purified as described above by mixing the protein with an adjuvant, and injecting the mixture into a laboratory animal. Immunization protocols may consist of a first injection (using complete Freund's adjuvant), two subsequent booster injections (with incomplete Freund's adjuvant) at three-week intervals, and one final booster injection without adjuvant three days prior to fusion. For hybridoma production, the laboratory animal may be sacrificed and their spleen removed aseptically. Antibody secreting cells may be isolated and mixed with myeloma cells (NS1) using drop-wise addition of polyethylene glycol. After the fusion, cells may be diluted in selective medium (vitamin-supplemented DMEM/HAT) and plated at low densities in multiwell tissue culture dishes. Tissue supernatants from the resulting fusion may be screened by both ELISA and immunoblot techniques. Cells from these positive wells may be grown and single cell cloned by limiting dilution, and supernatants subjected to one more round of screening by both ELISA and immunoblot. Positive clones may be identified, and monoclonal antibodies collected as hybridoma supernatants.

Anti-EbpA NTD antibodies useful herein include all antibodies that specifically bind an epitope within EbpA NTD. EbpA NTD may be as described in Section I(a). An anti-EbpA NTD antibody may be an antibody found in the sera of a subject administered an EbpA NTD. The term "antibody" includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv, regions, of antibodies with this specificity.

Preferably, but not necessarily, the antibodies useful in the discovery are produced recombinantly, as manipulation of the typically murine or other non-human antibodies with the appropriate specificity is required in order to convert them to humanized form. Antibodies may or may not be glycosylated, though glycosylated antibodies are preferred. Antibodies are properly cross-linked via disulfide bonds, as is known.

The basic antibody structural unit of an antibody useful herein comprises a tetramer. Each tetramer is composed of two identical pairs of polypeptide chains, each pair having one "light' (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites. The chains exhibit the same general structure of relatively conserved framework regions (FR) joined by three hypervariable regions, also called complementarity determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-EbpA NTD antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with a peptide representing an epitope encompassing a region of the EbpA NTD protein coding sequence or an appropriate subregion thereof. Materials for recombinant manipulation can be obtained by retrieving the nucleotide sequences encoding the desired antibody from the hybridoma or other cell that produces it. These nucleotide sequences can then be manipulated and isolated, characterized, purified and, recovered to provide them in humanized form, for use herein if desired.

As used herein "humanized antibody" includes an anti-EbpA NTD antibody that is composed partially or fully of amino acid sequence sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for EbpA NTD is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-EbpA NTD antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immunoglobulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immunoglobulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immunoglobulin model (Queen, et al., op. cit., and Co, et al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

In all instances, an antibody of the invention specifically binds EbpA NTD. The phrase "specifically binds" herein means antibodies bind to the protein with an affinity constant or Affinity of interaction ($K_D$) in the range of at least 0.1 mM to 1 pM, or in the range of at least 0.1 pM to 10 nM, with a preferred range being 0.1 pM to 1 nM. EbpA may be found in a variety of Gram positive species, and methods of determining whether an antibody binds to EbpA NTD are known in the art. Accordingly, antibodies of the invention may also bind EbpA NTD from other species.

The antibodies of the present invention may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

An isolated antibody of the present invention that binds to EbpA NTD preferably recognizes one of several epitopes. In one embodiment, the isolated antibody of the present invention that binds to EbpA NTD recognizes an epitope within the amino acid sequence of SEQ ID NO:3.

(c) Pharmaceutical Formulation

The vaccine composition or antibody disclosed herein can be formulated into various dosage forms and administered by a number of different means that will deliver a therapeutically effective amount of the antigen or antibody. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be an intramuscular formulation.

Solid dosage forms for oral administration include capsules, tablets, caplets, pills, powders, pellets, and granules. In such solid dosage forms, the active ingredient is ordinarily combined with one or more pharmaceutically acceptable excipients. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, an antigen or antibody of the invention is encapsulated in a suitable vehicle to either aid in the delivery of the antigen or antibody to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of antigen or antibody in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, antigen may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), phosphatidylethanolamine (PE), and linear polyethylenimine (l-PEI). In a specific embodiment, the liposome may be comprised of linear polyethylenimine (l-PEI). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying antigen or antibody may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The antigen or antibody may be encapsulated in a microemulsion by any method generally known in the art.

In yet another embodiment, antigen or antibody may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, the present invention encompasses a method of treating an EbpA-associated infection in a subject. The method comprises administering to the subject an effective amount of a vaccine composition comprising EbpA NTD. Alternatively, the method comprises administering to the subject an effective amount of a composition comprising an anti-EbpA NTD antibody. The term "infection" as used herein includes presence of microbes, including bacteria, in or on a subject, which, if its growth were inhibited, would result in a benefit to the subject. As such, the term "infection" in addition to referring to the presence of bacteria also refers to normal flora which, are not desirable. The term "infection" includes infection caused by bacteria. An "EbpA-associated infection" may be an infection caused by a bacterium in which the EbpA protein is important for virulence. It must be realized, that any bacterium expressing EbpA or an EbpA homolog may require the EbpA protein for virulence. Methods of identifying an EbpA homolog are described in Section I(a). Other Gram-positive bacteria may express homologs of EbpA, specifically homologs of the EbpA NTD. Accordingly, a vaccine composition comprising EbpA NTD or a composition comprising an anti-EbpA NTD antibody may treat an infection caused by *Stapylococcus, Streptococcus,* and *Enterococcus* or other Gram-positive bacteria. Routine experimentation would allow a skilled artisan to determine if the Gram-positive bacterial infection is mediated by EbpA. In a specific embodiment, a vaccine composition comprising EbpA NTD or a composition comprising an anti-EbpA NTD antibody may treat an infection caused by *Enterococcus*. In another specific embodiment, a vaccine composition comprising EbpA NTD or a composition comprising an anti-EbpA NTD antibody may treat an infection cause by *Enterococcus faecalis*. Non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, septicemia and surgical infections.

In another aspect, the present invention encompasses a method of treating an infection on medical devices or implanted materials. The method comprises administering an effective amount of a vaccine composition comprising EbpA NTD. Alternatively, the method comprises administering an effective amount of a composition comprising an anti-EbpA NTD antibody. In a specific embodiment, the infection is an EbpA-mediated infection as described above. In certain embodiments, the medical device or implanted material is disposed in a subject. In such an embodiment, a composition of the invention is administered to a subject. In other embodiments, the medical device or implanted material is not disposed in a subject. In such an embodiment, a composition of the invention is administered to the medical device or implanted material prior to disposing the medical device or implanted material into the subject. The composition may be administered immediately before inserting into a subject or minutes, hours, days, weeks or months before inserting into a subject. Medical devices or polymeric biomaterials include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing. In a specific embodiment, the medical device is a urethral/ureteral/urinary device (Foley catheter, stent, tube and balloon).

In still another aspect, the present invention encompasses a method of treating catheter-associated urinary tract infections (CAUTIs) in a subject. The method comprises administering to the subject an effective amount of a vaccine composition comprising EbpA NTD. Alternatively, the method comprises administering to the subject an effective amount of a composition comprising an anti-EbpA NTD antibody. In a specific embodiment, the CAUTI is caused by *Enterococcus*. In another specific embodiment, the CAUTI is caused by *E. faecalis*. The inventors have discovered that EbpA of *Enterococcus faecalis* binds to fibrinogen released from the subject and deposited on the indwelling device. Unexpectedly, the inventors discovered that the NTD is responsible for mediating binding of EbpA to fibrinogen. Accordingly, as demonstrated in the Examples, administration of a vaccine comprising the EbpA NTD results in protection of the subject from CAUTI. Alternatively, administration of a composition comprising an anti-EbpA NTD antibody results in protection of the subject from CAUTI. Still further, administration of a vaccine comprising the EbpA NTD or administration of a composition comprising an anti-EbpA NTD antibody results in treatment of a subject with a CAUTI.

The term "treat", "treating" or "treatment" as used herein refers to administering a pharmaceutical composition of the invention for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering a pharmaceutical composition of the invention in order to: (i) reduce or eliminate either an EbpA-associated infection or one or more symptoms of the EbpA-associated infection, or (ii) retard the progression of an EbpA-associated infection or of one or more symptoms of the EbpA-associated infection, or (iii) reduce the severity of an EbpA-associated infection or of one or more symptoms of the EbpA-associated infection, or (iv) suppress the clinical manifestation of an EbpA-associated infection, or (v) suppress the manifestation of adverse symptoms of the EbpA-associated infection.

The term "control" or "controlling" as used herein generally refers to preventing, reducing, or eradicating an EbpA-associated infection or inhibiting the rate and extent of such an infection, or reducing the microbial population, such as a microbial population present in or on a body or structure, surface, liquid, subject, etc, wherein such prevention or reduction in the EbpA-associated infection or microbial population is statistically significant with respect to untreated infection or population. In general, such control may be achieved by increased mortality amongst the microbial population.

The compositions of the present invention may be used to protect or treat a subject susceptible to infection by EbpA-expressing bacteria, or more preferably, by *Enterococcus*, by means of administering said composition directly to a subject. The term "administration" or "administering" includes delivery of a composition or one or more pharmaceutically active ingredients to a subject, including for example, by any appropriate methods, which serves to deliver the composition or it's active ingredients or other pharmaceutically active ingredients to the site of the infection. The method of administration can vary depending on various factors, such as for example, the components of the pharmaceutical composition or the type/nature of the pharmaceutically active or inert ingredients, the site of the potential or actual infection, the microorganism involved, severity of the infection, age and physical condition of the subject. Direct delivery may be accomplished by parenteral injection (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In one embodiment, administration is by intramuscular injection to the thigh or the upper arm. Injection may be via a needle (e.g. a hypodermic needle, electroporation device), but needle free injection may alternatively be used. A typical intramuscular dose is 0.5 mL. The composition can be administered prophylactically (i.e. to prevent infection) or therapeutically (i.e. to treat infection). An immune response is preferably protective. The method may raise a booster response.

The invention provides a method for treating EbpA-associated infection in a subject, comprising the step of administering an effective amount of a composition of the invention. The term "effective amount" as used herein refers to an amount, which has a therapeutic effect or is the amount required to produce a therapeutic effect in a subject. For example, a therapeutically or pharmaceutically effective amount of a composition is the amount of the antigen required to produce a desired therapeutic effect as may be judged by clinical trial results and/or model animal infection studies. The effective or pharmaceutically effective amount depends on several factors, including but not limited to, the route of administration, the microorganism (e.g. bacteria) involved, characteristics of the subject (for example height, weight, sex, age and medical history), severity of infection, location of infection, the particular type of antigen used and/or the particular antibody used. For prophylactic treatments, a therapeutically or prophylactically effective amount is that amount which would be effective to prevent a microbial (e.g. bacterial) infection.

The effective amount of antigen in each vaccine dose is selected as an amount which induces an immunoprotective response without significant adverse side effects in typical vaccines. Accordingly, the exact amount of the antigen that is required to elicit such a response will vary from subject to subject, depending on the species, age, and general condition of the subject, the severity of the condition being treated, the particular carrier or adjuvant being used and its mode of administration, and the like. Generally it is expected that each dose will comprise 1-1000 µg of total antigen, or 1-100 µg, or 1-40 µg, or 1-5 µg, or less than 1 µg. An optimal amount for a particular vaccine can be ascertained by studies involving observation of antibody titres and other responses in subjects. In certain embodiments, the vaccine composition is administered at a dose ranging from about 50 to 150 µg. In another embodiment, the vaccine composition is administered at a dose of about 100 µg. In an exemplary embodiment, the vaccine composition is administered at a dose ranging from 0.3 to 100 µg.

The concentration of anti-EbpA NTD antibody in compositions to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition comprising an anti-EbpA NTD antibody for injection to a living subject could be made up to contain from 1-5 mL sterile buffered water of phosphate buffered saline and about 1-5000 mg of anti-EbpA NTD antibody. A typical composition for intravenous infusion could have volumes between 1-250 mL of fluid, such as sterile Ringer's solution, and 1-100 mg per ml, or more in anti-EbpA NTD antibody concentration. Doses will vary from subject to subject based on size, weight, and other physio-biological characteristics of the subject receiving the successful administration. In an aspect, a typical dose contains from about 0.01 mg/kg to about 100 mg/kg of an anti-EbpA NTD antibody described herein. Doses can range from about 0.05 mg/kg to about 100 mg/kg, more preferably from about 0.1 mg/kg to about 50 mg/kg, or from 0.5 mg/kg to about 50 mg/kg, or from about 10 mg/kg to about 50 mg/kg. In a specific embodiment, the dose of anti-EbpA NTD antibody may range from about 10 mg/kg to about 50 mg/kg.

Following initial administration of a composition of the invention, subjects may receive one or several additional administrations of the composition adequately spaced. Dosing treatment can be a single dose schedule or a multiple dose schedule. Suitable timing between doses (e.g. between 4-16 weeks) can be routinely determined.

In the prevention of an infection, a composition of the invention may be administered as multiple doses prior to infection or prior to insertion of the medical device or implanted material. In the treatment of an infection, a composition of the invention may be administered as multiple doses following infection or following insertion of the medical device or implanted material. Administration may be daily, twice daily, weekly, twice weekly, monthly, twice monthly, every 6 weeks, every 3 months, every 6 months or yearly. For example, administration may be every 2 weeks, every 3 weeks every 4 weeks, every 5 weeks, every 6 weeks, every 7 weeks, every 8 weeks, every 9 weeks, every 10 weeks, every 11 weeks or every 12 weeks. Alternatively, administration may be every 1 month, every 2 months, every 3 months, every 4 months, every 5 months, every 6 months, every 7 months, every 8 months, every 9 months, every 10 months, every 11 months or every 12 months. Still further, administration may be every 1 year, every 2 years, every 3 years, every 4 years, every 5 years, every 6 years, every 7 years, every 8 years, every 9 years, every 10 years, every 15 years or every 20 years. The duration of treatment can and will vary depending on the subject and the infection to be prevented or treated. For example, the duration of treatment may be for 1 week, 2 weeks, 3 weeks, 4 weeks, 5 weeks, 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, administration may be every 4 weeks for 6 months to a year and then administration may be every year thereafter. The duration of treatment may also depend on the length of time the medical device or implanted material is to remain in the subject. For example, when the medical device or implanted material is to remain in the subject for a long period of time, the duration of treatment may be extended. In contrast, when the medical device or implanted material is to remain in the subject for a shorter period of time, the duration of treatment may be shortened. In a specific embodiment, the duration of treatment may be once a day for the duration of time the medical device or implanted material remains in a subject. A skilled artisan would be able to determine the effective dosing regimen based on the medical history and duration of indwelling device in the subject.

A method of the invention may further comprise administering an antimicrobial agent. As used herein, an "antimicrobial agent" is an agent that kills microorganisms or inhibits their growth. An antimicrobial agent may be a disinfectant, an antiseptic and/or an antibiotic. Non-limiting examples of antimicrobial agents include aminoglycosides such as amikacin, gentamicin, kanamycin, neomycin, netilmicin, tobramycin, paromomycin, streptomycin, spectinomycin; ansamycins such as geldanamycin, herbimycin, rifaximin; carbachephems such as loracarbef; carbapenems such as ertapenem, doripenem, imipenem/cilastatin, meropenem; cephalosporins such as cefadroxil, cefazolin, cefalotin, cefalothin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole; glycopeptides such as teicoplanin, vancomycin, telavancin, dalbavancin, oritavancin; lincosamides such as clindamycin, lincomycin; lipopeptides such as daptomycin; macrolides such as azithromycin, clarithromycin, dirithromycin, erythromycin, roxithromycin, troleandomycin, telithromycin, spiramycin; monobactams such as aztreonam; nitrofurans such as furazolidone, nitrofurantoin; oxazolidinones such a linezolid, posizolid, radezolid, torezolid; penicillins such as amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin; penicillin combinations such as amoxicillin/clavulanate, ampicillin/sulbactam, piperacillin/tazobactam, ticarcillin/clavulanate; polypeptides such as bacitracin, colistin, polymyxin B, quinolones/fluoroquinolones such as ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin; sulfonamides such as mafenide, sulfacetamide, sulfadiazine, silver sulfadiazine, sulfadimethoxine, sulfamethizole, sulfamethoxazole, sulfanilamide, sulfasalazine, trimethoprim-sulfamethoxazole (TMP-SMX, co-trimoxazole); tetracyclines such as demeclocycline, doxycycline, minocycline, oxytetracyline, tetracycline; mycobacterial agents such as clofazimine, dapsone, capreomycin, cycloserine, ethambutol, ethionamide, isoniazid, pyrazinamide, rifampicin, rifampin, rifabutin, rifapentine, streptomycin; and others such as arsphenamine, chloramphenicol, fosfomycin, fusidic acid, metronidazole, mupirocin, plantesimycin, quinupristin/dalfopristin, thiamphenicol, tigecylcine, tinidazole, trimethoprim, teixobactin. In a specific embodiment, the antimicrobial agent may be selected from the group consisting of trimethoprim/sulfamethoxazole, fosfomycin, nitrofurantoin, ciprofloxacin, levofloxacin, cephalexin, ceftriaxone, azithromycin, and doxycycline.

As used herein, "subject" or "patient" is used interchangeably. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human.

(a) Methods of Using Anti-EbpA NTD Antibodies

In another aspect, the present invention encompasses methods for detecting an EbpA-associated infection. The method comprises (a) collecting a biological sample from a subject, (b) contacting the biological sample with an anti-EbpA NTD antibody of the invention, (c) identifying or diagnosing a subject as having an EbpA-associated infection when the antibody recognizes EbpA NTD present in the biological sample. Alternatively, the method generally comprises (i) obtaining a biological sample from a subject; (ii) measuring the amount of EbpA NTD in the sample using an anti-EbpA NTD antibody of the invention, (iii) comparing the amount of EbpA NTD in the sample to a reference value, and (iv) classifying the subject as having a high or low amount of EbpA NTD relative to the reference value based on the amount of EbpA NTD measured in the sample.

As used herein, the term "biological sample" refers to a sample obtained from a subject. Any biological sample containing EbpA is suitable. Numerous types of biological samples are known in the art. Suitable biological sample may include, but are not limited to, tissue samples or bodily fluids. In some embodiments, the biological sample is a tissue sample such as a tissue biopsy of tissues, bone, muscle, cartilage, or skin. The tissue biopsy may be a biopsy of a known or suspected infection. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. In other embodiments, the sample may be a bodily fluid. Non-limiting examples of suitable bodily fluids include blood, plasma, serum, urine, saliva, sputum, ascites, pleural effusion, or cerebrospinal fluid. The fluid may be used "as is", the cellular components may be isolated from the fluid, or a protein fraction may be isolated from the fluid using standard techniques. Still further, the biological sample may be all or a portion of a medical device or implanted material.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that EbpA can be accurately detected and the amount measured according to the invention.

Once a sample is obtained, it is processed in vitro to detect and measure the amount of EbpA NTD using an anti-EbpA NTD antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a sandwich immunoassay, a radioimmunoassay, an immunoblot or Western blot, flow cytometry, immunohistochemistry, and an array.

In general, an antibody-based method of detecting and measuring an amount of EbpA NTD comprises contacting some of the sample, or all of the sample, comprising EbpA NTD with an anti-EbpA NTD antibody under conditions effective to allow for formation of a complex between the antibody and the EbpA NTD. Typically, the entire sample is not needed, allowing one skilled in the art to repeatedly detect and measure the amount of EbpA NTD in the sample. The method may occur in solution, or the antibody or EbpA NTD comprising the sample may be immobilized on a solid surface. Non-limiting examples of suitable surfaces may include microtitre plates, test tubes, slides, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-EbpA NTD antibody may also be attached to the substrate non-covalently. For example, a biotinylated anti-EbpA NTD antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-EbpA NTD antibody composition to the sample and incubating the mixture for a period of time long enough for the anti-EbpA NTD antibody to bind to any antigen present. After this time, the complex will be washed and the complex may be detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase, and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-EbpA NTD antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-NGA3B antibody attached to the substrate is located at one or more spatially defined addresses of the array. For example, an array may comprise at least one, at least two, at least three, at least four, or at least five anti-EbpA NTD antibodies, each antibody recognizing the same or different EbpA NTD epitope, and each antibody may be at one, two, three, four, five, six, seven, eight, nine, ten or more spatially defined addresses.

For each of the foregoing embodiments, EbpA NTD may be first isolated or enriched before detection. For instance, EbpA NTD may be enriched or isolated using liquid chromatography, by precipitation, electrophoresis, or affinity purification. In some embodiments, EbpA NTD may be enriched or purified using liquid chromatography. In other embodiments, EbpA NTD may be enriched or purified using electrophoresis.

In certain embodiments, EbpA NTD may be enriched or purified by affinity purification before detection. Specifically, EbpA NTD may be enriched or purified by affinity purification using an antibody of the invention. Methods of enriching a sample for EbpA NTD or purifying EbpA NTD using affinity purification are known in the art. In short, affinity purification comprises incubating a sample with a solid support, such as beads, a culture plate, or a membrane, that facilitates later steps. A solid support may be coated with an antibody of the invention, causing EbpA NTD to attach to the solid support. Alternatively, a sample may be incubated with an antibody of the invention, and the EbpA NTD-antibody complex may be isolated by incubating with a solid support coated with a second antibody with specificity to an antibody of the invention, causing a EbpA NTD-antibody complex to attach to the solid support. EbpA NTD may then be purified or enriched by washing other material in the sample that is not bound to the solid support, or, if the solid support is superparamagnetic beads, EbpA NTD attached to the beads may be separated from the sample by attraction to a strong magnetic field. Upon enrichment or purification, EbpA NTD may then be detected in the enriched or purified sample using any of the methods described above.

Any suitable reference value known in the art may be used. For example, a suitable reference value may be the amount of EbpA NTD in a biological sample obtained from a subject or group of subjects of the same species that has no detectable EbpA-associated infection. In another example, a suitable reference value may be the amount of EbpA NTD in biological sample obtained from a subject or group of subjects of the same species that has detectable EbpA-associated infection as measured via standard methods such as culture. In another example, a suitable reference value may be a measurement of the amount of EbpA NTD in a reference sample obtained from the same subject. The reference sample comprises the same type of biological fluid as the test sample, and may or may not be obtained from the subject when EbpA-associated infection was not suspected. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began.

According to the invention, a subject may be classified based on the amount of EbpA NTD measured in the sample. Classifying a subject based on the amount of EbpA NTD measured in a sample of biological fluid obtained from the subject may be used to identify subjects with a EbpA-associated infection. Generally speaking, a subject may be classified as having a high or low amount of EbpA NTD compared to a reference value, wherein a high amount of EbpA NTD is an amount above the reference value and a low amount is an amount equal to or below the reference value. In preferred embodiments, to classify a subject as having a high amount of EbpA NTD, the amount of EbpA NTD in the sample compared to the reference value may be at least 5% greater. For example, the amount of EbpA NTD in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of EbpA NTD in the sample of biological fluid obtained from the subject compared to the reference value may be increased at least 2-fold. For example, the amount of EbpA NTD in the sample compared to the reference value may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold.

In another aspect, the invention provides means to detect an EbpA-associated infection in a subject. An EbpA-associated infection is as described above in Section II.

Upon detection of an EbpA-associated infection, the subject may be treated via methods standard in the art for treating infection or the subject may be treated with compositions disclosed herein or a combination thereof. Such treatment methods may depend on the type and severity of the EbpA-associated infection, as well as the general condition of the patient. Standard treatment of infection consists primarily of antimicrobial therapy. Antimicrobial agents utilized for antimicrobial therapy may be as described herein.

In an embodiment, a method for monitoring EbpA-associated infection in a subject may be used to determine infection progression. In such an embodiment, a method of detecting EbpA NTD may be used to assess the risk of a subject at one point in time, then at a later time, the method of detecting EbpA NTD may be used to determine the change in risk of the subject over time. For example, the method of detecting EbpA NTD may be used on the same subject days, weeks, months or years following the initial determination of the amount of EbpA NTD. Accordingly, the method of detecting EbpA NTD may be used to follow a subject to determine when the risk of progressing to more severe infection is high thereby requiring treatment. Additionally, the method of detecting EbpA NTD may be used to measure the rate of infection progression. For example, a depressed amount of EbpA NTD may indicate an abatement of infection. Alternatively, an elevated amount of EbpA NTD may indicate infection progression. Levels may be monitored hourly, daily, weekly, monthly, etc. so as to track the progression/remission of an EbpA-associated infection such as during the period of hospitalization, the duration of treatment, and/or the duration of indwelling device.

In another embodiment, a method for monitoring EbpA-associated infection in a subject may also be used to determine the response to treatment. As used herein, patients who respond to treatment are said to have benefited from treatment. For example, a method to detect EbpA NTD may be performed on the biological sample of the subject prior to initiation of treatment, then at a later time, a method to detect EbpA NTD may be used to determine the response to treatment over time. For example, a method to detect EbpA NTD may be performed on the biological sample of the same subject days, weeks, months or years following initiation of treatment. Accordingly, a method to detect EbpA NTD may be used to follow a subject receiving treatment to determine if the subject is responding to treatment. If the amount of EbpA NTD remains the same or decreases, then the subject may be responding to treatment. If the amount of EbpA NTD increases, then the subject may not be responding to treatment. These steps may be repeated to determine the response to therapy over time.

For each aspect, the method generally comprises (i) obtaining a biological sample from a subject, (ii) measuring the amount of EbpA NTD in the sample using an anti-EbpA NTD antibody, and (iii) comparing the amount of EbpA NTD in the sample to a reference value. A greater amount of EbpA NTD in the sample compared to the reference value indicates the presence of an EbpA-associated infection. The amount of EbpA NTD may be a qualitative, a semi-quantitative or quantitative measurement. Suitable anti- EbpA NTD antibodies are described above, as are methods for measuring the amount of EbpA NTD in a biological sample. In a preferred embodiment, the biological sample is biological fluid selected from the group consisting of urine, sputum, blood, plasma, and serum.

III. Kits

In an embodiment, an antibody of the invention may be used in a kit to diagnose an EbpA-associated infection. In a specific embodiment, the EbpA-associated infection may be a CAUTI. Such kits are generally known in the art and commonly used to detect an antigen or microorganism of interest. These diagnostic kits will generally include the antibodies of the invention along with suitable means for detecting binding by that antibody such as would be readily understood by one skilled in this art. For example, the means for detecting binding of the antibody may comprise a detectable label that is linked to said antibody. Non-limiting examples of suitable labels include enzymes, radioactive isotopes, fluorescent compounds, chemical compounds, and bioluminescent proteins. These kits can then be used in diagnostic methods to detect the presence of an EbpA-associated infection wherein a sample is collected from a subject suspected of being infected by one or more EbpA-associated bacteria.

TABLE A

List of sequence referenced

| SEQ ID NO: | Sequence | Name |
|---|---|---|
| 1 | AWAGA | Altered MIDAS motif |
| 2 | DWSGS | WT MIDAS motif |
| 3 | PEKITV PENTKETNKN DSAPEKTEQP TATEEVTNPF AEARMAPATL RANLALPLIA PQYTTDNSGT YPTANWQPTG NQNVLNHQGN KDGSAQWDGQ TSWNGDPTNR TNSYIEYGGT GDQADYAIRK YARETTTPGL FDVYLNVRGN VQKEITPLDL VLVVDWSGSM NENNRIGEVQ KGVNRFVDTL ADSGITNNIN MGYVGYSSDG YNNNAIQMGP FDTVKNPIKN ITPSSTRGGT FTQKALRDAG DMLATPNGHK KVIVLLTDGV PTFSYKVSRV QTEADGRFYG TQFTNRQDQP GSTSYISGSY NAPDQNNINK RINSTFIATI GEAMALKQRG IEIHGLGIQL QSDPRANLSK QQVEDKMREM VSADENGDLY YESADYAPDI SDYLAKKAVQ ISGTVVNGKV VDPIAEPFKY EPNTLSMKSV GPVQVQTLPE VSLTGATINS NEIYLGKGQE IQIHYQV | EbpA NTD |
| 4 | DXSXS; wherein X is any amino acid | MIDAS motif sequence |
| 5 | MITDENDKTN INIELNLLNQ TEQPLQREIQ LKNAQFMDTA VIEKDGYSYQ VTNGTLYLTL DAQVKKPVQL SLAVEQSSLQ TAQPPKLLYE NNEYDVSVTS EKITVEDSAK ESTEPEKITV PENTKETNKN DSAPEKTEQP TATEEVTNPF AEARMAPATL RANLALPLIA PQYTTDNSGT YPTANWQPTG NQNVLNHQGN KDGSAQWDGQ TSWNGDPTNR TNSYIEYGGT GDQADYAIRK YARETTTPGL FDVYLNVRGN VQKEITPLDL VLVVDWSGSM NENNRIGEVQ KGVNRFVDTL ADSGITNNIN MGYVGYSSDG YNNNAIQMGP FDTVKNPIKN ITPSSTRGGT FTQKALRDAG DMLATPNGHK KVIVLLTDGV PTFSYKVSRV QTEADGRFYG TQFTNRQDQP GSTSYISGSY NAPDQNNINK RINSTFIATI GEAMALKQRG IEIHGLGIQL QSDPRANLSK QQVEDKMREM VSADENGDLY YESADYAPDI SDYLAKKAVQ ISGTVVNGKV VDPIAEPFKY EPNTLSMKSV GPVQVQTLPE VSLTGATINS NEIYLGKGQE IQIHYQVRIQ TESENFKPDF WYQMNGRTT QPLATAPEKV DFGVPSGKAP GVKLNVKKIW EEYDQDPTSR PDNVIYEISR KQVTDTANWQ TGYIKLSKPE NDTSNSWERK NVTQLSKTAD ESYQEVLGLP QYNNQGQAFN YQTTRELAVP GYSQEKIDDT TWKNTKQFKP LDLKVIKNSS SGEKNLVGAV FELSGKNVQT TLVDNKDGSY SLPKDVRLQK GERYTLTEVK APAGHELGKK TTWQIEVSEQ GKVSIDGQEV TTTNQVIPLE IENKFSSLPI RIRKYTMQNG KQVNLAEATF ALQRKNAQGS YQTVATQKTD TTGLSYFKIS EPGEYRMVEQ SGPLGYDTLA GNYEFTVDKY GKIHYAGKNI EENAPEWTLT HQNNLKPFDL TVHKKADNQT PLKGAKFRLT GPDTDIELPK DGKETDTFVF ENLKPGKYVL TETFTPEGYQ GLKEPIELII REDGSVTIDG EKVADVLISG EKNNQITLDV TNQAKVPLPE TGGIGRLWFY LIAISTFVIA GVYLFIRRPE GSV | EbpA full length |

TABLE A-continued

List of sequence referenced

| SEQ ID NO: | Sequence | Name |
|---|---|---|
| 6 | CGCGGATCCATAACAGTAGAGGATTCTGCTAAA | ALFM01 |
| 7 | CTAGCTAGCTTAACCAGTTTCAGGTAAAGGAACC | ALFM02 |
| 8 | CCGGATATCTCATCATCATCGTACTTGATAATGAATTTGAAT | ALFM51 |
| 9 | CCGGATATCAGGGGTTAAAAGAACCAATCGAATTAATAA | ALFM52 |
| 10 | GCGGGATCCATGAATGGTCGGACAACGTTTCAGCC | HVN114 |
| 11 | CCGTCGACTTACAAGCGTCCTATGCCACCAGTTTCAGG | HVN117 |

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.
Introduction to the Examples.

Catheter-associated urinary tract infections (CAUTIs) are the most common cause of hospital-acquired infections with the incidence of conversion from sterile urine to bacteriuria occurring at the rate of 3 to 10% per day (1-3). Furthermore, 3% of all patients with chronic indwelling urinary catheters will develop bacteremia within 30 days (4), and virtually all patients will develop an infection once the catheter has been in place >30 days (1-3). Drug resistance has become a critical concern for treatment of CAUTIs, particularly for infections caused by Gram-positive bacteria in the genus Enterococcus, which account for 15% of all CAUTIs (5). Because of their tolerance to heat, aseptic solutions, and intrinsic antibiotic resistance, enterococci have been difficult to control in the hospital environment (6-10). Of concern, their intrinsic resistances have been augmented by the emergence of strains resistant to nearly all antibiotics commonly used in treatment, including vancomycin. Treatment now has few options and often requires frequent removal and replacement of the catheter (1, 3, 11). Thus, the development of alternative therapies and prophylactic strategies is required.

Figure 6A:
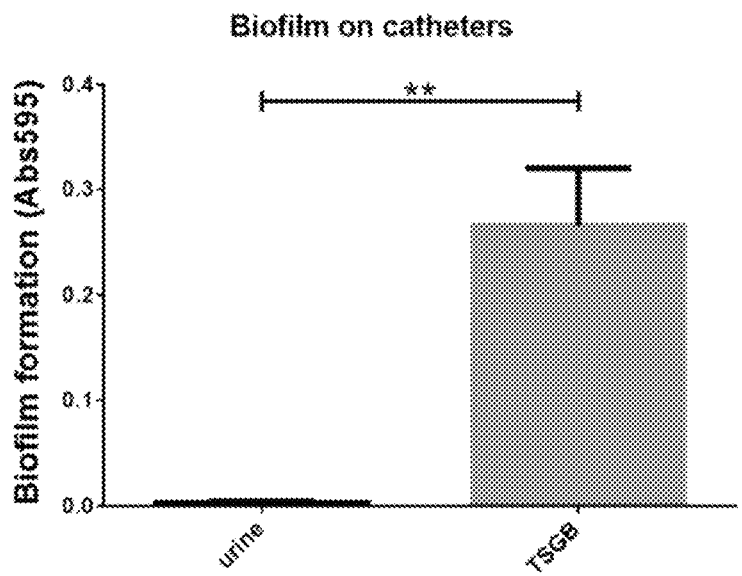
FIG. 6A and FIG. 6B depict graphs of *E. faecalis* OG1 RF growth and biofilm formation in urine.

A limiting factor for the development of new therapies has been the relatively poor understanding of the molecular details of enterococcal CAUTI pathogenesis. However, the ability of Enterococcus faecalis to cause CAUTIs is known to derive from its capacity to form biofilms on catheters, which allows the bacterium to persist in the bladder despite a robust inflammatory response (12-14). In animal models of CAUTIs, a long hair-like extracellular fiber known as the endocarditis- and biofilm-associated pilus (Ebp) has been shown to contribute to both biofilm formation and disease (15-18). A member of the sortase-assembled pilus family, the Ebp pilus is a heteropolymer composed of three subunits: the major shaft subunit (EbpC) and the minor subunits at the base (EbpB) and tip (EbpA) of the fiber (19, 20). The enzyme sortase C (SrtC) catalyzes the formation of isopeptide bonds between EbpA to EbpC and among the EbpC subunits that make up the shaft and finally between the EbpC shaft and EbpB. Sortase A (SrtA) covalently attaches the mature fiber to peptidoglycan of the bacterial cell wall via EbpB (19, 20). In a murine model of CAUTIs, E. faecalis mutants lacking the EbpA tip protein are highly attenuated, as are strains that express a mutant EbpA containing a point mutation in the metal ion-dependent adhesion site (MIDAS) motif located in the von Willebrand factor A (vWA) domain of EbpA (18). In the same mouse model in the absence of the implanted catheter, E. faecalis is highly attenuated (18). Thus, on the basis of its location at the fiber tip and its importance in CAUTI pathogenesis, we hypothesized that EbpA is an adhesin that promotes attachment to the catheter surface. Paradoxically, when tested in vitro before implantation, wild-type E. faecalis (which expresses EbpA) was not able to adhere to the catheter and thus was unable to form a biofilm (FIG. 6A). Thus, the nature of EbpA-host receptor interactions in catheter-associated biofilm formation and whether this interaction could be targeted for the development of new therapeutics are unknown.

Here, we elucidated how E. faecalis exploits the host inflammatory response caused by catheter implantation to establish and persist during CAUTIs. We found that host fibrinogen is released into the bladder upon catheterization as part of the host inflammatory response and subsequently accumulates in the bladder and becomes deposited on the implanted catheter. We discovered that EbpA's N-terminal domain mediated binding to fibrinogen. This resolved the paradoxical finding that the catheter was required for CAUTIs, even though enterococcus was unable to bind to the catheter material in vitro when grown in human urine. The N-terminal domain of EbpA is composed of a MIDAS-containing vWA domain, which is important for adhesion to extracellular matrix (ECM) proteins, and a fibrinogen-binding SdrG-like domain. The fibrinogen-binding interaction was found to be crucial during E. faecalis CAUTIs and was abolished by a point mutation in the MIDAS motif. Further, we found that E. faecalis uses fibrinogen for growth, thus enhancing biofilm formation on the catheter. On the basis of these findings, we developed an EbpA-based vaccine that protected mice from E. faecalis infection by inhibiting the interaction between EbpA and fibrinogen.

Example 1

The MIDAS motif in EbpA is Necessary for E. faecalis Biofilm Formation

We first investigated the role of EbpA in biofilm formation using a tryptic soy broth supplemented with 0.25% glucose (TSBG) standard culture medium and an in vitro polyvinyl chloride (PVC) coverslip biofilm assay. We measured biofilm formation of a well-characterized collection of E. faecalis mutants constructed in the OG1 RF strain (18, 19) that lacked either EbpA (ΔEbpA, ΔEbpAB, or ΔEbpABCΔSrtC), lacked the ability to attach the pilus and other sortase substrates to the cell wall (ΔSrtA), or expressed EbpA with an altered MIDAS motif designated as EbpA$^{AWAGA}$ (SEQ ID NO:1), based on alanine substitution mutations of three residues predicted to coordinate a metal ion (underlined) in the five-residue motif (Asp$^{315}$-Trp-Ser$^{317}$-Gly-Ser$^{319}$; SEQ ID NO:2). These EbpA-altered mutants were compared to a mutant that expresses EbpA on the cell surface in the absence of the pilus shaft (ΔEbpC) (19) and to wild-type E. faecalis OG1 RF. All mutants lacking a wild-type surface-attached EbpA were defective for biofilm formation compared to E. faecalis OG1 RF when analyzed after 48 hours of incubation under static conditions (FIG. 1A). This defect was attributed to the function of EbpA because the mutants lacking only EbpA or having the point mutations in the EbpA MIDAS motif (EbpA$^{AWAGA}$ (SEQ ID NO:1)) were as defective in forming biofilms as any of the other mutants (ΔEbpA, FIG. 1A). In contrast, formation of an EbpA-dependent biofilm did not require the major shaft protein (ΔEbpC) (FIG. 1A). These data indicate that like CAUTI pathogenesis (18), EbpA facilitates biofilm formation by a mechanism that requires its MIDAS motif; however, the mechanism by which EbpA facilitates TSBG PVC biofilm formation is unknown.

Example 2

The N-terminal Domain of EbpA is Required for Fibrinogen Binding

Figure 1C:
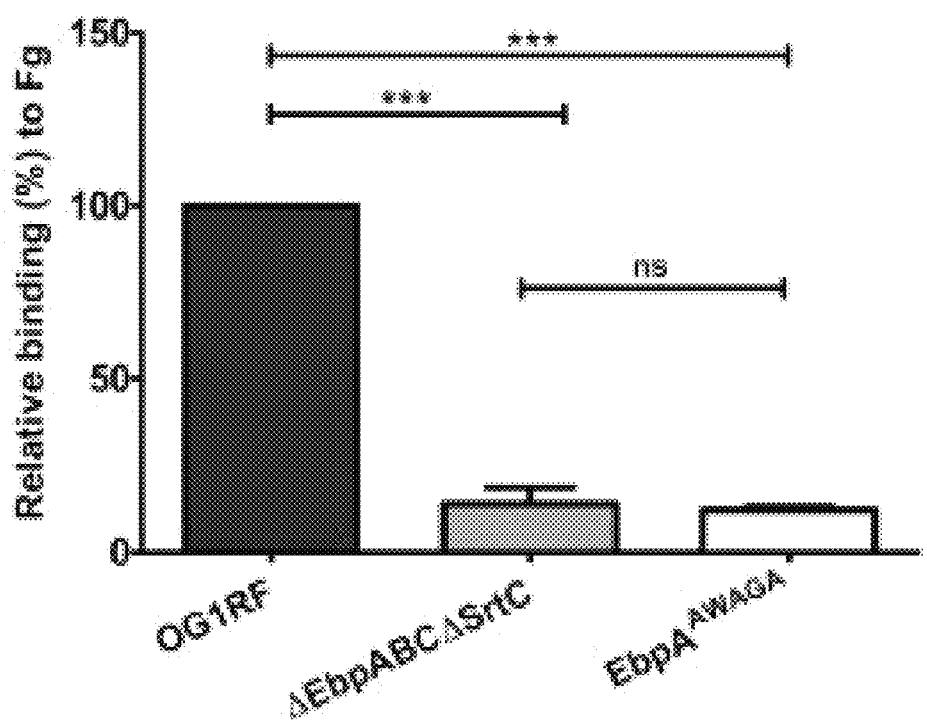
Figure 1D:
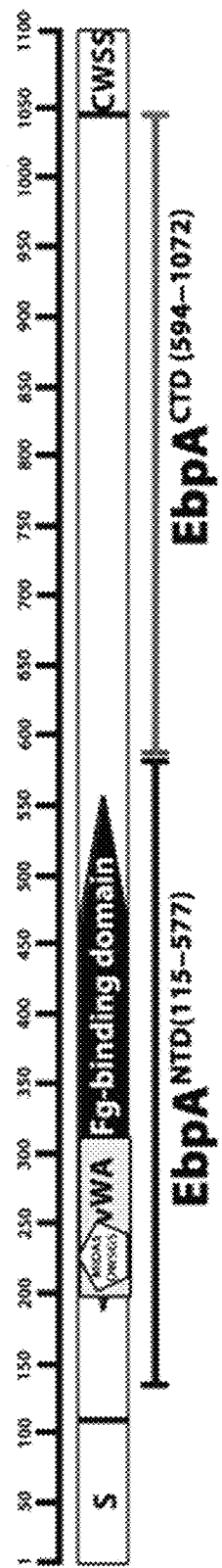
Figure 1E:
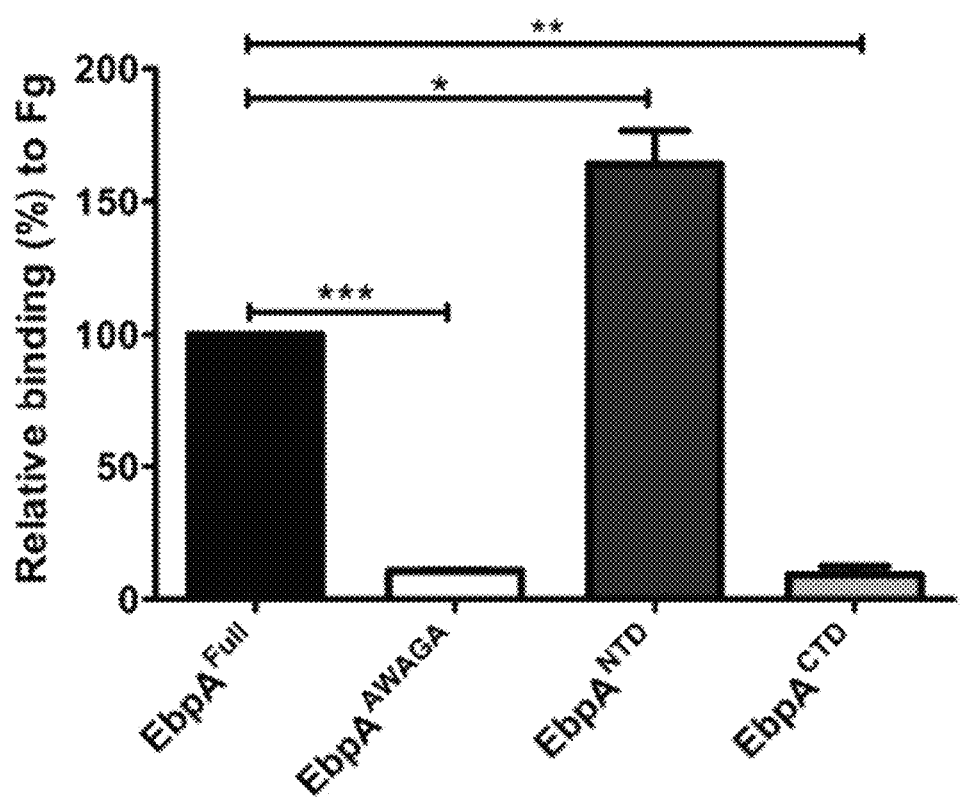
Figure 7A:
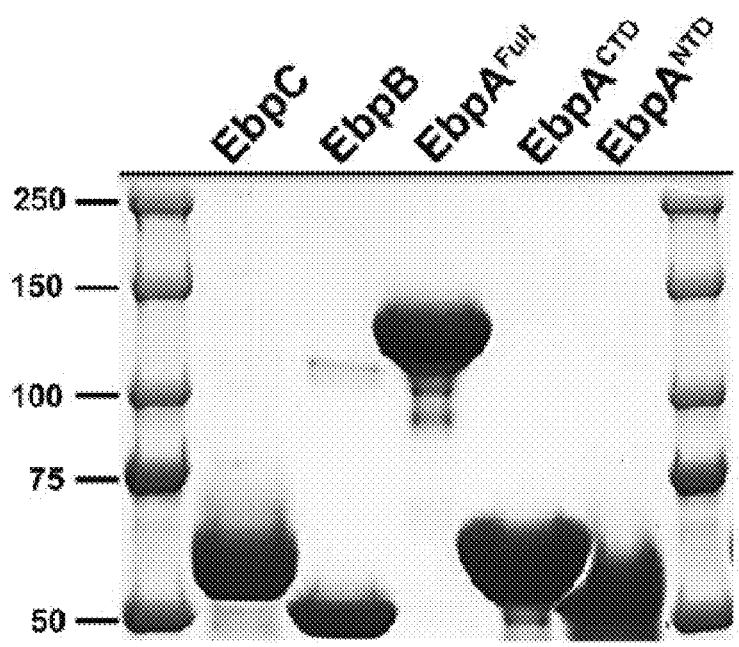
FIG. 7A and FIG. 7B depict Coomassie stained gels of purified Ebp subunits.
Figure 7B:
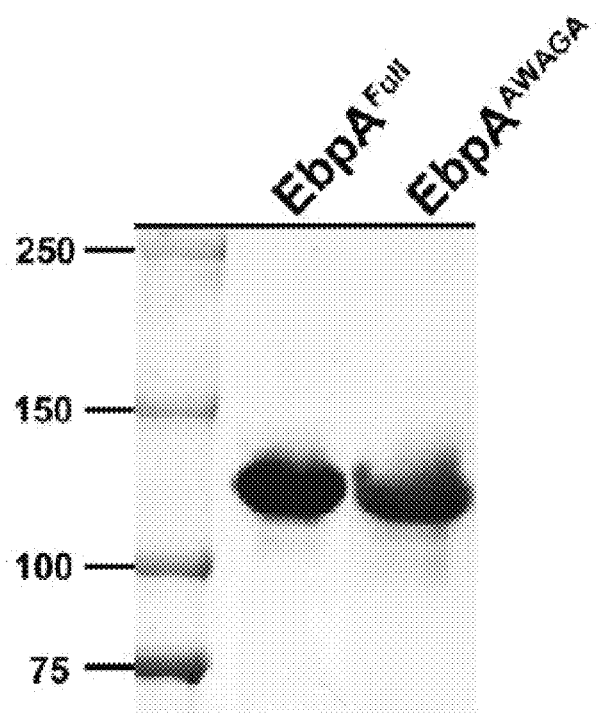
Figure 8A:
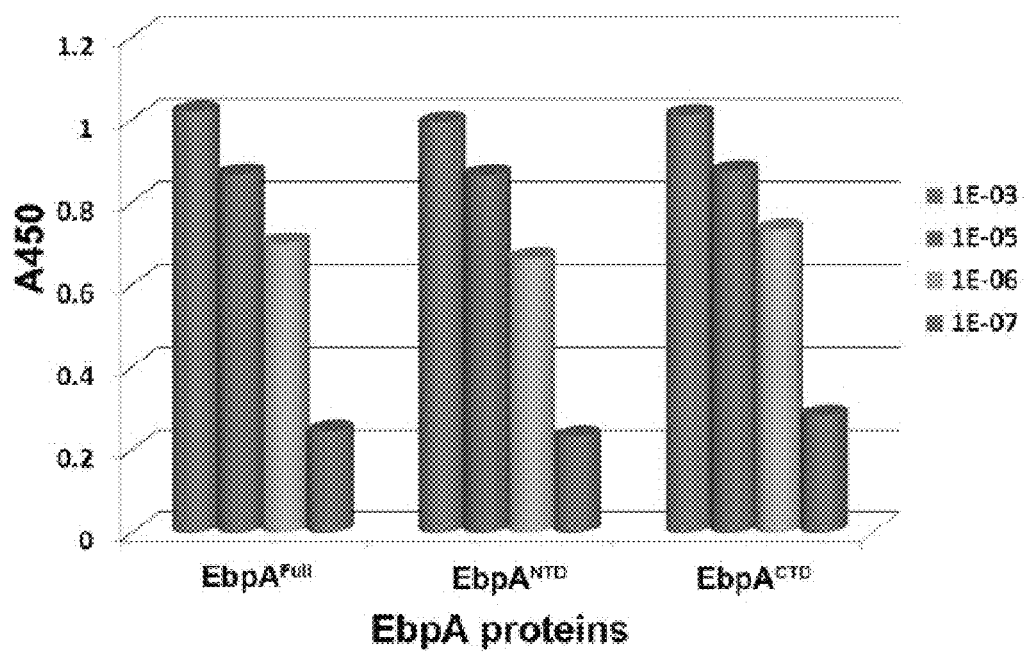
FIG. 8A, FIG. 8B and FIG. 8C depict graphs showing reactivity of polyclonal mouse anti-EbpA antibodies against EbpA variant proteins. Titers of anti-EbpA$^{Full}$ (FIG. 8A), anti-EbpA$^{NTD}$ (FIG. 8B), and anti-EbpA$^{CTD}$ (FIG. 8C) were analyzed by pooling samples from 10 individual mice of each immunization treatment and diluted 1:100 before serial dilution.
Figure 8B:
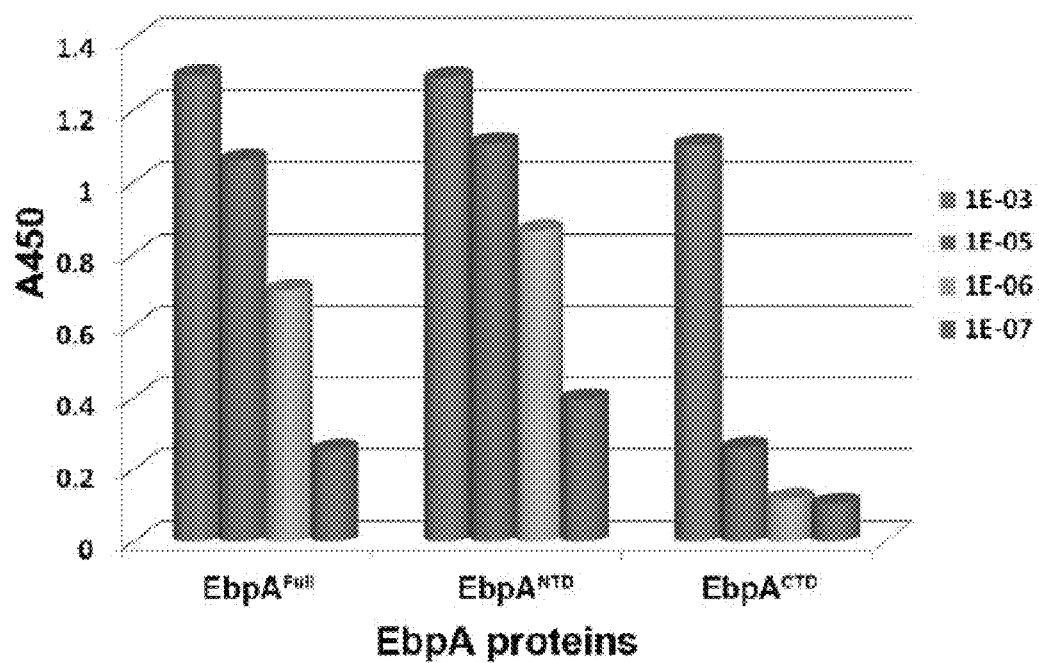
Figure 8C:
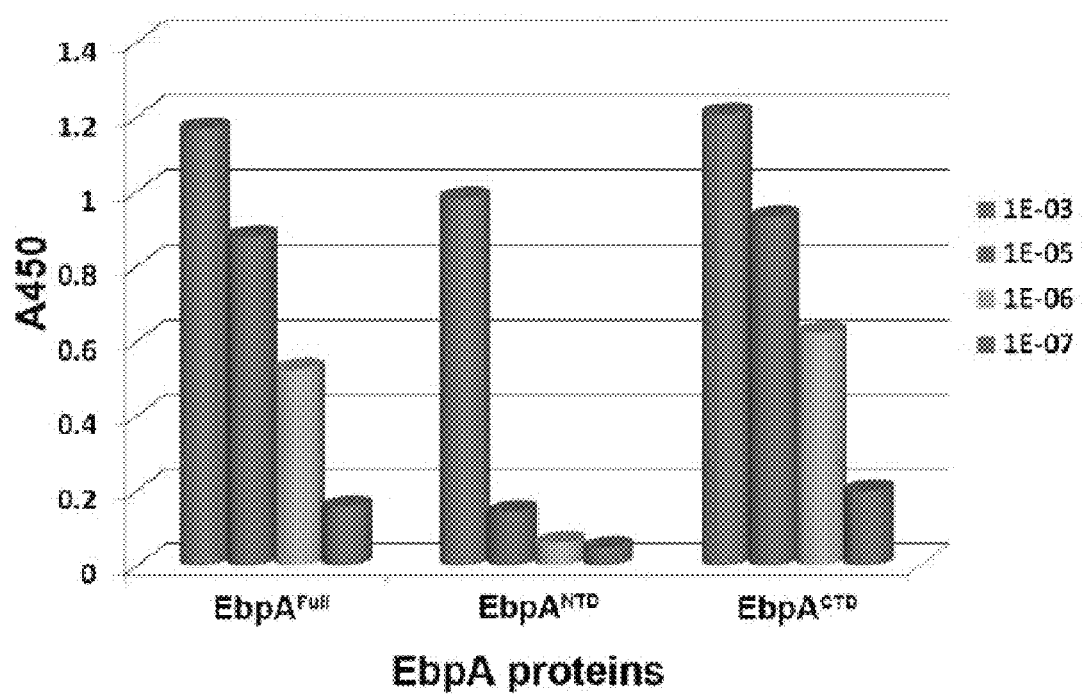

The Ebp pilus has been implicated in both collagen and fibrinogen binding (16), suggesting that these ECM proteins are possible receptors for EbpA. We investigated this hypothesis by comparing wild-type E. faecalis OG1 RF to a pilus-deficient mutant (ΔEbpABCΔSrtC) and an EbpA MIDAS mutant (EbpA$^{AWAGA}$ (SEQ ID NO:1)) for their ability to bind to surfaces coated with collagen I or fibrinogen using an enzyme-linked immunosorbent assay (ELISA). This analysis revealed that whereas no strain had a defect for binding to collagen I (FIG. 1 B), the loss of pili or presence of point mutations in the EbpA MIDAS motif significantly reduced binding to fibrinogen (P<0.0005) (FIG. 1C). A computational search for known conserved domains predicted that the N-terminal domain of EbpA (200 to 577 amino acids) contains a region (99.96% confidence) that resembles blood clotting factor, which includes the MIDAS-containing vWA domain (FIG. 1D). Because blood clotting function is a well-studied feature of fibrinogen-binding proteins such as ClfB, we hypothesized that the N-terminal domain of EbpA is implicated in fibrinogen binding. To test this, genetic constructs encoding truncated EbpA corresponding to its N-terminal (EbpA$^{NTD}$, residues 115 to 577) and C-terminal (EbpA$^{CTD}$, residues 594 to 1077) domains were designed (FIG. 1D). Each truncated version was found to be stable when expressed in Escherichia coli (FIG. 7). Purified EbpA$^{CTD}$ and EbpA$^{NTD}$ were compared to wild-type EbpA (EbpA$^{Full}$) and the defective MIDAS EbpA$^{AWAGA}$ (SEQ ID NO:1) (FIG. 7) for their ability to bind to fibrinogen, as measured by ELISA. To detect all species of EbpA, we used a polyclonal mouse anti-EbpA$^{Full}$ that recognized in similar level Full, NTD, and CTD EbpA proteins (FIG. 8). Consistent with our model, we found that EbpA$^{NTD}$ bound to fibrinogen at a level equivalent to EbpA$^{Full}$, whereas neither EbpA$^{CTD}$ nor EbpA$^{AWAGA}$ (SEQ ID NO:1) demonstrated any ability to bind to fibrinogen (FIG. 1E).

Example 3

Figure 2A:
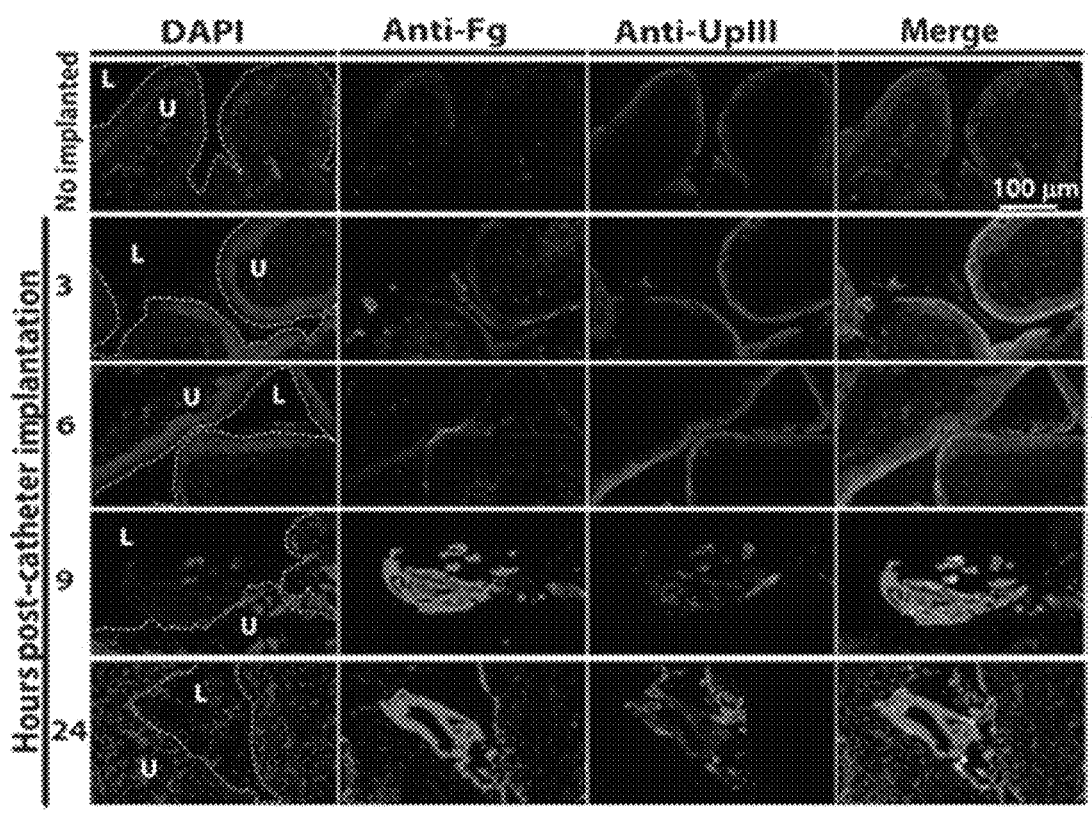
FIG. 2A and FIG. 2B depict images showing the time course of fibrinogen release and deposition on catheters implanted in mouse bladders. Mice were implanted with catheters and challenged by 1×10$^7$ CFU *E. faecalis* OG1 RF. At the indicated time points after infection, bladder tissue (FIG. 2A) and catheters (FIG. 2B) were recovered and subjected to analysis by immunofluorescence using antibody staining to detect fibrinogen (anti-Fg; green). Samples were costained with antibody to detect uroplakin III (anti-UpIII; red) or with DAPI (blue) to delineate the urothelium and cell nuclei, respectively (representative images). The white broken line separates the bladder lumen (L) from the urothelium surface (U).
Figure 2B:
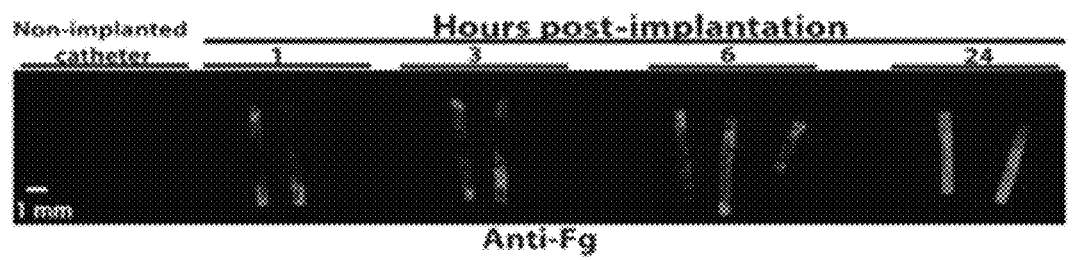

E. faecalis OG1RF Interacts with Released Fibrinogen in the Catheterized Mouse Bladder Urinary catheterization is associated with inflammation and edema even in the absence of infection (12,22-24). Given that fibrinogen is a prominent component of inflammatory exudates (25, 26), we investigated whether fibrinogen might be present in the mouse bladder when catheterized. For this experiment, a 5-mm platinum-cured silicone tube was transurethrally implanted into the mouse bladder lumen to mimic catheterization. Paraffin-embedded sections of bladder tissue were prepared from mice that were sacrificed at 3, 6, 9, and 24 hours after catheter implantation. The sections were stained for fibrinogen (anti-fibrinogen antiserum), uroplakin III (anti-UpIII to delineate the superficial umbrella cells) (27), and 4',6-diamidino-2-phenylindole (DAPI) to visualize cell nuclei. Analysis of nonimplanted bladders by immunofluorescence microscopy revealed an intact urothelium with no detectable fibrinogen at any time point. However, upon catheter implantation, fibrinogen was detected in the lumen of the bladder at 3 and 6 hours after catheter implantation, although the urothelium appeared intact. By 9 and 24 hours after catheter implantation, the urothelium appeared compromised with significant accumulation of fibrinogen (FIG. 2A). In addition, direct immunofluorescence staining of recovered catheters as early as 1 hour after catheter implantation revealed extensive deposition of fibrinogen, which increased in a time-dependent fashion (FIG. 2B).

Figure 3A:
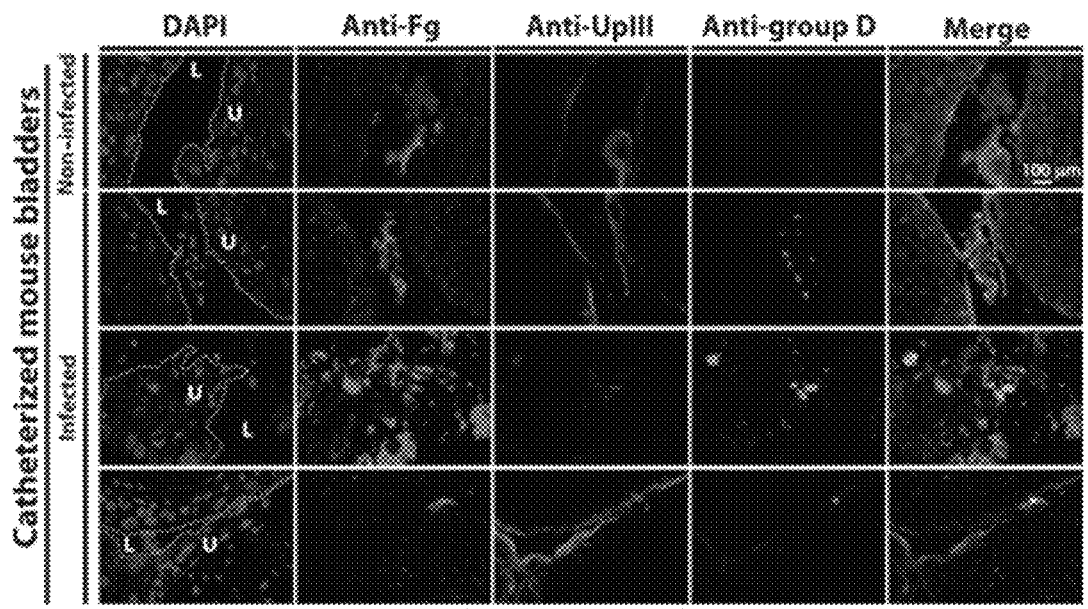
FIG. 3A and FIG. 3B depict images showing Colocalization of *E. faecalis* EbpA with fibrinogen in catheter-implanted mouse bladders. Catheter-implanted mice were challenged with the indicated *E. faecalis* OG1 RF (infected) or were unchallenged (uninfected). Bladder tissue (FIG. 3A) and catheters (FIG. 3B) were analyzed after 24 hours of implantation by immunofluorescence using antibody staining to detect fibrinogen (anti-Fg; green) and *E. faecalis* (anti-group D; pink). Antibody staining for uroplakin III (anti-UpIII; red) or with DAPI (blue) delineated the urothelium and cell nuclei, respectively.
Figure 3B:
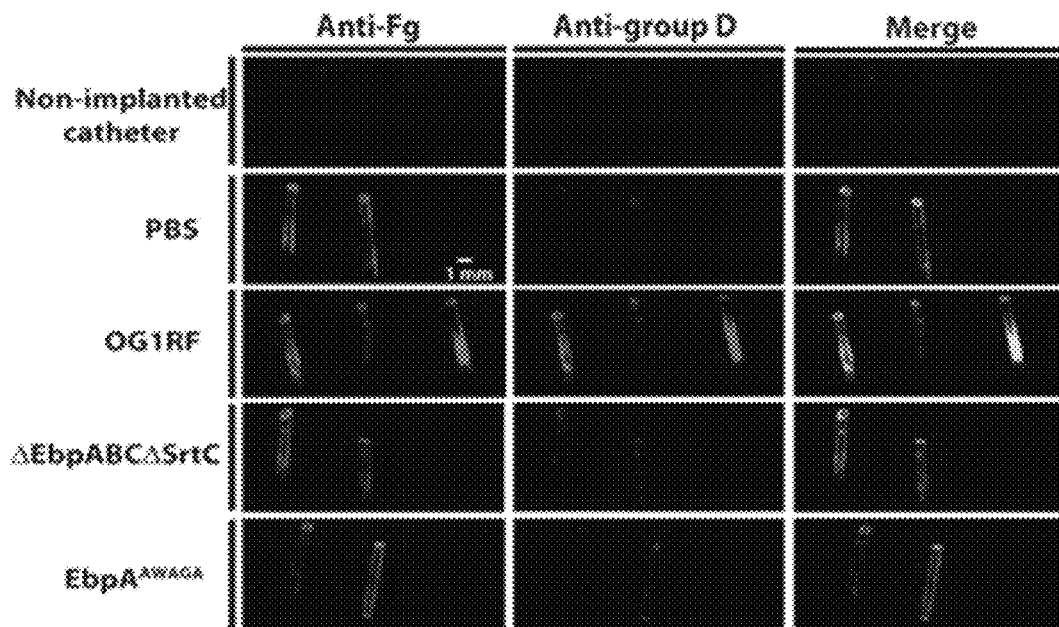

To further understand the interaction between E. faecalis and fibrinogen during CAUTIs, implanted animals were then challenged with 1×10$^7$ colony-forming units (CFU) of E. faecalis OG1 RF, and 24 hours after implantation, catheters and bladder tissue were recovered and stained for fibrinogen and E. faecalis (goat anti-fibrinogen and rabbit anti-streptococcal group D antigen, respectively). Examination by immunofluorescence microscopy revealed that the wild-type strain colocalized with fibrinogen on both the catheter and the urothelium (OG1 RF; FIG. 3A and FIG. 3B). In contrast, the mutant lacking pili (ΔEbpABCΔSrtC) and a MIDAS motif mutant (EbpA$^{AWAGA}$ (SEQ ID NO:1)) were not detected on either surface (FIG. 3B). These data reveal that EbpA-fibrinogen interactions are a critical component of E. faecalis CAUTIs.

Example 4

Figure 4A:
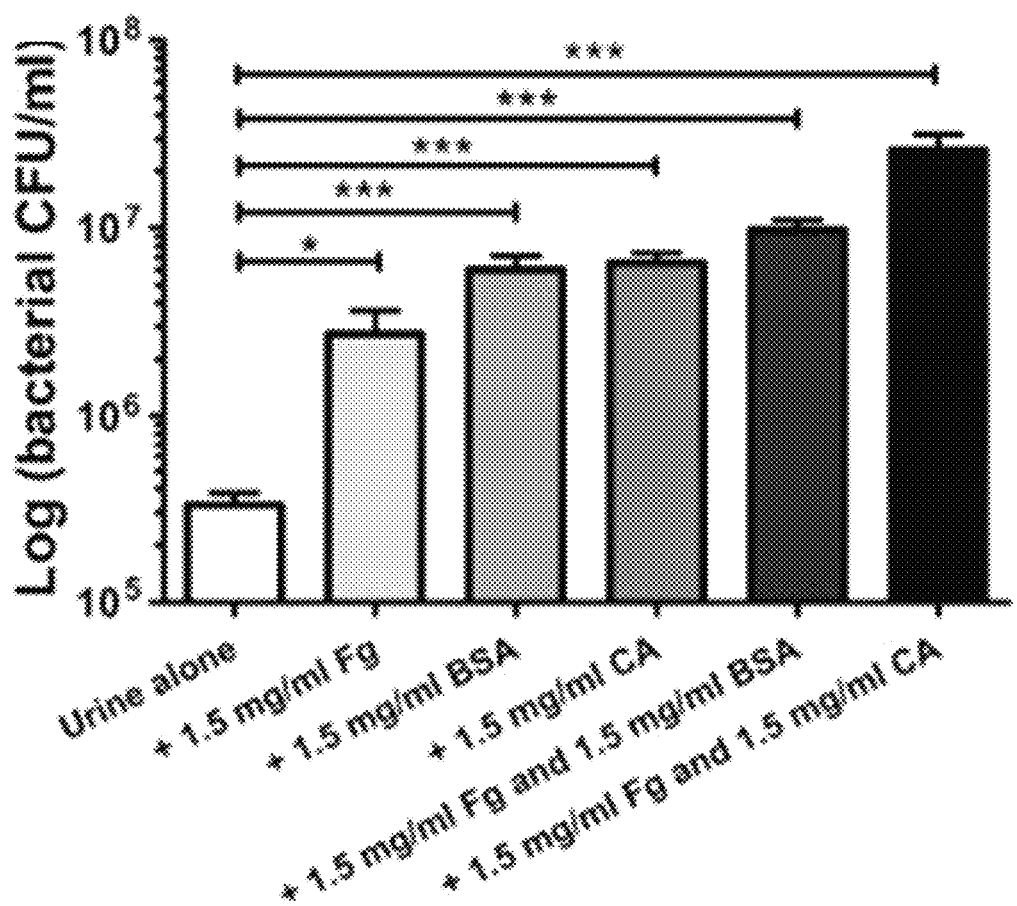
FIG. 4A, FIG. 4B, FIG. 4C, FIG. 4D, FIG. 4E, FIG. 4F, FIG. 4G, FIG. 4H and FIG. 4A depict graphs and images showing that *E. faecalis* OG1 RF biofilm formation in human urine requires fibrinogen. Bacterial growth was determined by the number of CFU after 24 hours (or otherwise indicated) of culture in human urine alone or in urine supplemented with the indicated concentrations of fibrinogen (Fg), bovine serum albumin (BSA), or casamino acids (CA).
Figure 4B:
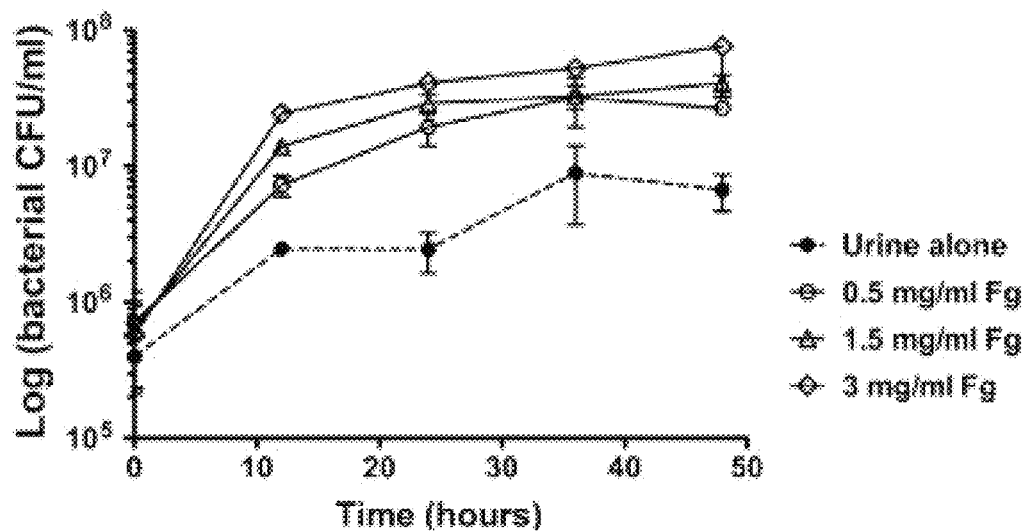
Figure 4C:
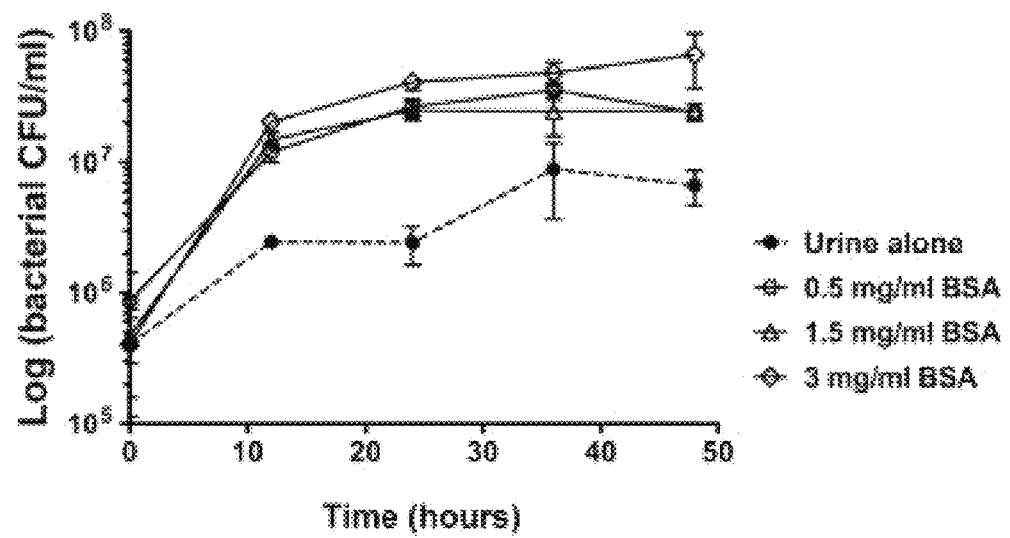
Figure 4D:
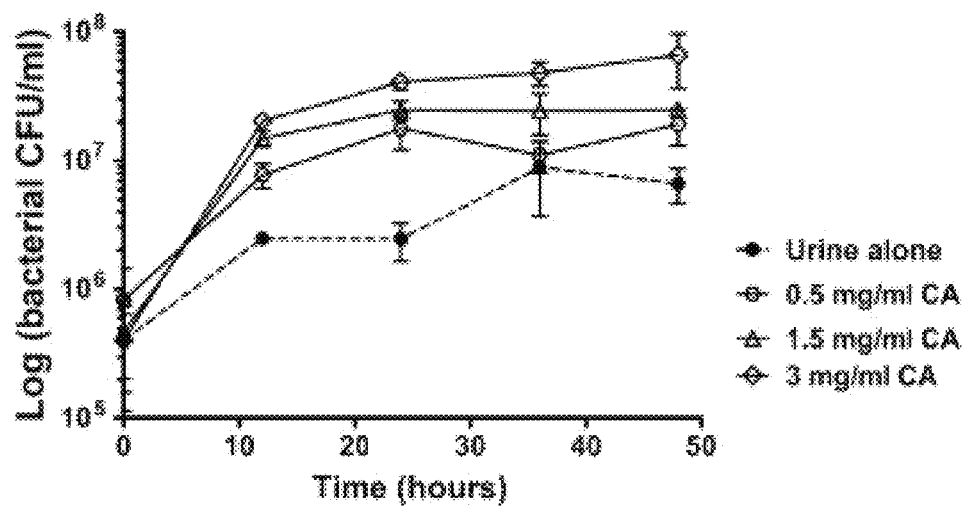
Figure 4E:
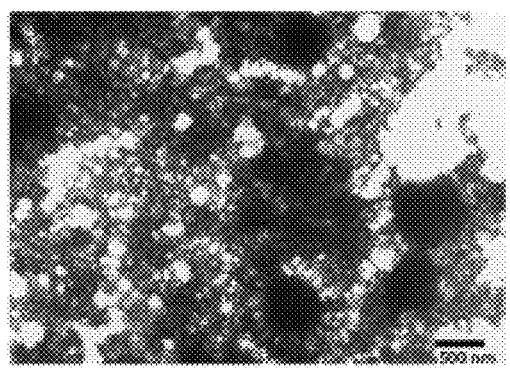
Figure 4F:
Figure 4G:
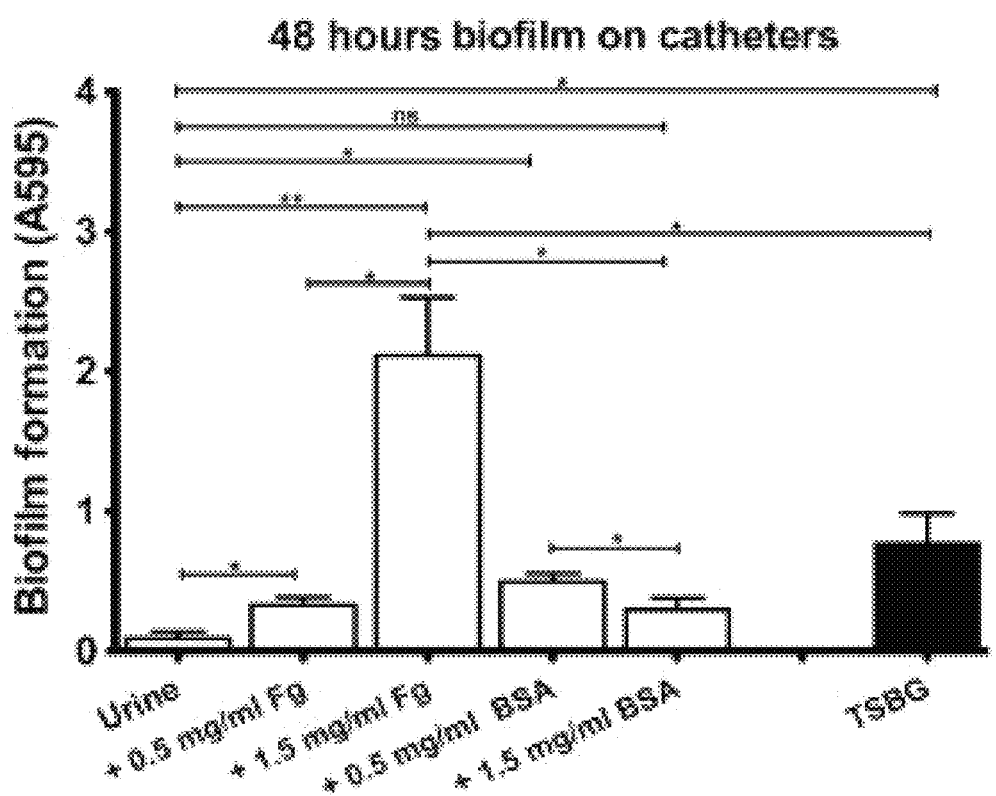
Figure 4H:
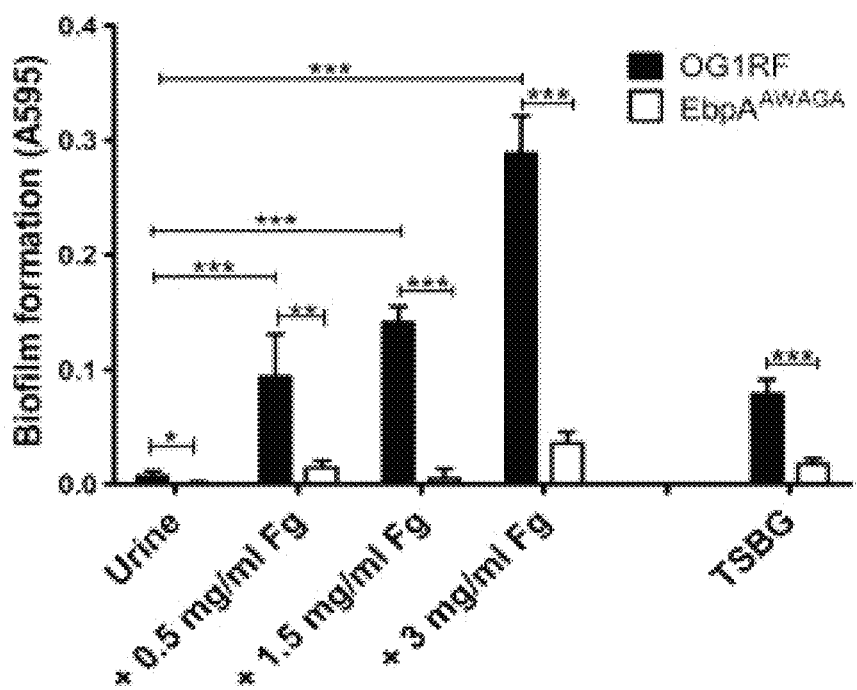
Figure 4I:
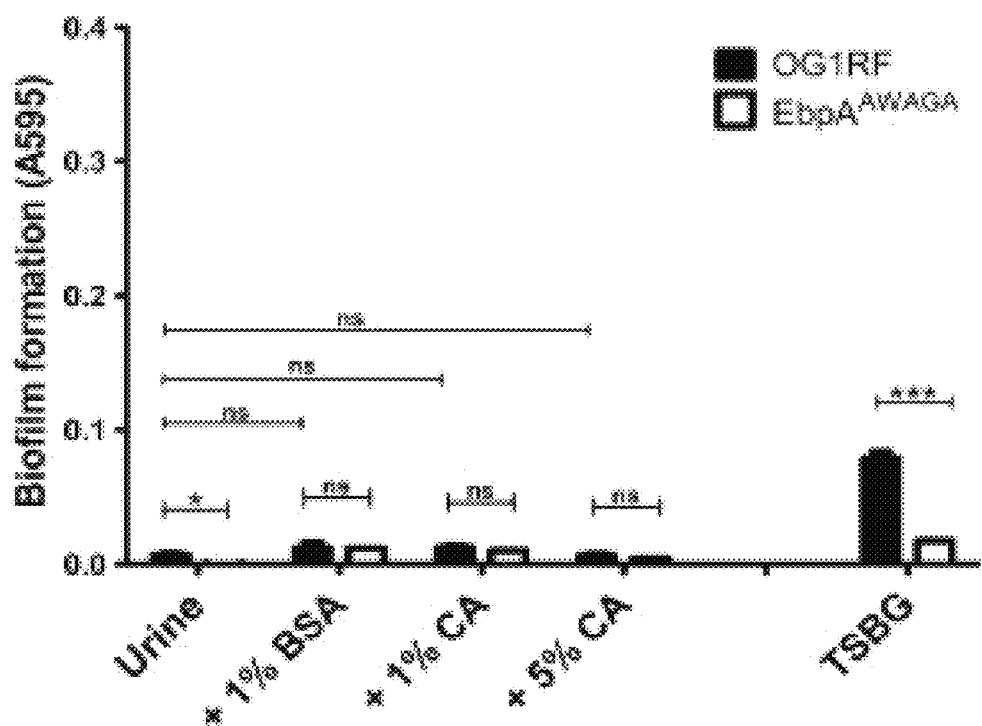
Figure 6B:
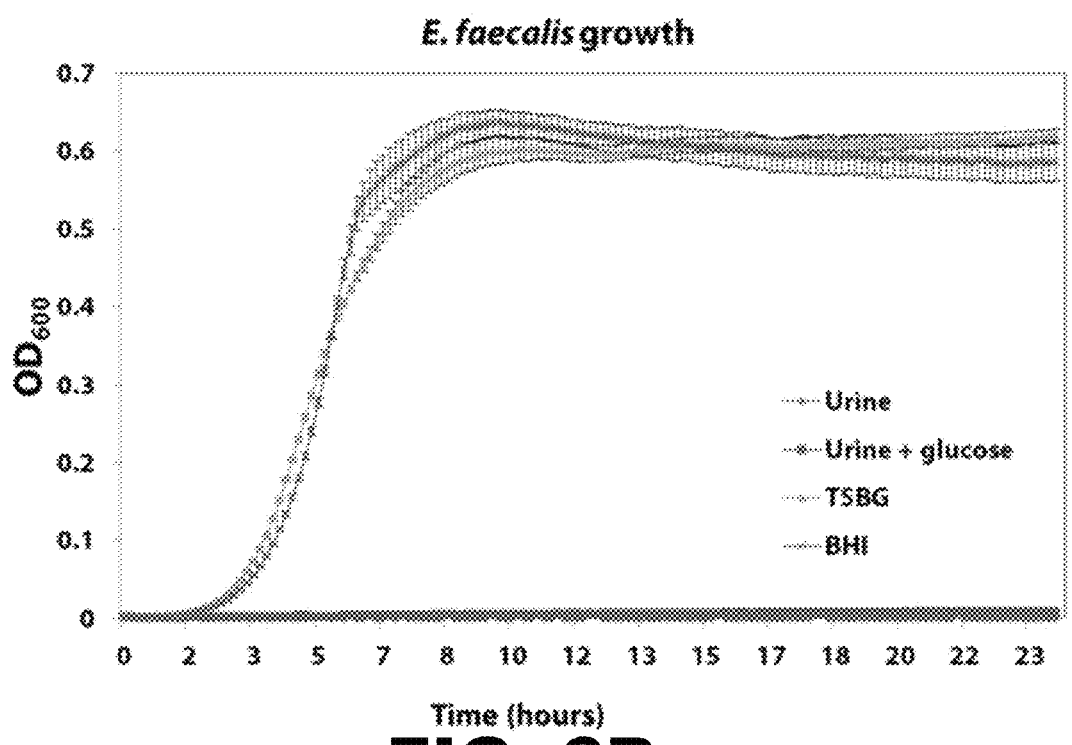
Figure 9A:
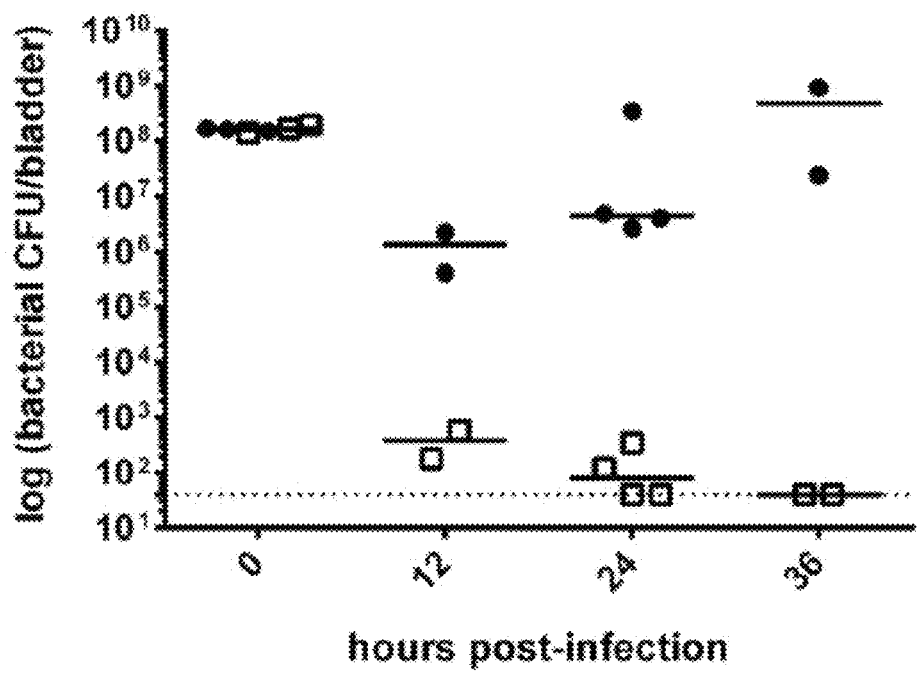
FIG. 9A and FIG. 9B depict graphs showing *E. faecalis* replication in bladder and catheter, respectively, in a murine model of CAUTIs. The ability of *E. faecalis* to replicate during CAUTI was evaluated by monitoring the segregation of plasmid that confers resistance to erythromycin (pJRS233) that cannot replicate at temperatures above 30° C. Catheter-implanted mice were infected with 1×10$^7$ CFU of *E. faecalis* OG1 RF (pJRS233) and bacterial burdens in bladder (FIG. 9A) or on catheters (FIG. 9B) determined by plating on BHI medium supplemented with (□) or without (●) 10 µg/ml of erythromycin.
Figure 9B:
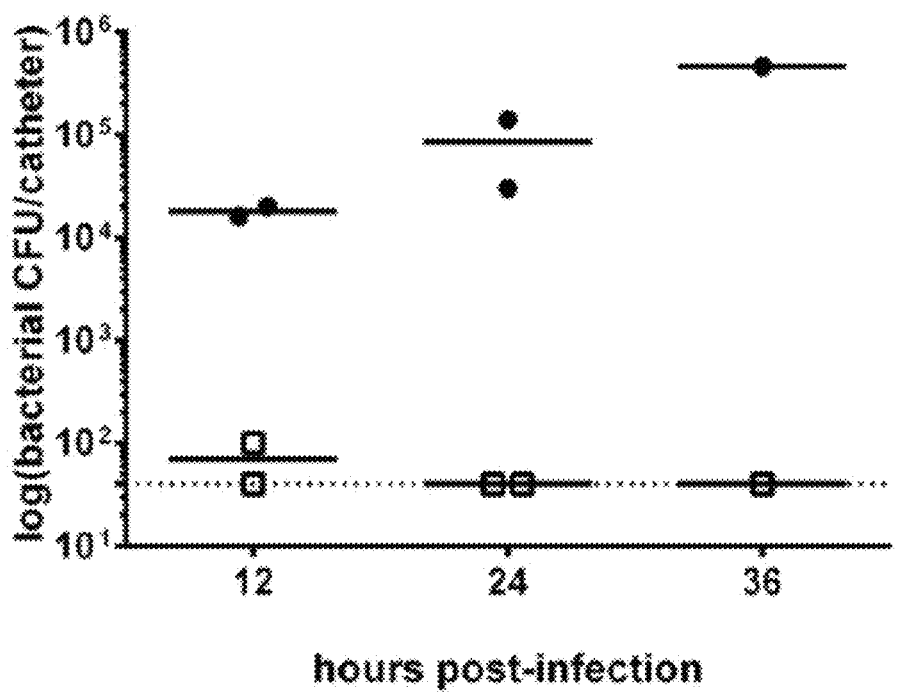

Fibrinogen is a Key Element of E. faecalis OG1RF Growth and Biofilm Formation in Urine To determine the importance of EbpA-fibrinogen interactions on catheter biofilm formation in the bladder, biofilm formation was examined on catheters in vitro in the presence of human female urine. Paradoxically, E. faecalis OG1 RF grew poorly (0.5 log from the initial inoculum ~5×10$^5$ CFU/ml) in urine (FIG. 4A) and failed to form catheter-associated biofilms even when supplemented with glucose as an additional energy source (FIG. 6B). Because urine is the principal host component that E. faecalis is exposed to during CAUTIs, this raised the question whether E. faecalis actively replicates during murine CAUTIs or if the disease is the result of nonreplicating persistence of the original inoculum. This was tested using a method that monitors the segregation of a plasmid that cannot replicate at in vivo temperature (28). In actively dividing cells, the nonreplicating plasmid is asymmetrically passed to daughter cells and is lost from the population over time. This analysis revealed that the percentage of bacterial cells maintaining the plasmid during CAUTIs dropped to nearly undetectable levels by 24 hours after infection in the bladder (FIG. 9), as would be expected for rapidly dividing cells. In vitro, when urine was supplemented with fibrinogen, we found that E. faecalis OG1 RF consumed the fibrinogen to grow (FIG. 4E and FIG. 4F) and formed catheter-associated biofilms (FIG. 4A and FIG. 4B), thus resolving the paradox. BSA or casamino acids also supported growth (FIG. 4A, FIG. 4C, and FIG. 4D), but only fibrinogen was capable of promoting biofilm formation on catheters (FIG. 4G). Furthermore, similar to CAUTI biofilm formation in vivo (FIG. 3B), the ability to form biofilms in vitro (96-well polystyrene microplates) in fibrinogen-supplemented urine was lost in the mutant in which the MIDAS motif of EbpA was rendered nonfunctional (EbpA$^{AWAGA\ (SEQ\ ID\ NO:1)}$; FIG. 4H and FIG. 4I).

Example 5

Immunization with EbpA$^{NTD}$ Protected Mice from E. faecalis CAUTIs

Figure 5A:
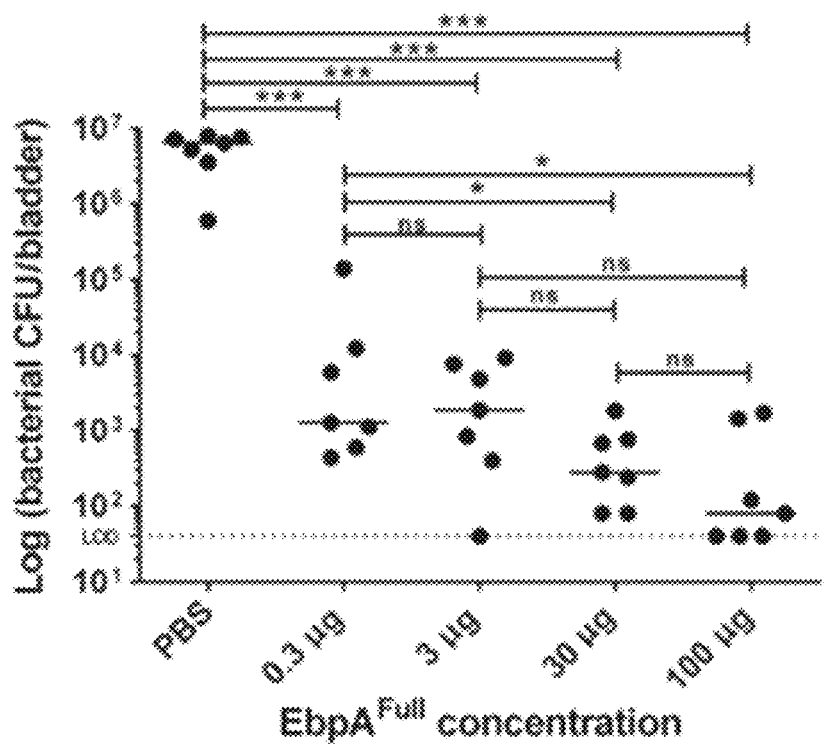
FIG. 5A, FIG. 5B, FIG. 5C, FIG. 5D, FIG. 5E and FIG. 5F depict graphs and images showing EbpA adhesin-based vaccine protects mice from *E. faecalis* CAUTIs. Mice were immunized and received two booster immunizations with the indicated doses of the various Ebp proteins (EbpB, EbpC, EbpA$^{Full}$, EbpA$^{NTD}$, and EbpA$^{CTD}$). Four weeks after the final immunization, mice were implanted with catheters and challenged with 1×10$^7$ CFU of *E. faecalis* OG1 RF. After 24 hours of infection, bacterial burdens in bladder tissue (FIG. 5A and FIG. 5D) or recovered catheters (FIG. 5B and FIG. 5E) were quantitated as the number of CFU recovered.
Figure 5B:
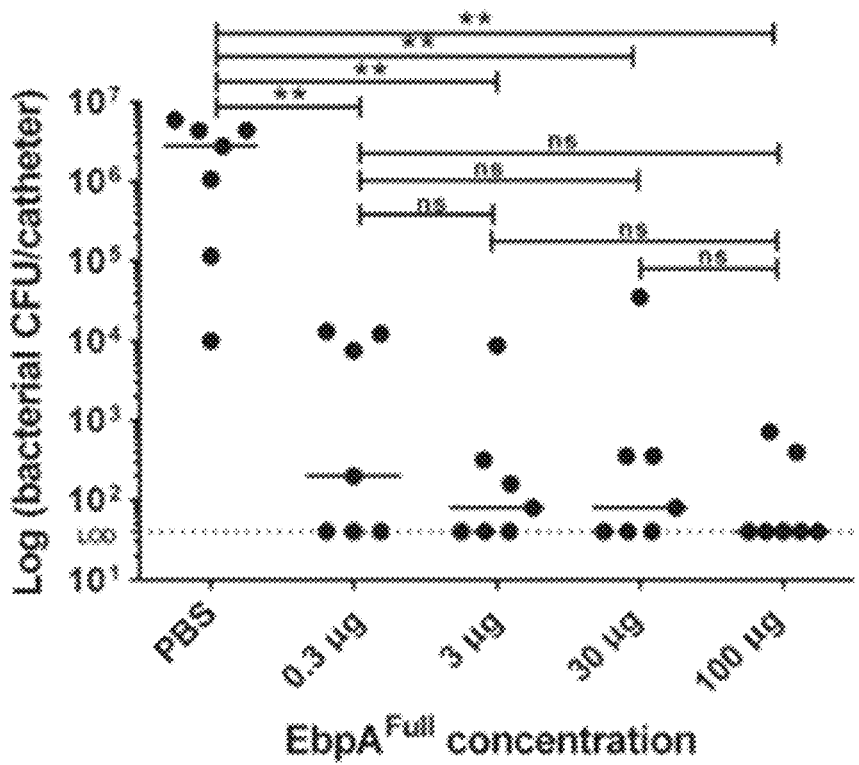
Figure 5C:
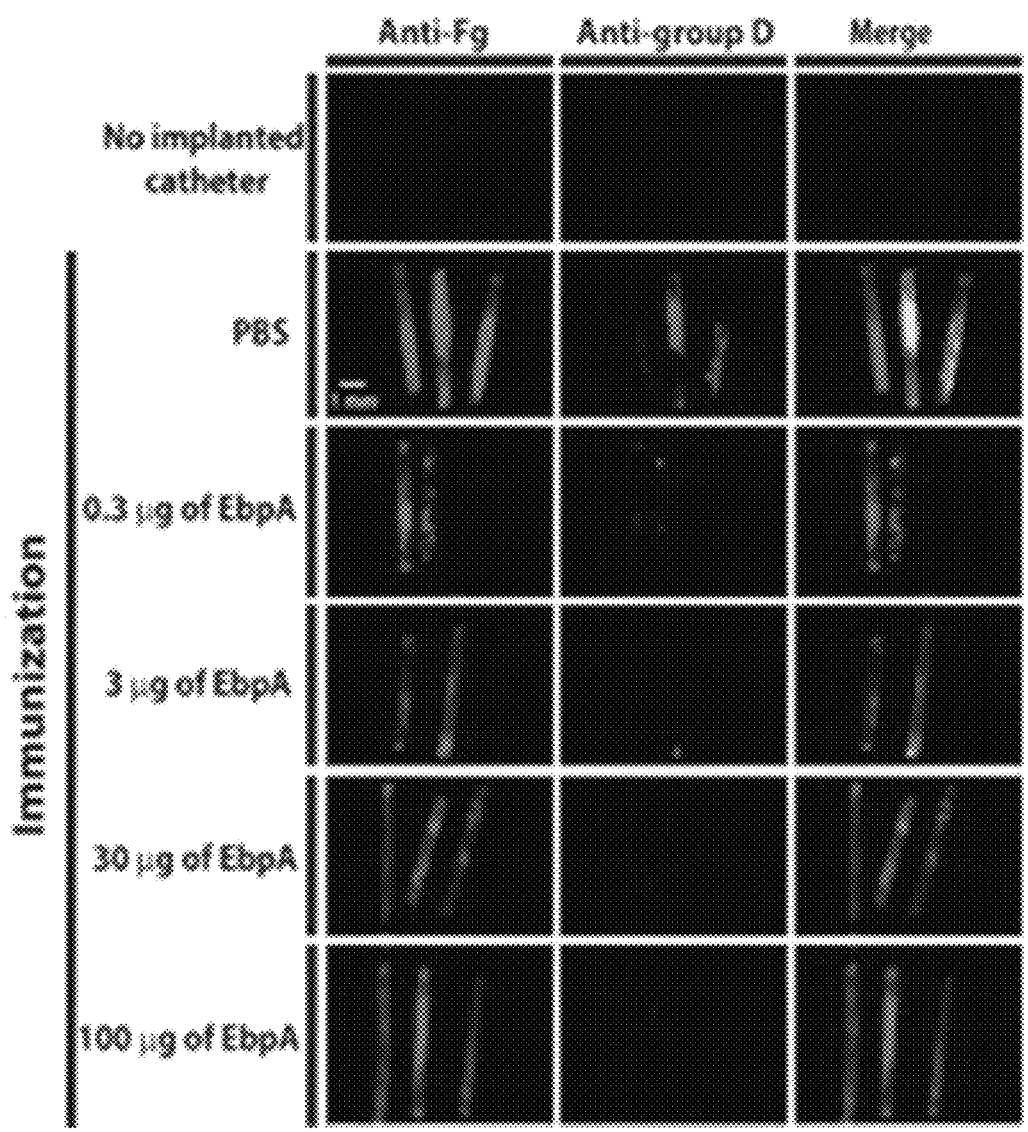
Figure 10A:
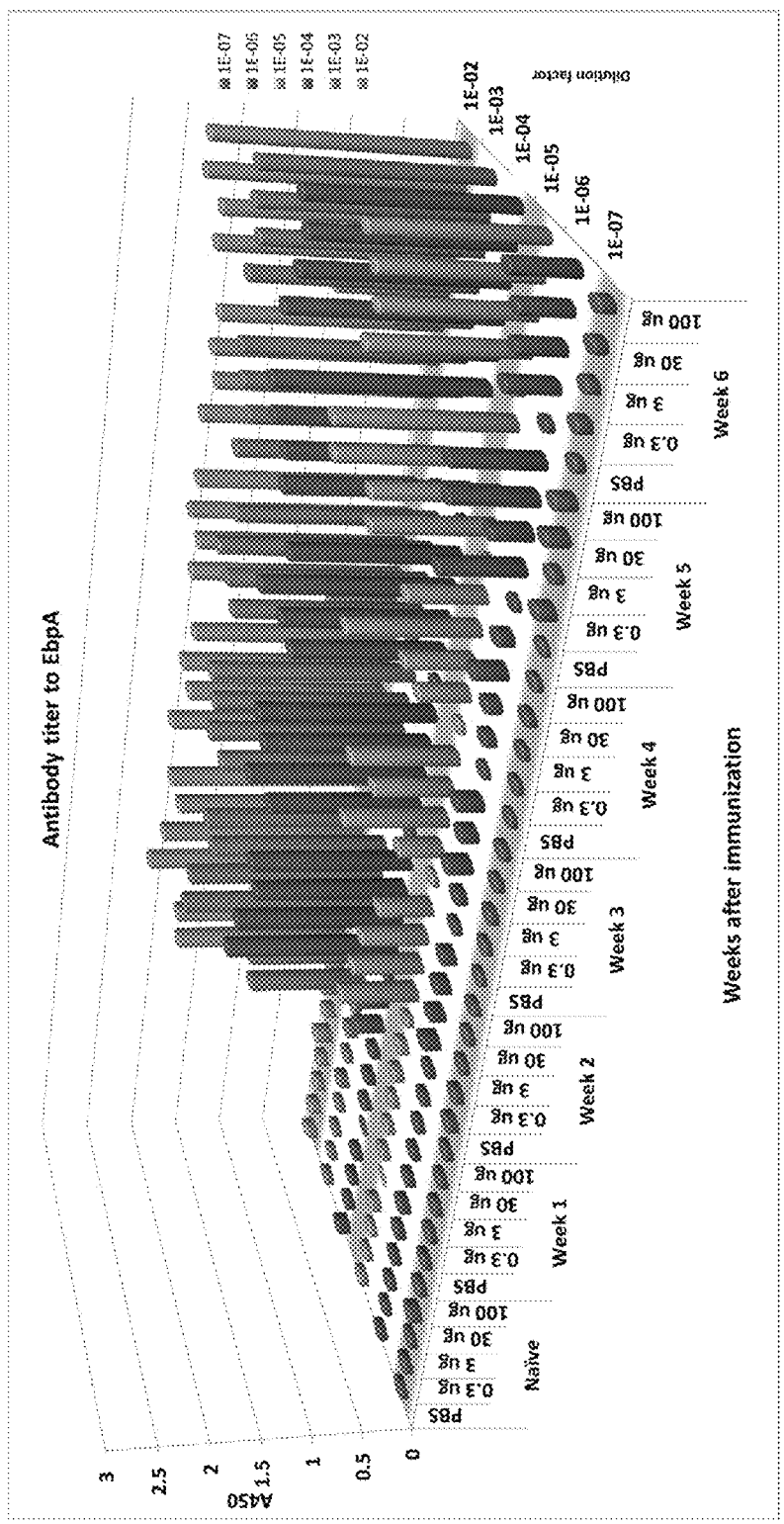
FIG. 10A, FIG. 10B and FIG. 10C depict graphs showing that EbpA$^{Full}$ immunization induces long-lasting, high-titer antibody responses.
Figure 10B:
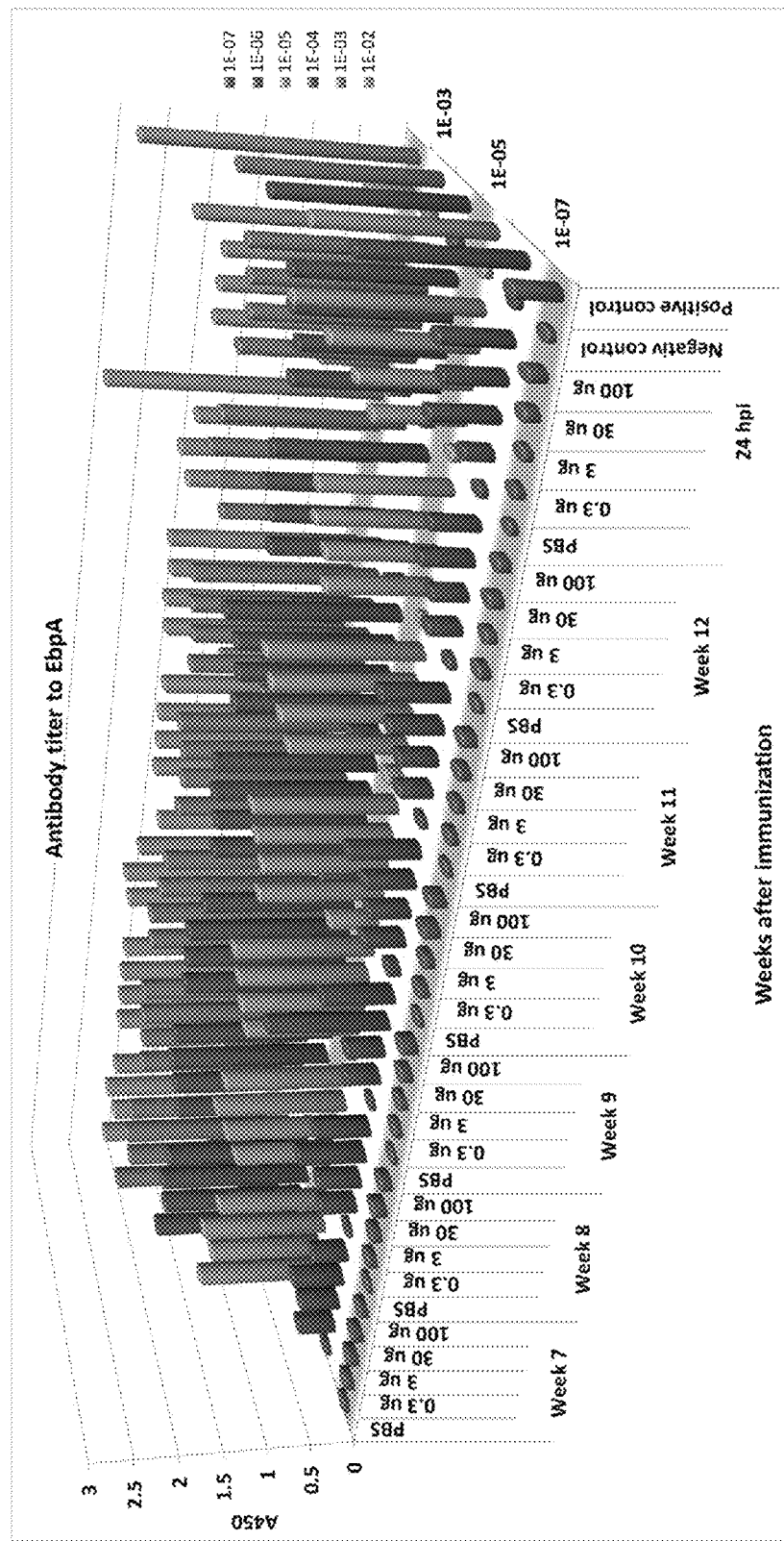
Figure 10C:
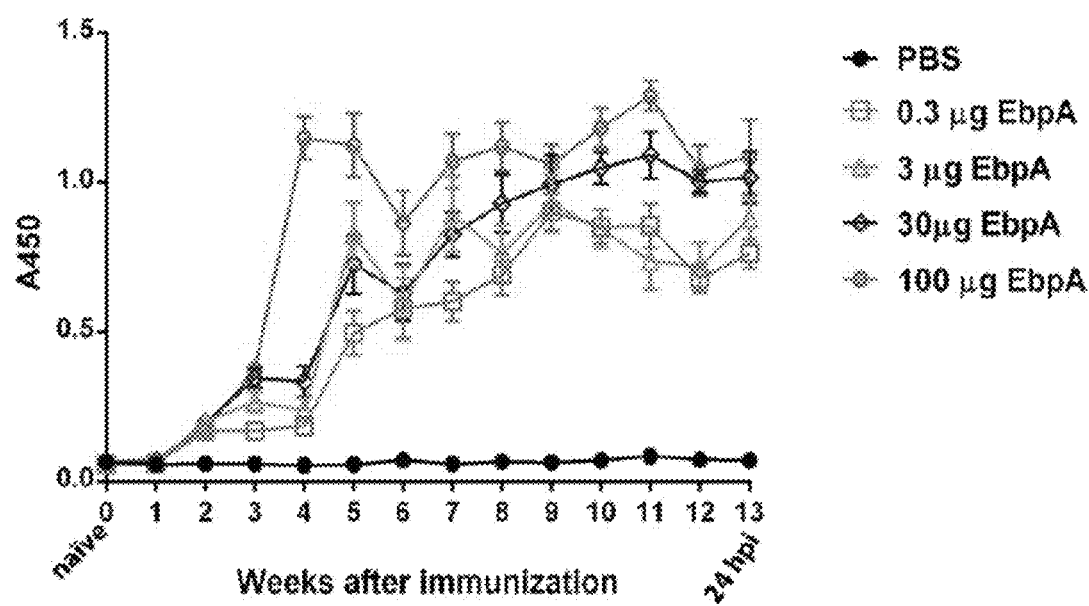
Figure 11A:
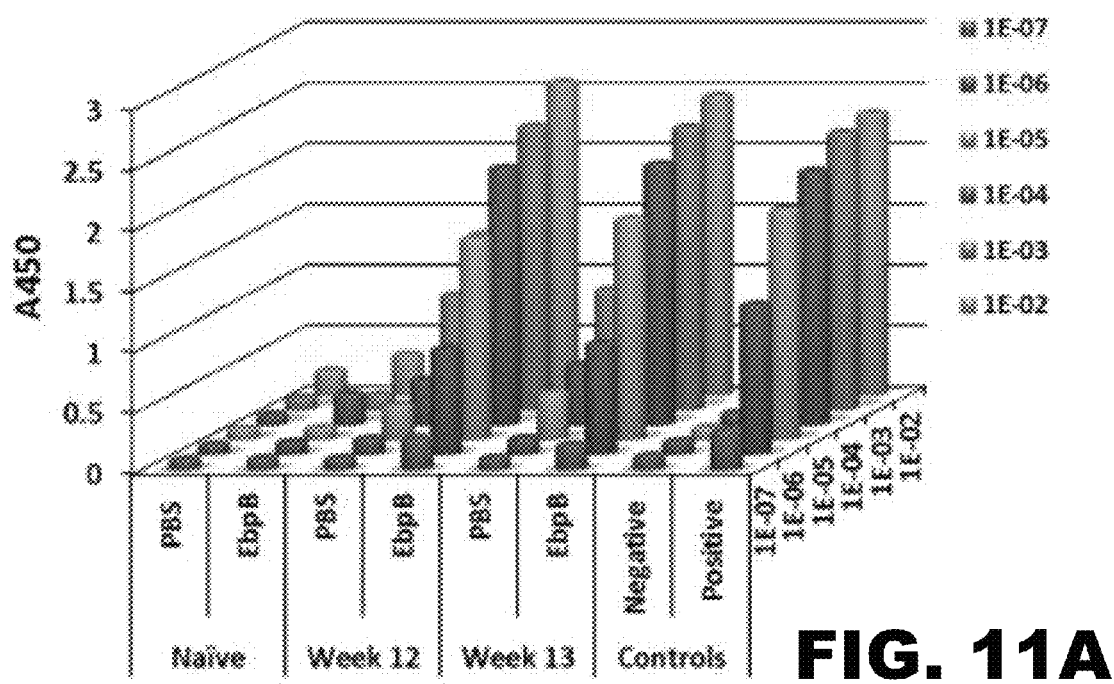
FIG. 11A, FIG. 11B, FIG. 11C, FIG. 11D, FIG. 11E, FIG. 11F, FIG. 11G, FIG. 11H, FIG. 11I and FIG. 11J depict graphs showing murine serum titers to Ebp subunits and EbpA domains. Titers to EbpB (FIG. 11A), EbpC (FIG. 11B), EbpA$^{CTD}$ (FIG. 11C), EbpA$^{NTD}$ (FIG. 11D) and, EbpA$^{Full}$ (FIG. 11I) were analyzed by pooling samples from 10 individual mice of each immunization treatment and diluted 1:100 before serial dilution. Mice immune response to EbpB (FIG. 11E), EbpC (FIG. 11F), EbpA$^{CTD}$ (FIG. 11G), EbpA$^{NTD}$ (FIG. 11H) or, EbpA$^{Full}$ (FIG. 11J) immunization throughout the experiment. Samples from 10 individual mice were diluted to 1:1,000,000 for serologic analysis. Antibody responses were assessed by ELISA. Shown is the A450 value obtained following 5 min of reaction. Values represent means ±SEM.
Figure 11B:
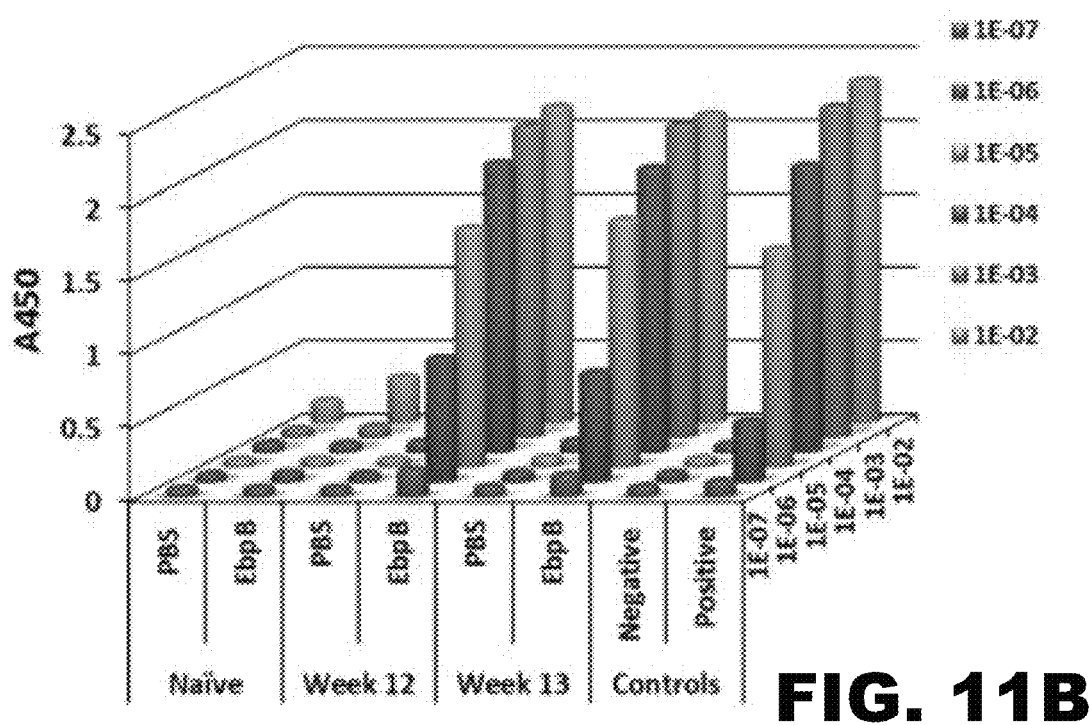
Figure 11C:
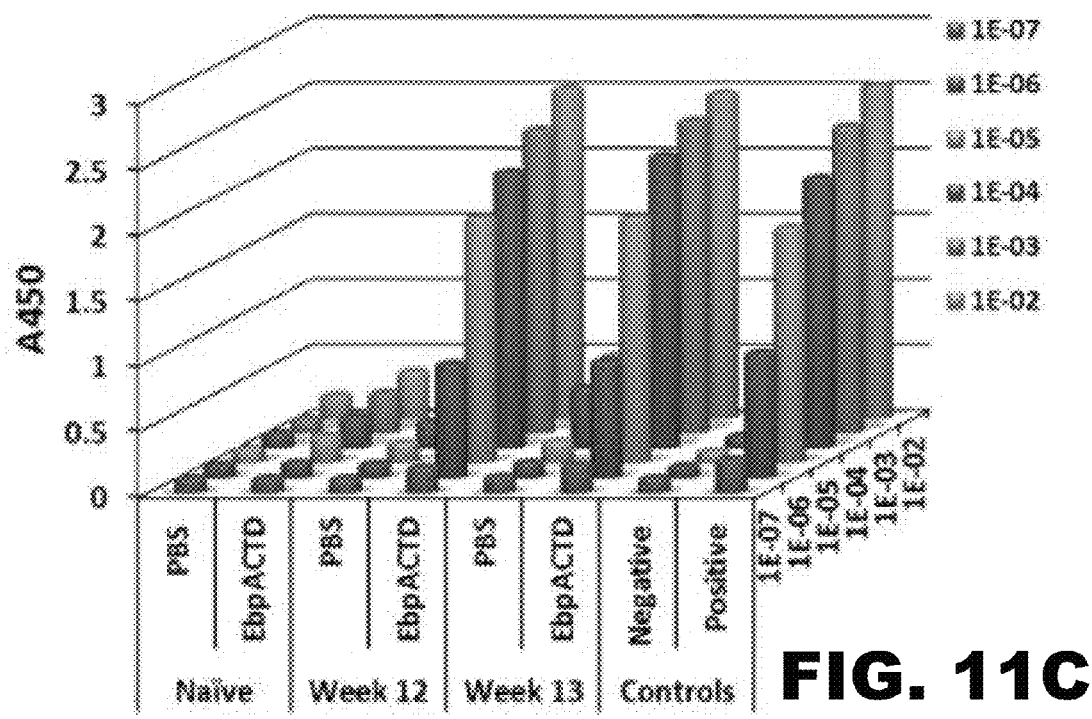
Figure 11D:
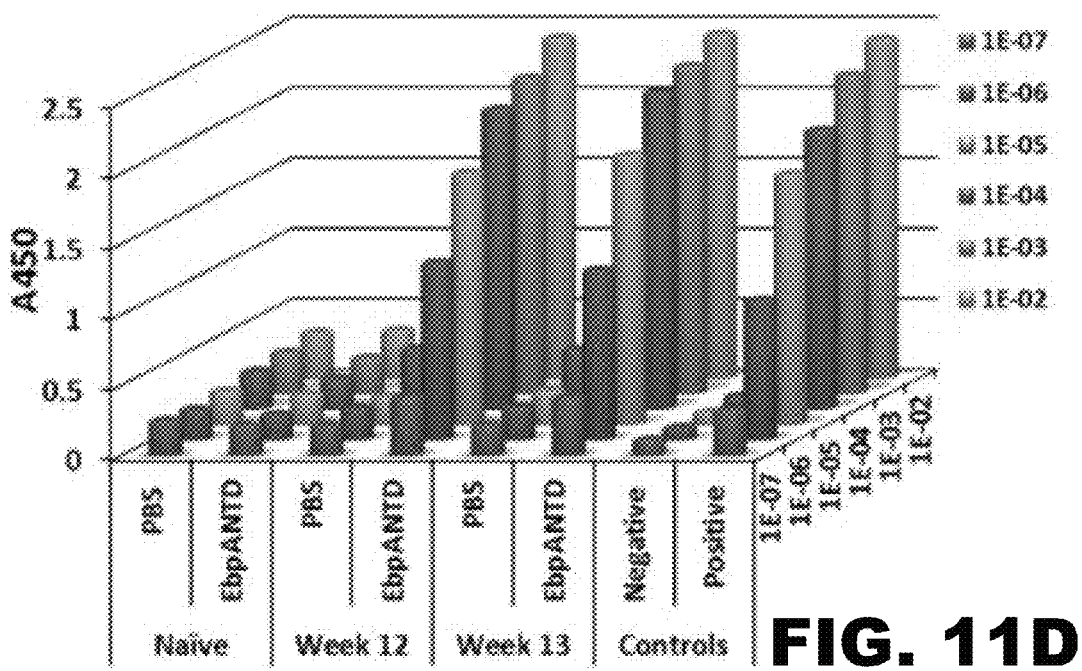
Figure 11E:
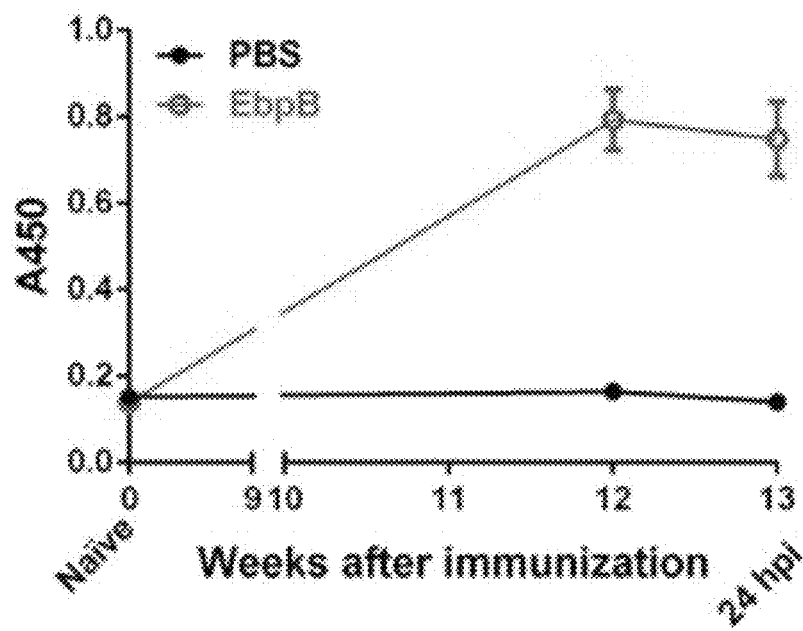
Figure 11F:
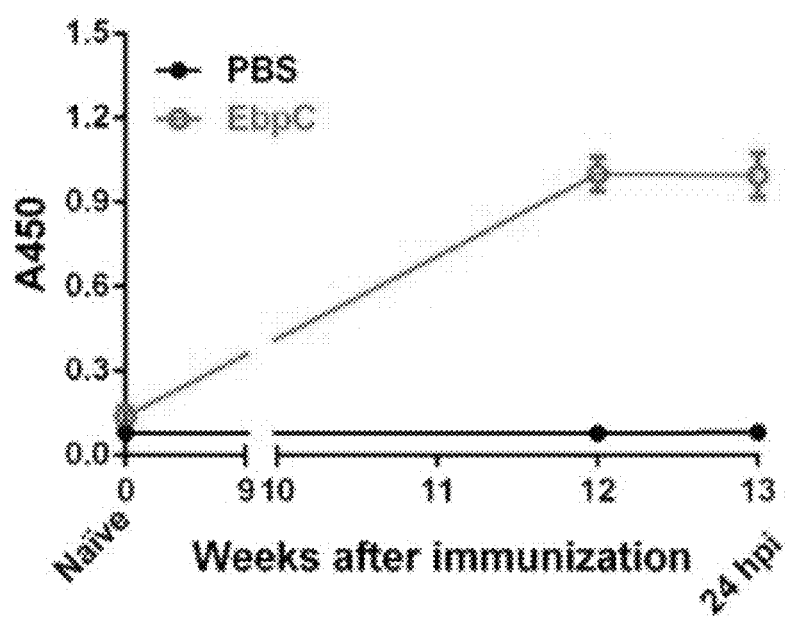
Figure 11G:
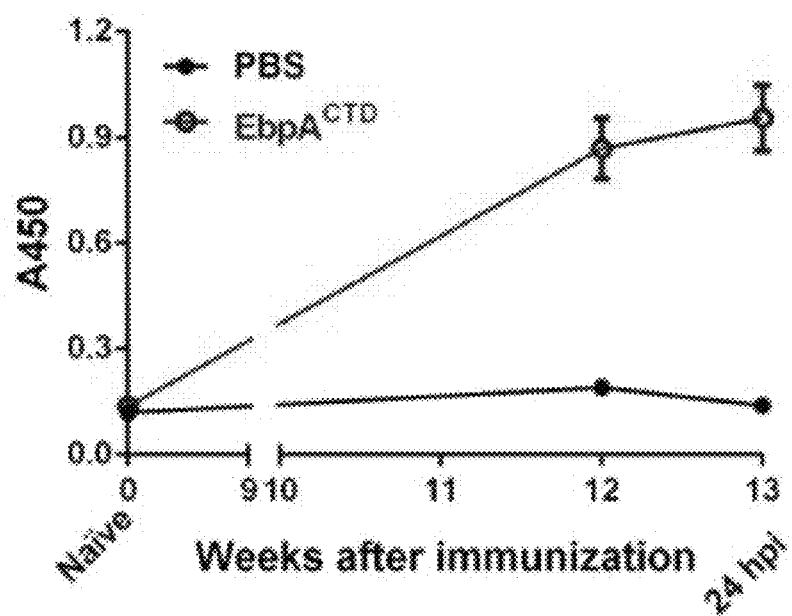
Figure 11H:
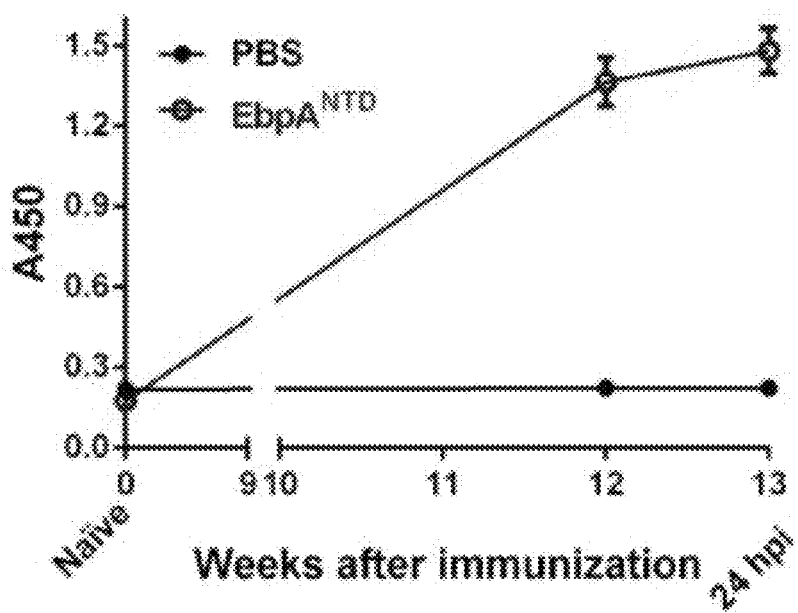
Figure 11I:
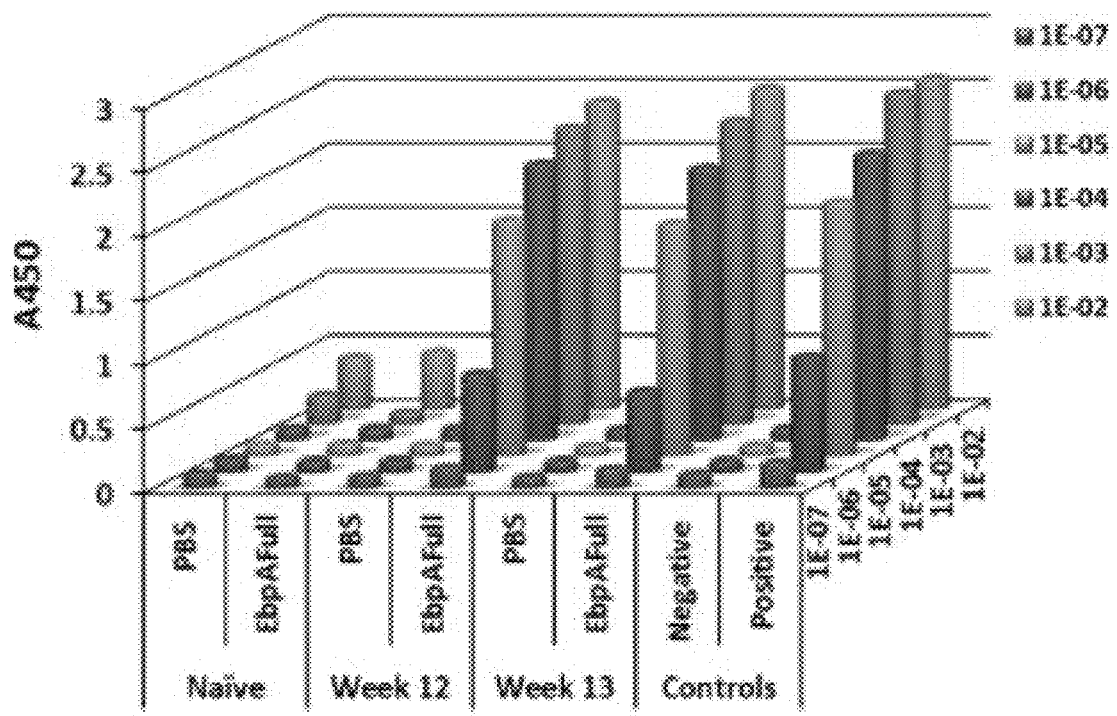
Figure 11J:
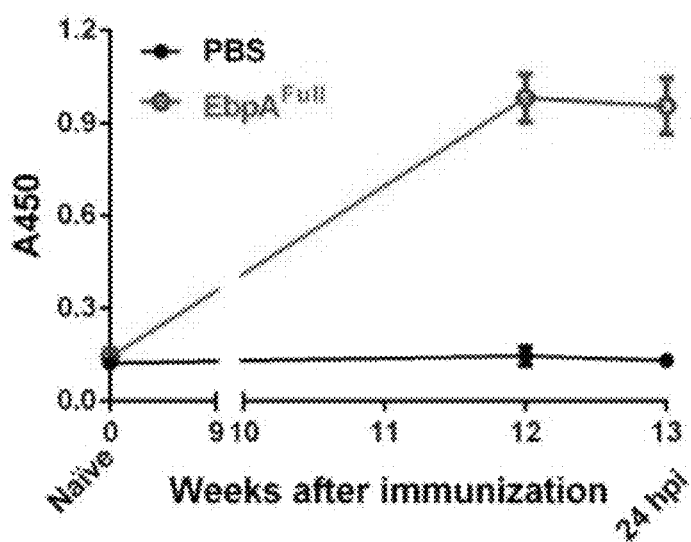

The data above revealed that the interaction between EbpA$^{NTD}$ and fibrinogen was a critical component of catheter biofilm formation by E. faecalis. Thus, we hypothesized that an intervention that blocks this interaction would be protective against development of E. faecalis CAUTIs. Therefore, we investigated the efficacy of immunizing mice with purified EbpA$^{Full}$ emulsified in Freund's complete adjuvant at doses ranging from 0.3 to 100 μg, with booster immunizations corresponding to the original dose on weeks 4 and 8. We found that immunization with EbpA$^{Full}$, but not phosphate-buffered saline (PBS) with adjuvant, generated high titers of anti-EbpA antibodies as early as 2 weeks after immunization (FIG. 10A, FIG. 10B). This immunogenic response was long-lasting and was still vigorous when examined 13 weeks after vaccination with titers correlating with EbpA dose (FIG. 10C). Four weeks after the second boost, mice were implanted with catheters and challenged with 2×10$^7$ CFU of E. faecalis OG1 RF. We found that even at the lowest EbpA dose, vaccination significantly reduced bacterial burdens in both the bladder and catheter by ~4 logs compared to control mice receiving only PBS with adjuvant (P<0.0005) (FIG. 5A and FIG. 5B). Furthermore, direct immunofluorescence staining of the recovered catheters revealed that whereas E. faecalis colocalized with fibrinogen deposition in PBS control mice, vaccination with EbpA$^{Full}$ in adjuvant reduced bacterial accumulation to undetectable levels (FIG. 5C).

Figure 5D:
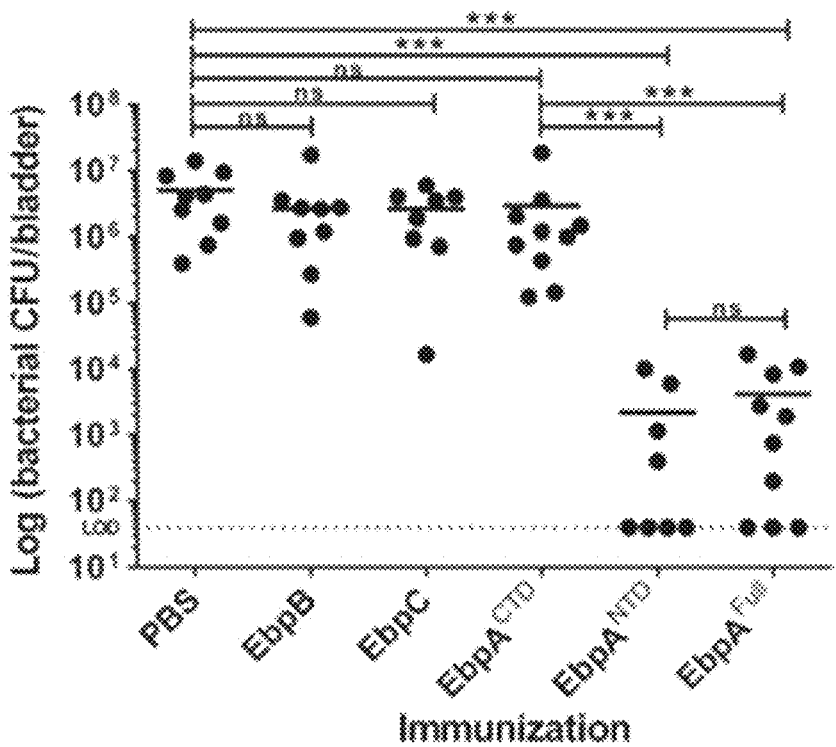
Figure 5E:
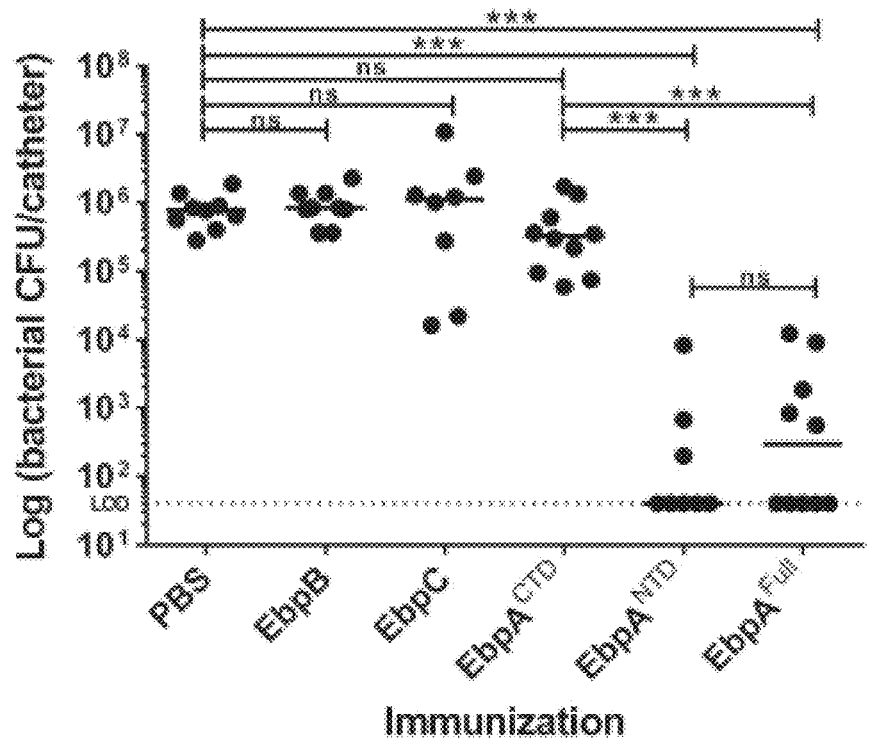
Figure 5F:
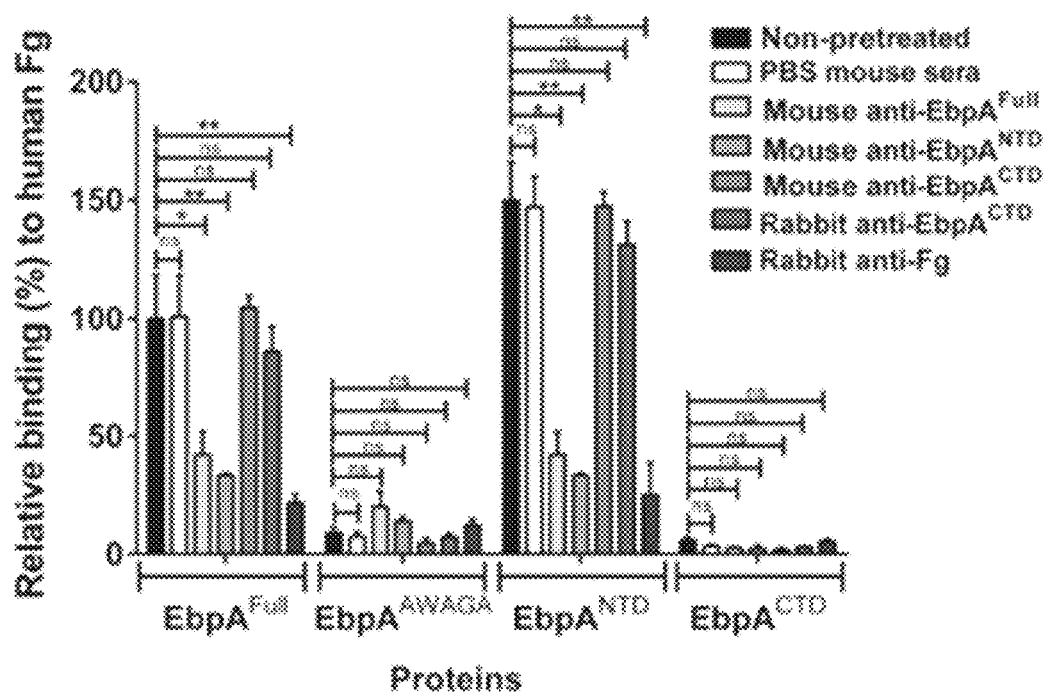

To examine whether protection correlated with fibrinogen binding, additional mice were vaccinated with pilus subunits EbpB and EbpC and the EbpA$^{CTD}$ and EbpA$^{NTD}$ truncated versions. We found that all proteins produced a strong immunogenic response (FIG. 11A, FIG. 11B, FIG. 11C, FIG. 11D and FIG. 11I), lasting through the time of the experiment (FIG. 11E, FIG. 11F, FIG. 11G, FIG. 11H and FIG. 11J). Upon challenge, immunization with EbpB and EbpC and the EbpA$^{CTD}$ failed to provide protection, with bacterial burdens in bladders and catheters similar to the PBS control. However, immunization with EbpA$^{NTD}$ was as effective as EbpA$^{Full}$ in reducing bladder and catheter bacterial burdens (P<0.0005) (FIG. 5D and FIG. 5E). To confirm this result, we tested the binding of purified EbpA variant proteins to immobilized human fibrinogen in the presence of antisera from EbpA$^{CTD}$-, EbpA$^{Full}$-, or EbpA$^{NTD}$-vaccinated mice. We found that sera from EbpA$^{Full}$- and EbpA$^{NTD}$-vaccinated mice effectively blocked the interaction in contrast to sera from EbpA$^{CTD}$-vaccinated mice, which had no effect (FIG. 5F). Together, these data implicate a protective antibody response that targets a critical EbpA-fibrinogen interaction that is required for subsequent formation of catheter biofilm formation and disease.

Discussion for Examples 1-5.

Figure 12:
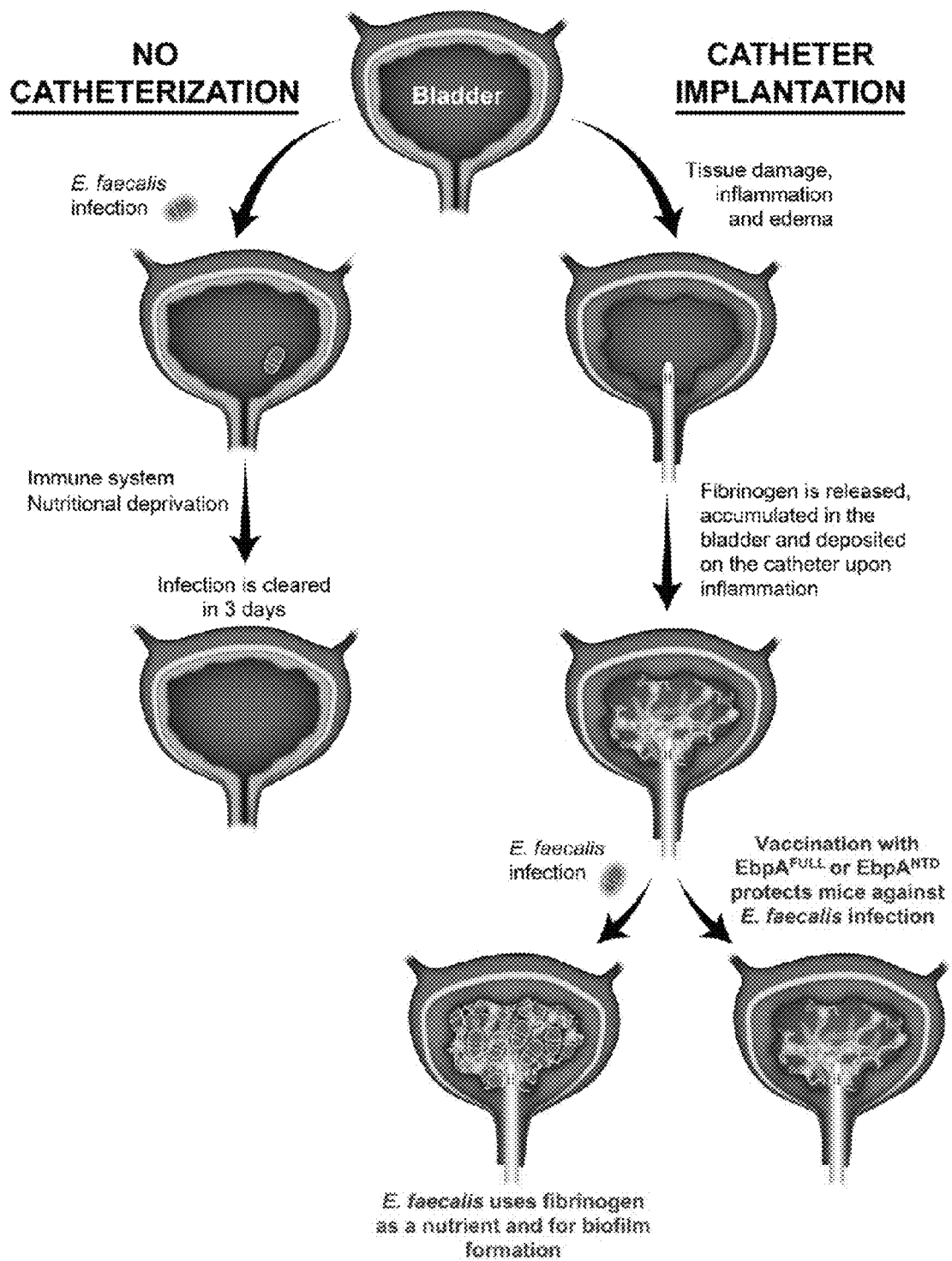
FIG. 12 depicts a model of *E. faecalis* pathogenesis during CAUTIs.

Here, we have identified an essential step in the pathogenesis of E. faecalis CAUTIs and exploited this knowledge for the development of a new therapeutic that prevents disease in a murine model (FIG. 12). We have shown that this bacterium, via its Ebp pilus, can persist by taking advantage of the host inflammation response and the associated deposition of fibrinogen to enhance biofilm formation and growth. Previously, we have shown that interleukin-1α (IL-1α) and IL-6 were elevated during catheter implantation and that these inflammatory cytokines were further increased about twofold when E. faecalis was present (12). These cytokines have been shown to trigger the expression of fibrinogen in the liver and its release into the circulatory system (29-32), where it subsequently may be able to leak into the bladder because of tissue damage caused by the catheter (FIG. 12). The importance of inflammation during CAUTI pathogenesis is illustrated by the fact that in the absence of catheter-induced inflammation, E. faecalis OG1 RF is cleared from bladders within a few days (14), possibly due to nutritional deprivation, immune surveillance, or both. We discovered that growth of E. faecalis OG1 RF in urine requires a protein source (FIG. 12). Proteinuria is induced upon catheterization but also as the result of renal damage, chronic kidney disease, and diabetes (33-35), which could make patients susceptible to infection (36-39). Although E. faecalis CAUTIs induces neutrophil infiltration in the bladder, the infection is not cleared (12). Thus, activation of the immune response provides a milieu that supports E. faecalis growth, whereas biofilm formation and/or other pathogenic mechanisms may allow E. faecalis to simultaneously evade the immune response. Analysis of the role of fibrinogen in nutrient acquisition and in inflammation may further elucidate these mechanisms.

EbpA contributed to biofilm formation, if standard TSBG medium was used, on several different materials including PVC, polystyrene, and silicon, but not under urine conditions. Under urine conditions, biofilm formation required both EbpA and the presence of fibrinogen. Thus, differences in biofilm formation were mostly dependent on the media and not the surface of the catheter. Accordingly, biofilm formation in vitro in TSGB did not accurately reflect the requirements for CAUTIs in vivo. These results also explain our previous findings in which genes required for biofilm formation in TSGB in vitro were not required in forming biofilms on catheters in vivo, arguing that the TSBG assay is not readily translatable to CAUTIs (14,40). They also highlight that in vitro efforts to study factors important for biofilm formation in vivo require an assay that most closely mimics conditions encountered in vivo. Whereas EbpA is involved in biofilm formation in the standard TSGB assay, the biofilms formed are not robust and are markedly improved using fibrinogen-supplemented urine. Furthermore, it has been shown that pH can influence biofilm formation by the fungus Aureobasidium pullulans when PVC surfaces are used (41). It is possible that pH-mediated differences in surface charge can explain EbpA's differential contribution to biofilm formation in TSGB versus fibrinogen-supplemented urine. However, this phenomenon has to be further characterized. Together, these observations validate that the fibrinogen-supplemented urine biofilm assay more accurately reproduces in vivo CAUTI conditions and should be of utility for further analysis of enterococcal biofilm formation in disease. Fibrinogen is a complex glycoprotein comprising two sets of disulfide-bridged Aα, Bβ, and γ chains (32). It is thus possible that EbpA may recognize fibrinogen via either its carbohydrate or its peptide moieties.

We also show that the EbpA-fibrinogen interaction is a vulnerable step that is sensitive to therapeutic intervention. Bladder catheterization of humans does result in inflammation (22, 43-45), and fibrinogen has been linked to multiple human inflammatory diseases where it functions not only to protect tissues but also as an important feedback regulator of the immune response (25).

It has been shown that hospitalized patients develop antibodies that recognize Ebp pili, although there is no evidence that these antibodies are protective in humans (15). A recent study showed that a monoclonal antibody against EbpC confers protection on rats against $E.\ faecalis$ endocarditis (46). In our mouse model of CAUTIs, we tested EbpC as a vaccine candidate and found that it did not confer protection against $E.\ faecalis$ CAUTIs. Only EbpA and more specifically EbpA$^{NTD}$ were protective against CAUTIs. This difference emphasizes that it is essential to understand the underlying molecular mechanisms of host-pathogen interactions made by $E.\ faecalis$ to properly intervene in a specific disease. A comparison of CAUTI pathogenesis uncovered in this study with endocarditis may reveal why EbpC was protective in the latter but not the former. Here, we elucidated that the molecular basis of protection by the EbpA vaccine was due to the disruption of an interaction that is critical in pathogenesis, between EbpA and fibrinogen. The mechanism of protection induced in response to EbpC vaccination for endocarditis remains to be determined. If our discovery could be translated to clinical application, it would offer a prophylactic option to prevent $E.\ faecalis$—mediated CAUTIs. However, development of such a technology will require significant resources to investigate whether translation to humans is possible and economically feasible. Additionally, although EbpA$^{NTD}$ is highly conserved, this study was focused on EbpA from $E.\ faecalis$.

Our finding that protection is only associated with EbpA$^{NTD}$ suggests that the Ebp pilus has evolved a decoy strategy to sequester its vulnerable EbpA$^{NTD}$ from immune surveillance during CAUTIs. It is likely that the identification of this vulnerability will provide insight into the pathogenesis of other $E.\ faecalis$ catheter-related diseases and will reveal general mechanisms applicable to catheter infections caused by other bacterial pathogens that can also be exploited for the development of effective therapies.

Methods for Examples 1-5.

Study design: For experiments involving mice, we used 6-week-old female mice, and 10 mice were used for each treatment because in our experience 10 mice is the minimum number of mice needed to observe statistically significant differences per treatment. We used an optimized murine model of $E.\ faecalis$—mediated CAUTIs that faithfully reproduces the pathogenesis of human disease, by transurethral implantation of a 5-mm platinum-cured silicone tube into the bladder lumen. For immunohistochemistry of mouse bladder and immunofluorescence staining of the catheter, implanted and infected mice were randomly taken from the 10 mice treated group. Then, bladder and catheters were immunostained for $E.\ faecalis$ and fibrinogen to visualize colocalization. For the vaccination experiments, we monitored the production of antibodies against Ebp proteins in treated mice; blood samples were taken from each mouse every week for the time period of the experiment and evaluated by ELISA. For the in vitro urine growth and biofilm experiments, we collected and pooled urine from at least three human female donors between 20 and 35 years of age who were healthy and excluding those with kidney disease, a current UTI, or those undergoing antibiotic treatment. All assays were done at least three times in triplicate. This study was not blinded.

Bacterial strains and growth conditions: Unless otherwise specified, $E.\ faecalis$ strains OG1 RF and its derivatives were grown overnight on Brain Heart Infusion (BHI) broth (BD Company) supplemented with rifampin (25 µg/ml) (Sigma-Aldrich) and fusidic acid (25 µg/ml) (Sigma-Aldrich) and were inoculated from a single bacterial colony grown on BHI agar plates supplemented with rifampin and fusidic acid. Liquid cultures were grown statically at 37° C. for 18 hours. $E.\ coli$ strains were grown in LB broth or agar (Becton, Dickinson and Company) supplemented with ampicillin (100 µg/ml) and kanamycin (100 µg/ml). Bacterial strains are listed in Table 1.

General Cloning Techniques: Bacterial genomic DNA (gDNA) was isolated with the Wizard Genome DNA purification kit (Promega Corp.). Plasmid DNA was purified with the Wizard Plus SV Minipreps DNA Purification System (Promega Corp.). Primers were purchased from Integrated DNA Technologies. Phusion High-Fidelity DNA polymerase, restriction enzymes, and T4 DNA ligase were purchased from New England Biolabs and used according to the methods described by the manufacturers. DNA fragments generated by polymerase chain reaction (PCR) or restriction digestion were purified by QIAquick PCR or Gel Extraction kit (Qiagen Inc.). Plasmids were transformed into $E.\ coli$ TOP10 or M15 (pREP4). All constructs were confirmed by DNA sequence analysis of the inserts. Plasmids and primers used in this study are listed in Table 2 and Table 3, respectively.

Construction of plasmids for the expression of 6xHis-EbpA$^{Full}$, 6xHis-EbpA$^{AWAGA}$, and 6xHis-EbpA$^{NTD}$ proteins: DNA fragments containing ebpA and ebpA$^{NTD}$ were amplified by PCR from gDNA of $E.\ faecalis$ OG1 RF (SJH-1994). A fragment containing ebpA$^{AWAGA}$ $_{(SEQ\ ID\ NO:1)}$ was amplified from an $E.\ faecalis$ ebpA$^{AWAGA}$ $_{(SEQ\ ID\ NO:1)}$ chromosomal MIDAS motif mutant (SJH-2001) with primers ALFM01 and ALFM02. The full amino acid sequence of EbpA was analyzed to detect structural domains. The EbpA signal sequence was predicted to be composed of amino acids 1 to 34 with SignalP4.1 server. Additionally, we deduced that the vWA domain was located within residues 200 to 385. On the basis of the flexibility and hydrophobicity analyses of EbpA, we determined that starting from amino acid 115 would result in a soluble protein that would not disturb the vWA domain. Amplified genes were close to full length, starting from 115 until 1072 amino acids, missing C-terminal hydrophobic and positively charged domains. The resulting PCR products were inserted into pQE-30Xa between its Bam HI and Nhe I restriction sites. The resulting plasmids pSJH-687 (ebpA) and pSJH-688 (ebpA$^{AWAGA}$ $_{(SEQ\ ID\ NO:1)}$) were used to transform $E.\ coli$ M15 (pREP4) to create strains SJH-2610 and SJH-2611, respectively. ALFM51 and ALFM52 were used to obtain an ebpA$^{NTD}$ fragment with pSJH-2610 as a template. The whole plasmid was amplified except the C-terminal domain (encoding amino acid residues 594 to 1072). The resulting fragment was digested Eco RV and then inserted into pQE-30Xa by ligation with Blunt/T4 ligase master mix, creating plasmid pSJH-689.

Purification of 6xHis-EbpA$^{Full}$, 6xHis-EbpA$^{AWAGA}$ (SEQ ID NO:1), and 6xHis-EbpA$^{NTD}$ proteins: To overexpress proteins, E. coli M15 (pREP4) containing plasmid pSJH-687, pSJH-688, or pSJH-689 were cultured in 5 liters of fermentor vessel containing Super Broth at 37° C. When an OD$_{600}$ (optical density at 600 nm) of 4.0 was attained, cultures were induced with 0.15 mM isopropyl-β-D-thiogalactopyranoside and incubated for an additional 1.5 hours. Cells were harvested by centrifugation for 10 min at 4° C. The pellets were suspended in 1x PBS with 250 mM NaCl and disrupted by sonication (Fisher, sonic dismembrator). The lysates were cleared by centrifugation at 18,600g for 30 min at 4° C. and filtered with a 0.22-μm GP Millipore Express Plus membrane (SCGPT02RE, Millipore Inc.). EbpA proteins were purified by chromatography with a Talon cobalt affinity column (Clontech Inc.).

Fractions containing EbpA or EbpA$^{AWAGA}$ (SEQ ID NO:1) were pooled and subjected to additional purification by hydrophobic interaction chromatography (PHE15 source; GE Healthcare). Fractions containing EbpA or EbpA$^{AWAGA}$ (SEQ ID NO:1) were pooled and dialyzed against 20 mM tris (pH 8.0), followed by a chromatography with a Source 15Q column (GE Healthcare). For further purification of EbpA$^{NTD}$ protein, fractions from the Talon column were pooled and dialyzed against 20 mM tris (pH 8.0), followed by chromatography over an SP Sepharose Fast Flow column (GE Healthcare). Fractions containing EbpA$^{NTD}$ were pooled and dialyzed against 20 mM tris (pH 8.0) followed by a chromatography with a Source 15Q column (GE Healthcare). EbpA proteins were concentrated with an Amicon Ultra cell with YM-10 filter membrane (10,000 molecular weight cutoff; EMD Millipore Inc.).

Purification of 6xHis-EbpA$^{CTD}$, 6xHis-EbpB, and 6xHis-EbpC proteins: Overexpression and purification of these proteins were done by following the protocol used by Nielsen et al. (18).

Coverslip biofilm assay: E. faecalis strains were grown overnight, and then the cultures were diluted to OD$_{600}$ of 0.2 in BHI broth, followed by 1:100 dilution in tryptic soy broth supplemented with 0.25% glucose (TSBG). Biofilm assay was performed as previously described (40). Bacterial cells were allowed to attach to the polyvinyl chloride coverslips for 48 hours at 37° C. under static conditions. Coverslips were washed with sterile water and then stained with 0.5% crystal violet (Sigma-Aldrich) for 10 min at room temperature. Excess dye was removed by rinsing with sterile water, and the coverslips were allowed to dry at room temperature. Biofilms were then dissolved with 500 μl of 33% acetic acid (Fisher Scientific), and the absorbance (OD$_{595}$) was measured with a microplate reader (Molecular Devices). Experiments were performed independently in triplicate with three coverslips per condition per experiment.

Urine biofilm assay on silicon catheters and 96-well polystyrene plates: E. faecalis strains were grown overnight, and then the cultures were diluted to an OD$_{609}$ of 0.2 in BHI broth. The diluted culture was centrifuged and washed (three times) with 1xPBS, followed by 1:100 dilution in urine supplemented with indicated source of protein or in TSBG as a standard control. Bacterial cells were allowed to attach to the silicon catheters (1 cm, Nalgene 50 silicon tubing, Brand Products) or 96-well polystyrene plates (Greiner CELLSTAR) for 48 hours at 37° C. under static conditions. Silicon catheters and 96-well polystyrene plate were washed with sterile water and then stained with 0.5% crystal violet for 10 min at room temperature. Excess dye was removed by rinsing with sterile water, and the coverslips were allowed to dry at room temperature. Biofilms were then dissolved with 500 or 200 μl of 33% acetic acid for silicon catheters or 96-well polystyrene, respectively, and the absorbance (OD$_{595}$) was measured with a microplate reader (Molecular Devices). Experiments were performed independently in triplicate with three coverslips per condition per experiment. Urine was pooled from three healthy female donors, clarified by centrifugation, filter-sterilized, and adjusted to pH 6.5 before use.

E. faecalis OG1RF growth in urine: Bacterial growth from overnight cultures was normalized to an OD$_{600}$ of 1.0 in BHI broth. Bacterial cells were then washed (three times) with 1xPBS to remove traces of BHI broth, followed by 1:1000 dilution into undiluted pooled female urine (adjusted to pH 6.5), and, when indicated, supplemented with Fg, BSA, or casamino acids. Bacterial growth was monitored by quantifying CFU. To examine the consumption of Fg by E. faecalis, bacteria were grown in the presence of Fg and incubated for 24 hours at 37° C., and samples were then analyzed by negative staining and transmission electron microscopy as below.

Transmission electron microscopy: Cells were fixed in 4% paraformaldehyde-0.5% glutaraldehyde in 100 mM Pipes-0.5 mM MgCl$_2$ (pH 7.2) for 1 hour at 4° C. Cells were absorbed to grids, washed in distilled water, and stained with 1% uranyl acetate-1.6% methylcellulose. Excess liquid was gently removed and grids were allowed to air dry. Cells were analyzed on a JEOL 1200EX transmission electron microscope at an accelerating voltage of 100 kV. Images were acquired with an XR80M-B 8-megapixel charge-coupled device camera system (Advanced Microscopy Techniques Corp.).

Antibodies used in this study: Primary antibodies: Goat anti-fibrinogen (Sigma-Aldrich); mouse anti-uroplakin III (Research Diagnostics); rabbit anti-Streptococcus group D antigen (Lee Laboratories); and mouse anti-EbpA$^{Full}$, mouse anti-EbpA$^{NTD}$, mouse anti-EbpA$^{CTD}$, anti-EbpC, and anti-EbpB were generated in this study; rabbit anti-EbpA$^{CTD}$ was made from C-terminal domain (EbpA$^{CTD}$) (18).

Secondary antibodies: Alexa Flour 488—labeled donkey anti-goat, Alexa Flour 594—labeled donkey anti-mouse, Alexa Flour 647—labeled donkey anti-rabbit, IRDye 800CW donkey anti-goat, and IRDye 680LT goat anti-rabbit were used. Alexa Flour secondary antibodies were purchased from Invitrogen Molecular Probes, and IRDye conjugate secondary antibodies were from LI-COR Biosciences.

Whole bacterial binding to collagen I and fibrinogen: To determine whether E. faecalis strains adhere to immobilized collagen I and fibrinogen, we adapted the method described by Nallapareddy et al. (16). Immulon 4 HBX flat-bottom microplates (Thermo Fisher) were coated overnight at 4° C. with human collagen I (100 μg/ml) (BD Biosciences) and human fibrinogen free from plasminogen and von Willebrand factor (Enzyme Research Laboratory). The plates were blocked for an hour with 5% milk in PBS, followed with PBS washes (three times for 5 min). Bacteria strains were grown overnight in BHI broth, normalized to an OD$_{600}$ of 1.0, and then washed and resuspended in PBS. A total of 100 μl of bacteria was added to the coated wells and incubated for an hour at 37° C., followed by PBS washes with the wash function of a microplate reader (ELX405 Select CW, BioTek Instruments) to remove the unbound bacteria. Next, bacterial cells were fixed with formalin for 20 min at room temperature, followed by three washes with PBS containing 0.05% Tween 20 (PBS-T). Then, the plates were blocked overnight at 4° C. with 5% milk PBS-T (PBS-T5M), followed by three washes with 1% milk PBS-T (PBS-T1 M). After the washes, the plates were incubated for an hour at room temperature with rabbit anti—*Streptococcus* group D antigen antisera (1:500). Plates were washed with PBS-T1 M, incubated with the Odyssey secondary antibody (goat anti-rabbit IRDye 680LT, diluted 1:10,000) for 45 min at room temperature, and washed with PBS-T (three times). As a final step, the plates were scanned for infrared signal with the Odyssey Imaging System (LI-COR Biosciences).

EbpA protein binding to fibrinogen: Purified $EbpA^{WT}$, $EbpA^{AWAGA}$ (SEQ ID NO:1), $EbpA^{NTD}$, and $EbpA^{CTD}$ were tested for Fg binding. Plates were coated with Fg, blocked, and washed as described above. When indicated, EbpA proteins were incubated with sera from vaccinated mice or with rabbit anti-$EbpA^{CTD}$ (18) for an hour at room temperature before the fibrinogen-EbpA binding assay. EbpA proteins were incubated with Fg for an hour at room temperature. Mouse anti-$EbpA^{Full}$ was used as primary antibody to detect bound EbpA. The use of anti-$EbpA^{Full}$ for detection of Full, NTD, and CTD EbpA proteins was validated by ELISA and shown to recognize all of these proteins at similar levels (FIG. 11). Similarly, it was confirmed that anti-$EbpA^{NTD}$ and anti-$EbpA^{CTD}$ specifically recognized NTD or CTD, respectively, and both recognized $EbpA^{Full}$. Goat anti-mouse or anti-rabbit IRDye secondary antibodies were used, and analyses were done with Odyssey Imaging System (LI-COR Biosciences) as described above.

Determination of antibody responses in mice: Each protein (10 µg) was used to coat Immulon 4 HBX flat-bottom microplates overnight at 4° C. Plates were washed (three times) using PBS with 0.05% Tween 20 (PBS-T) to remove unbound protein. The plates were blocked for 2 hours with PBS containing 1.5% BSA and 0.1% sodium azide and washed (three times) with PBS-T. Serum samples from vaccinated mice were diluted 1:100 in dilution buffer (PBS with 0.05% Tween 20, 0.1% BSA, and 0.5% methyl α-D-mannopyranoside) before serial dilutions. Then, diluted samples were added into the plate and incubated for 2 hours at room temperature. After the incubation, the plates were washed (three times) with PBS-T, followed by a 1-hour incubation with horseradish peroxidase-conjugated goat anti-mouse antisera (1:2000), and then washed (three times) with PBS-T. Detection was performed with the TMB Substrate Reagent Set (BD #555214). The reactions were incubated for 5 min to let color to develop and then stopped by the addition of 1.0 M sulfuric acid. The absorbance was determined at 450 nm.

Bioinformatic analyses: Initial amino acid sequence analyses for domain structure of EbpA protein were done by BLAST and DELTA-BLAST (47, 48). Molecular modeling of structures used resources available from the PHYRE2 server (49).

Mouse catheter implantation and infection: Mice used in this study were 6-week-old female wild-type C57BL/6Ncr mice purchased from the National Cancer Institute. Mice were transurethrally implanted and inoculated as previously described (14). Mice were anesthetized by inhalation of isoflurane and implanted with a 4- to 5-mm length of platinum-cured silicone catheter. When indicated, mice were infected immediately after catheter implantation with 50 µl of ~1×10⁷ or 2×10⁷ CFU of bacteria in 1×PBS directly into the bladder by transurethral inoculation as previously described (50). To extract the catheters and organs, mice were sacrificed at desired time points by cervical dislocation after anesthesia inhalation, and the bladders were aseptically harvested. Subsequently, the silicone implant was retrieved from the bladder when present. All studies and procedures were approved by the Animal Studies Committee at Washington University School of Medicine.

Immunization of mice: Immunization protocol was adapted from the method described by Langermann et al. (51). Groups of 10 mice were used for each vaccine dose. EbpA proteins or PBS was emulsified with either Freud's complete adjuvant (first vaccination) or Freud's incomplete adjuvant (boosts). Mice were vaccinated intramuscularly with the various doses indicated in the test (time 0) and then with the same dose at 4 and 8 weeks. Mouse sera were collected before and every week after time 0 to determine the antibody response. At 4 weeks after the second boost, mice were implanted with catheters and challenged with ~1×10⁷ CFU of *E. faecalis* OG1RF. Mice were sacrificed 24 hours after infection to determine bacterial titers in the bladder and catheters, as described above.

Deposition of fibrinogen in implanted catheters: Catheters were transurethrally implanted into the mouse bladder as described above. Nonimplanted catheters were used as a control for any autofluorescence. Catheters were retrieved from implanted mouse bladder at specified time points (3, 6, 9, and 24 hours), washed with PBS, fixed with formalin for 20 min, and then washed with PBS. Catheters were blocked with PBS-T5M overnight at 4° C., washed with PBS-T1 M (three times for 5 min), and incubated at room temperature for 2 hours with primary antibody (goat anti-fibrinogen; 1:500). The catheters were then washed with PBS-T1 M (three times for 5 min), incubated with the Odyssey secondary antibody (donkey anti-goat IRDye 800CW; diluted 1:10,000) for 45 min at room temperature, and washed with PBS-T (three times). As a final step, the catheters were scanned for infrared signal with the Odyssey Imaging System (LI-COR Biosciences).

Histopathology and immunofluorescence: Bladders were fixed in neutral buffered formalin for 1 to 2 hours at room temperature and dehydrated in 70% ethanol overnight at 4° C. Fixed bladders were embedded in paraffin, sectioned, and mounted on slides. All sections were deparaffinized with xylene (two times for 10 min), rehydrated with isopropanol (three times for 5 min), and washed with water for 5 min. Bladder antigens were retrieved by boiling the section in 10 mM Na-citrate for 30 min and washed in water for 5 min, followed by washes with PBS (three times for 5 min). The sections were then blocked with 1% BSA and 0.3% Triton X-100 in PBS for 1 hour and incubated with primary antibodies (1:100) overnight at 4° C., followed by three washes with PBS. Next, sections were incubated with the secondary antibodies (1:500) for 1 hour at room temperature, followed by three washes with PBS. Sections were then counterstained with Hoechst dye specific for DNA (1:20,000 in PBS). The sections were analyzed by epifluorescence microscopy on a Zeiss Axioskop 2 MOT Plus microscope.

Statistical analyses: Data from multiple experiments were pooled. Two-tailed Mann-Whitney U tests were performed with GraphPad Prism 5 software (GraphPad Software) for all comparisons described in CAUTI experiments. Biofilm formation and binding assay were analyzed with a paired t test to evaluate the significance of differences. Values represent means ±SEM derived from at least three independent experiments. *P<0.05; P<0.005; *P<0.0005; ns, differences not significant.

Example 6

Figure 13A:
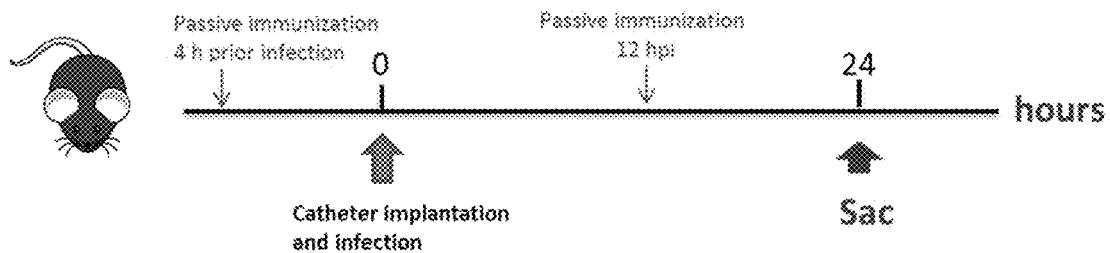
FIG. 13A, FIG. 13B and FIG. 13C depict a schematic and graphs showing EbpA$^{Full}$ and EbpA$^{NTD}$ mouse sera protect against *E. faecalis* CAUTI.
Figure 13B:
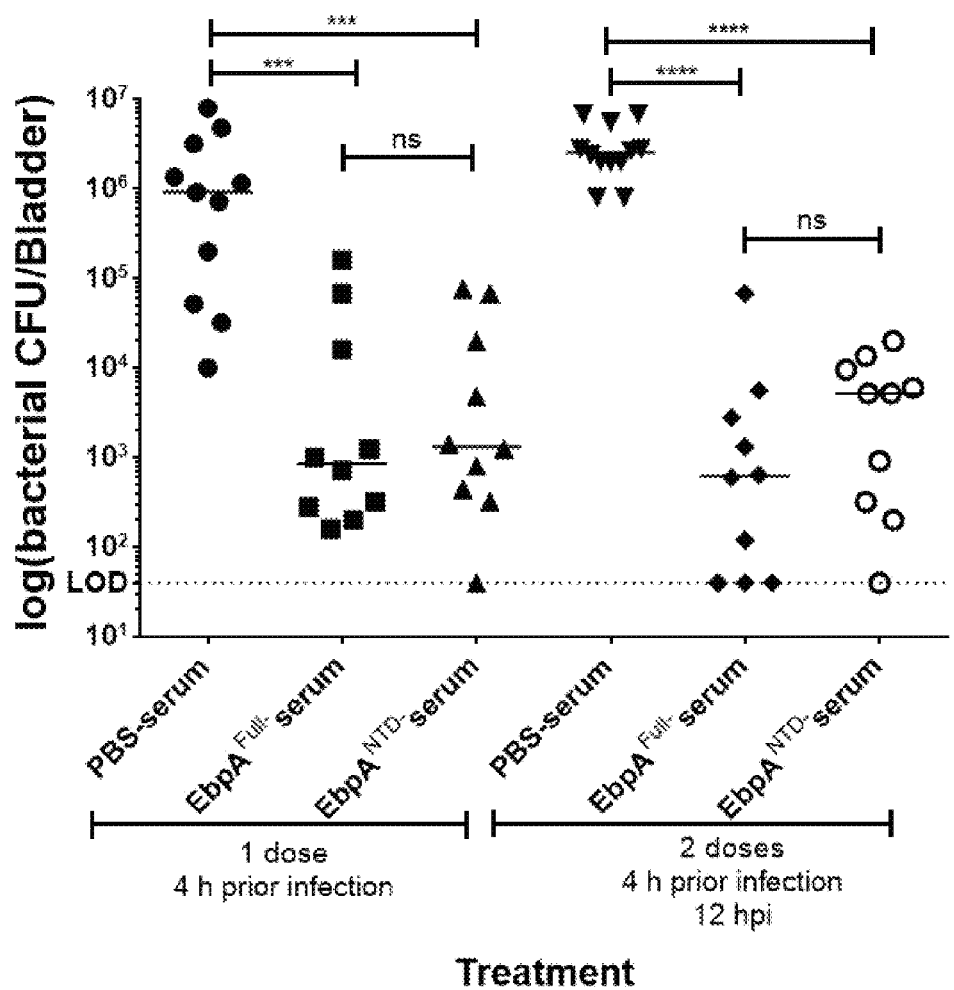
Figure 13C:
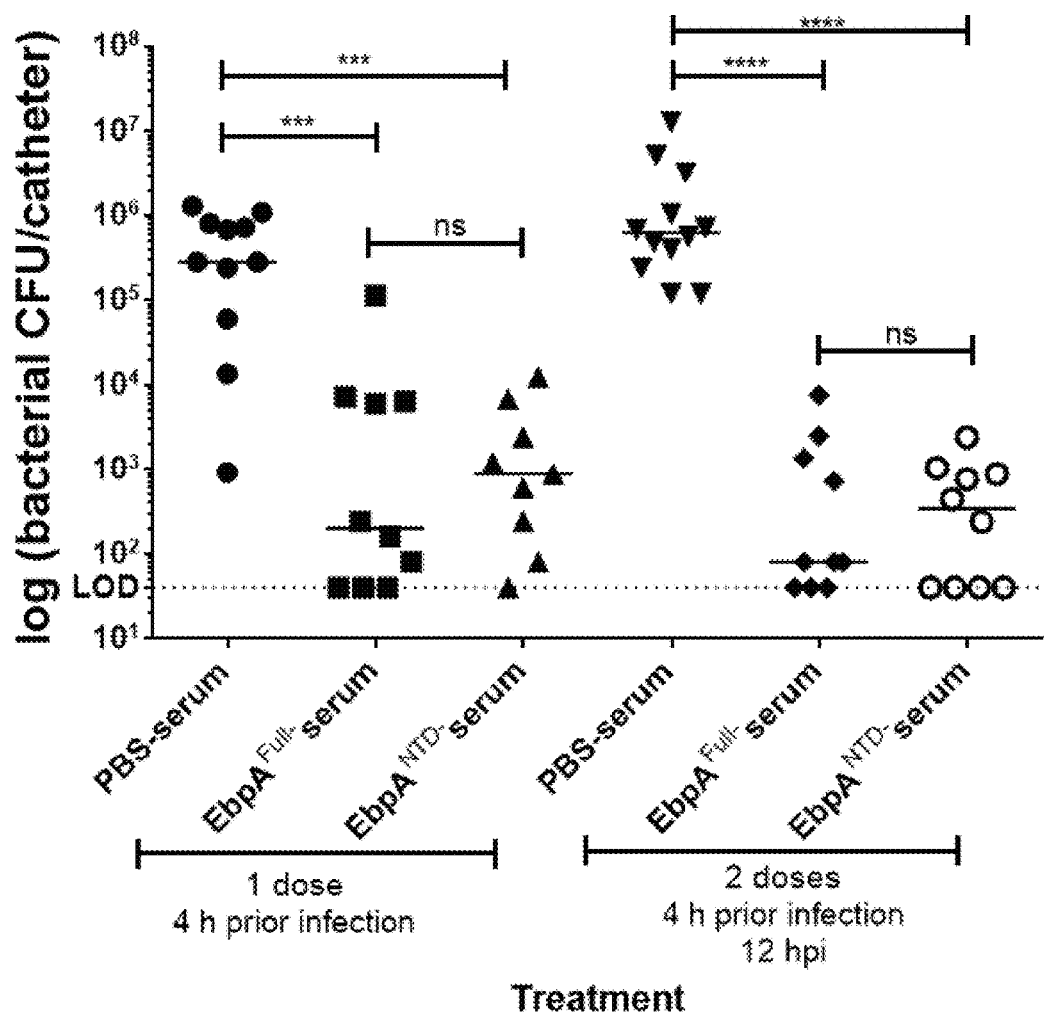

EbpA$^{Full}$ and EbpA$^{NTD}$ Mouse sera Protected Against E. faecalis CAUTI Mice were immunized with EbpA$^{Full}$ or EbpA$^{NTD}$ mouse sera 4 hours prior to catheter implantation and infection with E. faecalis. After 12 hours of infection, a portion of the mice were again immunized with EbpA$^{Full}$ or EbpA$^{NTD}$ mouse sera (FIG. 13A). Then, for all mice, at 24 hours post infection, bacterial burdens in bladder tissue or recovered catheters were quantitated as the number of CFU recovered. A significant reduction in bacterial counts in bladder tissue with ether the single dose or two dose regimen was observed following immunization with EbpA$^{Full}$ or EbpA$^{NTD}$ mouse sera (FIG. 13B). Additionally, a significant reduction in colonization of the catheter with ether the single dose or two dose regimen was observed following immunization with EbpA$^{Full}$ or EbpA$^{NTD}$ sera (FIG. 13C).

Example 7

EbpA$^{NTD}$ Antibodies are Responsible for Reducing Bacteria Titers

Figure 14A:
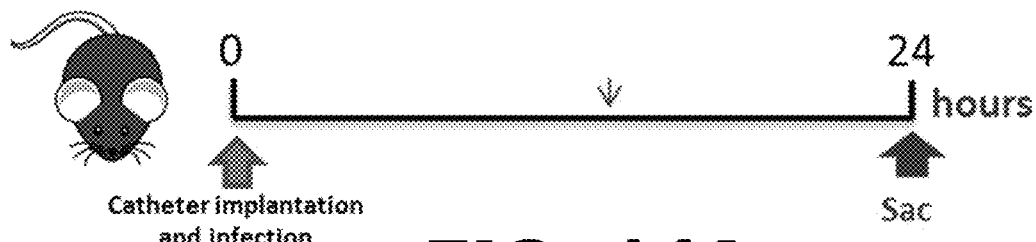
FIG. 14A, FIG. 14B and FIG. 14C depict a schematic and graphs showing EbpA$^{NTD}$ antibodies are responsible for reducing bacteria titers.
Figure 14B:
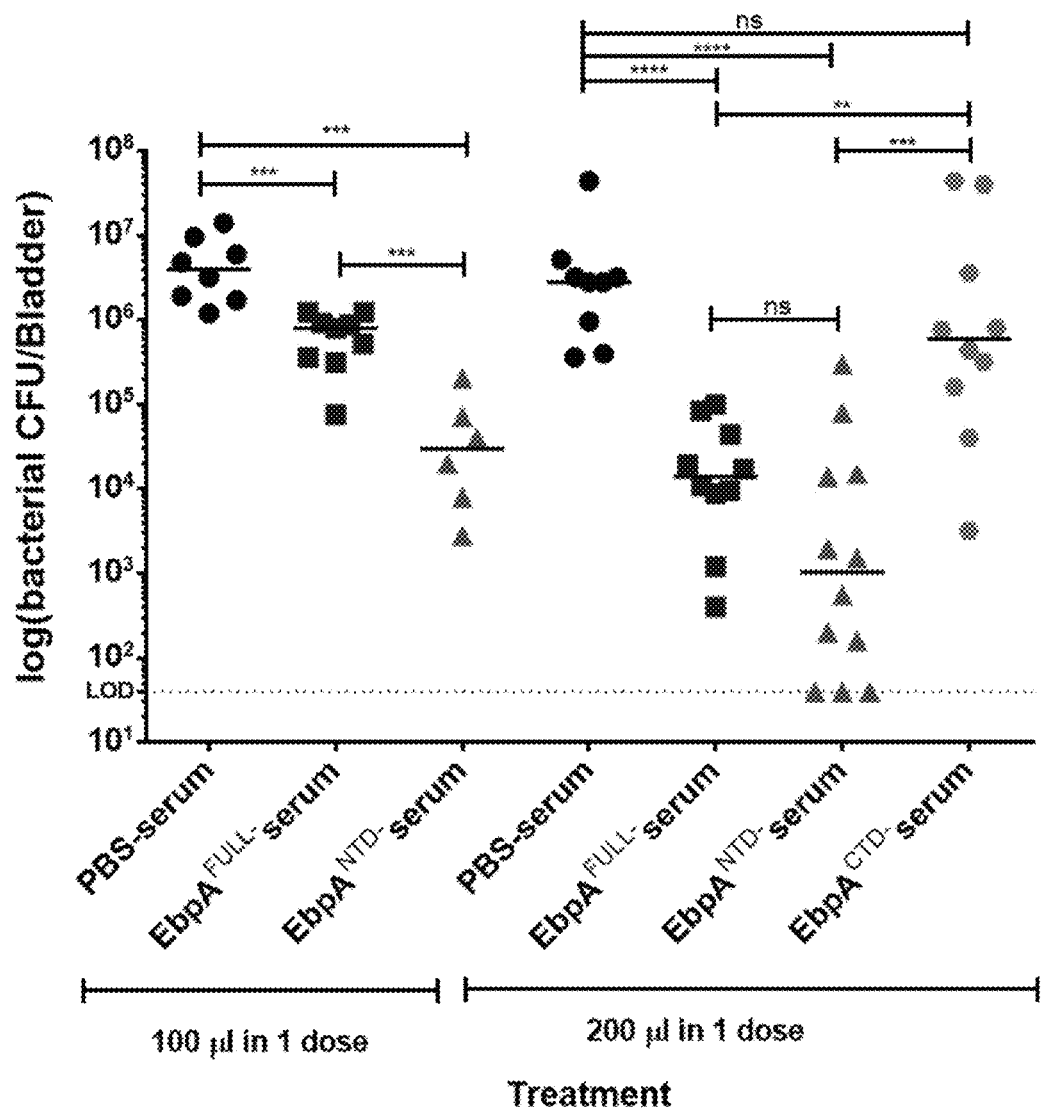
Figure 14C:
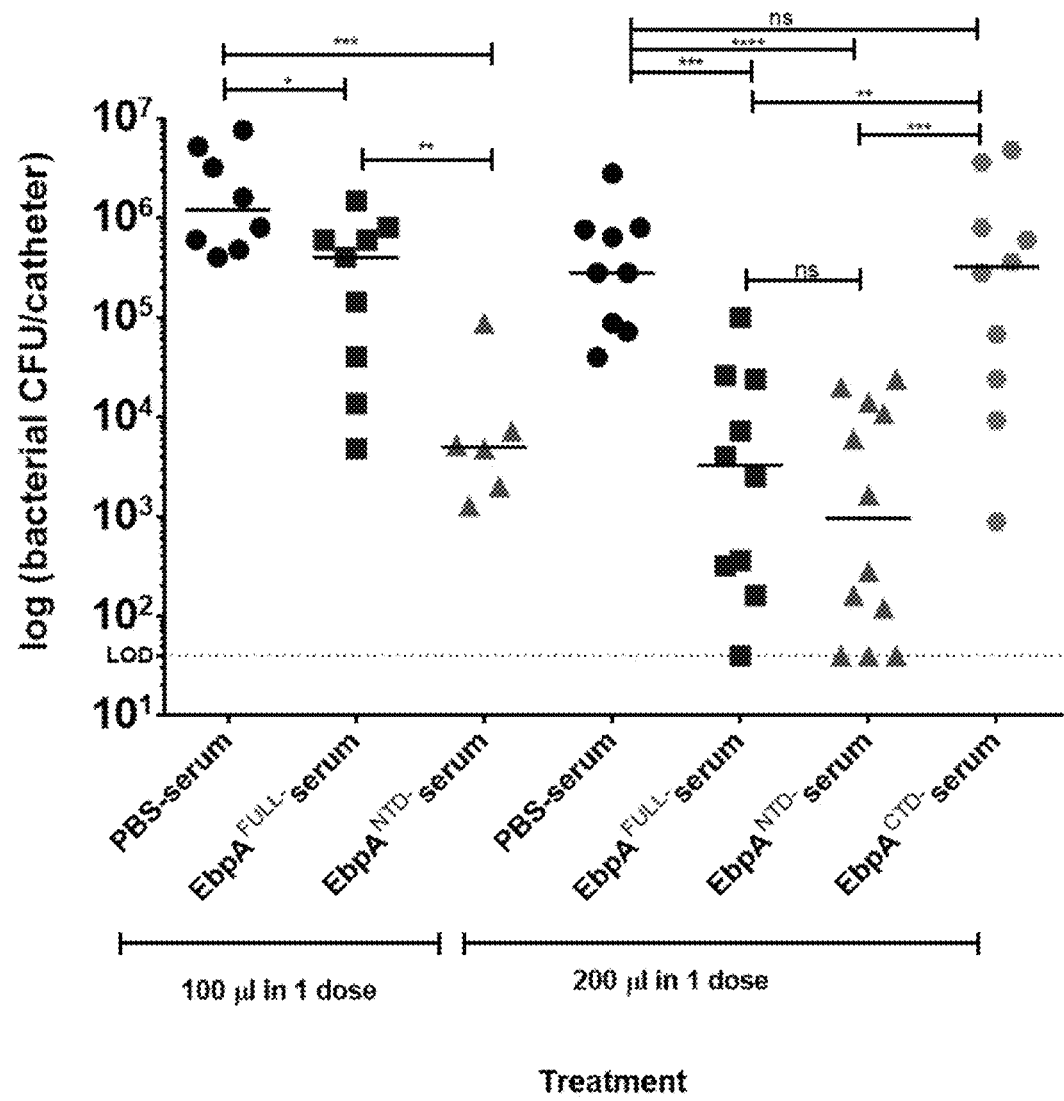

Mice were implanted with catheters and challenged with E. faecalis. After 12 hours of infection, mice were immunized with EbpA$^{Full}$, EbpA$^{NTD}$, or EbpA$^{CTD}$ mouse sera (FIG. 14A). Then, at 24 hours post infection, bacterial burdens in bladder tissue or recovered catheters were quantitated as the number of CFU recovered. A significant reduction in bacterial counts in bladder tissue following immunization with ether the EbpA$^{Full}$ or EbpA$^{NTD}$ mouse sera was observed (FIG. 14B). However, following immunization with EbpA$^{CTD}$ mouse sera no signification reduction in bacterial counts in the bladder was observed (FIG. 14B). The same trend was observed upon evaluation of colonization of the catheter: immunization with EbpA$^{Full}$ or EbpA$^{NTD}$ mouse sera resulted in a significant reduction in colonization of the catheter whereas immunization with EbpA$^{CTD}$ mouse sera did not (FIG. 14C).

Example 8

Vaccination with EbpA$^{NTD}$ Protects Against a Broad Range of Enterococci

Figure 15:
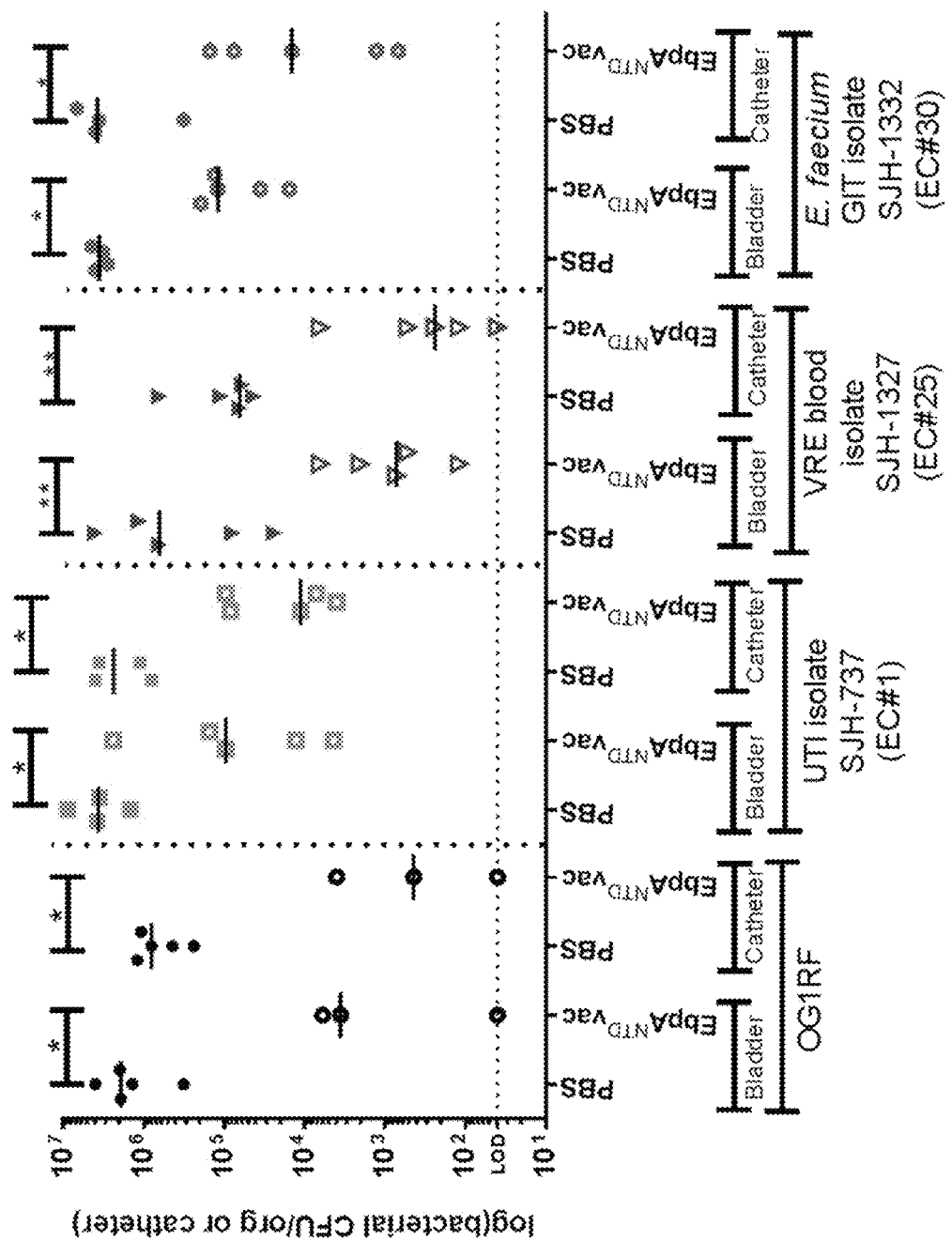
FIG. 15 depicts a graph showing vaccination with EbpA$^{NTD}$ protects against a broad range of enterococci. Vaccination with EbpA$^{NTD}$ prior to infection with various Enterococci clinical isolates resulted in a significant reduction in both bacterial load in the bladder and on the catheter.

Various Enterococci clinical isolates were evaluated in the model described herein. Initially, vaccination with EbpA$^{NTD}$ was performed prior to challenge with Enterococci clinical isolates and catheter implantation. In all cases, vaccination with EbpA$^{NTD}$ significantly reduced bacterial colonization of the bladder tissue and catheter (FIG. 15).

Figure 16A:
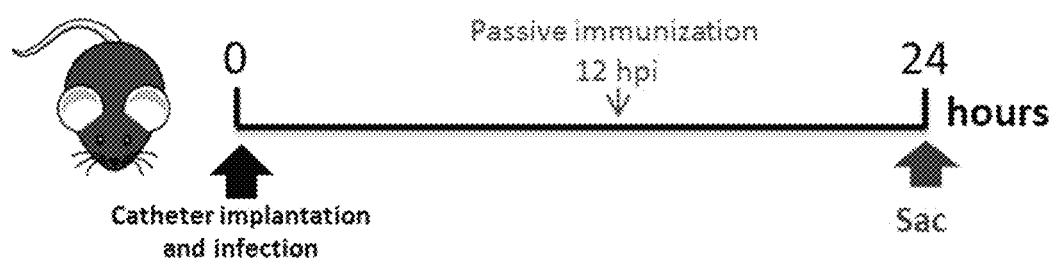
FIG. 16A and FIG. 16B depict a schematic and graph showing EbpA$^{NTD}$ antibodies as therapy against a broad range of enterococci.
Figure 16B:
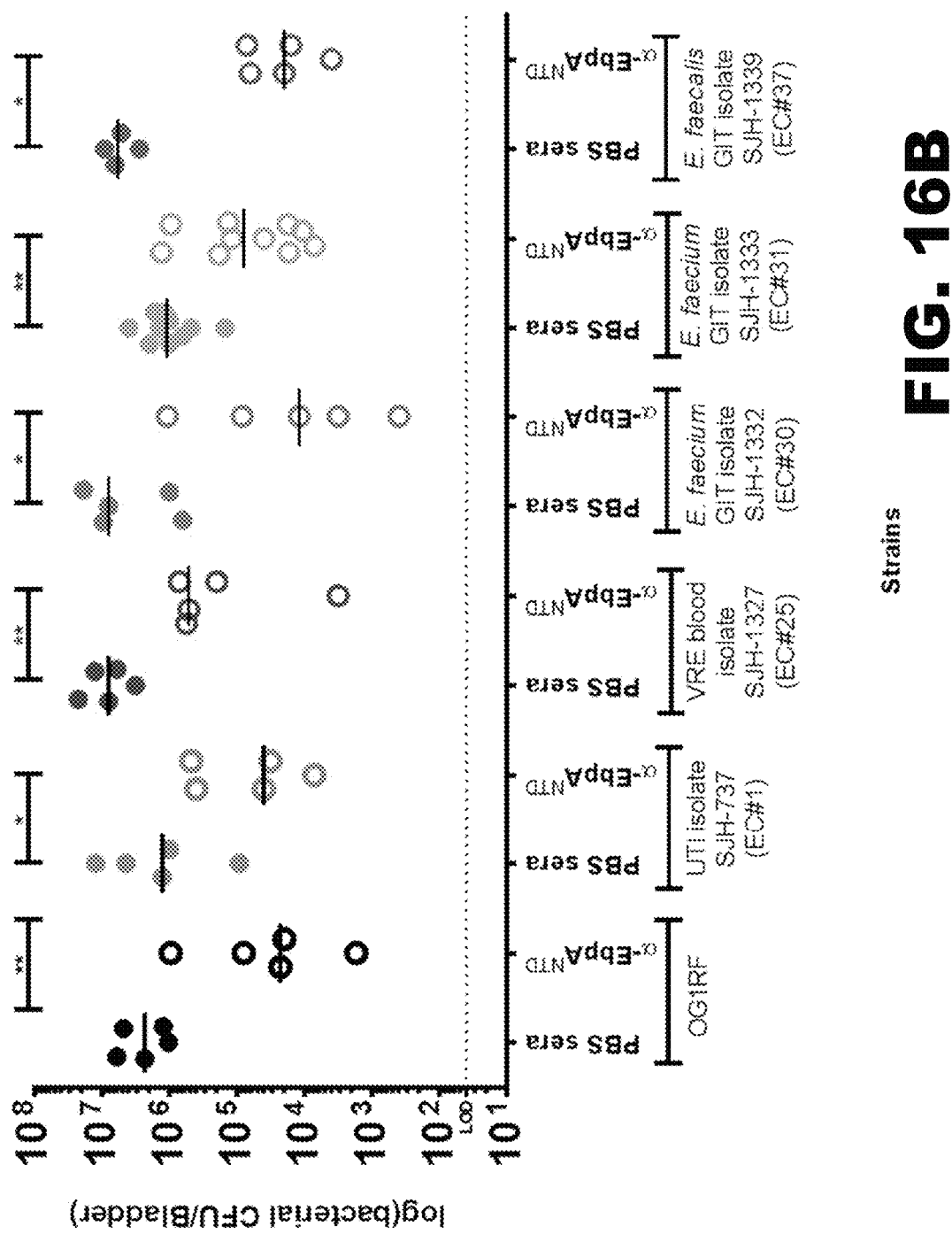
Figure 17:
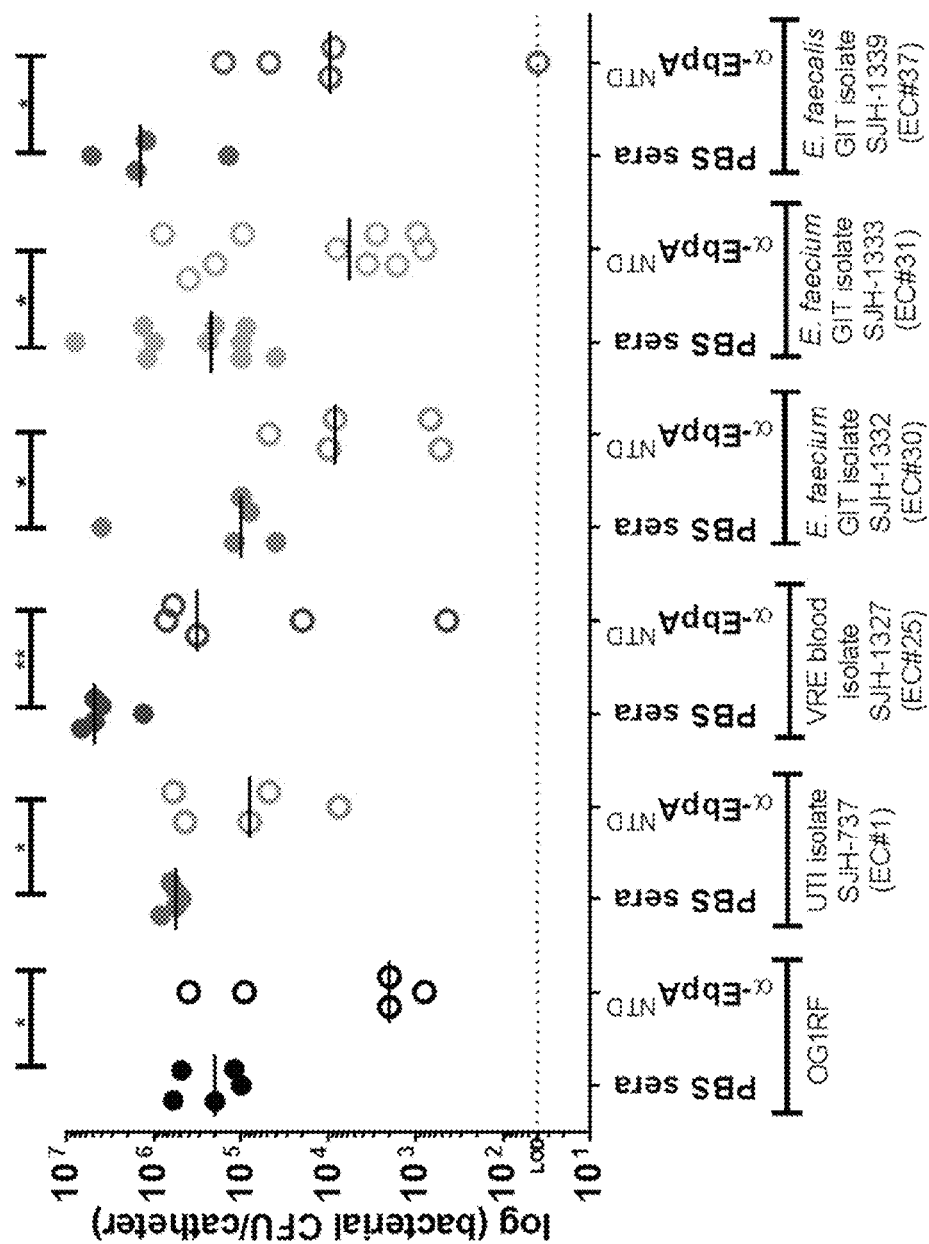
FIG. 17 depicts a graph showing EbpA$^{NTD}$ antibodies as therapy against a broad range of enterococci. The catheters from the experiment depicted in FIG. 16 were also evaluated. In each Enterococci clinical isolate tested, immunization with EbpA$^{NTD}$ mouse sera significantly reduced bacterial colonization of the catheter.

Additionally, mice were implanted with catheters and challenged with various Enterococci clinical isolates. After 12 hours of infection, mice were immunized with EbpA$^{NTD}$ mouse sera (FIG. 16A). Then, at 24 hours post infection, bacterial burdens in bladder tissue or recovered catheters were quantitated as the number of CFU recovered. A significant reduction in bacterial counts in bladder tissue was observed following immunization with EbpA$^{NTD}$ mouse sera in all the Enterococci clinical isolates tested (FIG. 16B). Additionally, a significant reduction in colonization of the catheter was observed following immunization with EbpA$^{NTD}$ sera in all the Enterococci clinical isolates tested (FIG. 17).

TABLE 1

Strains used in this study.

| | Strain identifier | Strain common name (chromosomal antibiotic resistance) | Relevant phenotypic/genotypic characteristics | Plasmid | Ref |
|---|---|---|---|---|---|
| E. faecalis laboratory strains | SJH-1994 | OG1RF (Rif/Fus) | EbpA$^+$, EbpB$^+$, EbpC$^+$, SrtC$^+$, SrtA$^+$ | None | 52 |
| OG1RF chromosomal deletion mutants | SJH-953 | ΔsrtA (Rif/Fus) | EbpA$^+$, EbpB$^+$, EbpC$^+$, SrtC$^+$, SrtA$^-$ | None | 53 |
| | SJH-1421 | ΔebpC (Rif/Fus) | EbpA$^+$, EbpB$^+$, EbpC$^-$, SrtC+, SrtA$^+$ | None | 54 |
| | SJH-1995 | ΔebpABCΔsrtC (Rif/Fus) | EbpA$^-$, EbpB$^-$, EbpC$^-$, SrtC$^-$, SrtA$^+$ | None | 54 |
| | SJH-1996 | ΔebpA(Rif/Fus) | EbpA$^-$, EbpB$^+$, EbpC$^+$, SrtC$^+$, SrtA$^+$ | None | 54 |
| | SJH-2000 | ΔebpAB (Rif/Fus) | EbpA$^-$, EbpB$^-$, EbpC$^+$, SrtC$^+$, SrtA$^+$ | None | 54 |
| | SJH-2001 | ebpA$^{AWAGA}$ $^{(SEQ\ ID\ NO:\ 1)}$ (Rif/Fus) | EbpAD315A, S317A, S319A EbpB$^+$, EbpC$^+$, SrtC$^+$, SrtA+ | None | 54 |
| Commercial E. coli expression strains | SJH-1889 | M15/pREP4 | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4 | Qiagen |
| | SJH-1890 | SG13009/pREP4 | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4 | Qiagen |
| E. coli strains expressing recombinant Ebp proteins | SJH-1987 | M15 (pREP4) (pQE-30Xa-6xHis-ebpA$^{CTD}$) | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4, pSJH-541 | 54 |
| | SJH-1988 | M15 (pREP4) (pQE-30Xa-6xHis-ebpB) | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4, pSJH-547 | 54 |
| | SJH-1985 | SG13009 (pREP4) (pQE-30Xa -6xHis-ebpC) | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4, pSJH-550 | 54 |
| | SJH-2610 | M15 (pREP4) (pQE-30Xa-6xHis-ebpA$^{Full}$) | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon$^+$ | pREP4, pSJH-687 | This study |
| | SJH-2611 | M15 (pREP4) (pQE-30Xa-6xHis-ebpA$^{AWAGA}$ $^{(SEQ\ ID\ NO:\ 1)}$) | Nal$^S$, Str$^S$, Rif$^S$, Thi$^-$, Lac-, Ara$^+$, Gal$^+$, Mtl$^-$, F$^-$, RecA+, Uvr$^+$, Lon$^+$ | pREP4, pSJH-688 | This study |

TABLE 1-continued

Strains used in this study.

| Strain identifier | Strain common name (chromosomal antibiotic resistance) | Relevant phenotypic/genotypic characteristics | Plasmid | Ref |
|---|---|---|---|---|
| SJH-2612 | M15 (pREP4) (pQE-30Xa-6xHis-ebpA$^{NTD}$) | Nal$^S$, Str$^S$, Rif$^S$, Thi$^-$, Lac$^-$, Ara$^+$, Gal$^+$, Mtl$^-$, F$^-$, RecA$^+$, Uvr$^+$, Lon+ | pREP4, pSJH-689 | This study |

TABLE 2

Plasmids used in this study.

| | Plasmid identifier | Plasmid name | Method used to generate the plasmid | Parent plasmid | Antibiotic resistance | Ref |
|---|---|---|---|---|---|---|
| Commercial vectors | n/a | pREP4 | | n/a | Kan | Qiagen |
| | n/a | pQE-30Xa | | n/a | Kan | Qiagen |
| Plasmids | pSJH-541 | pQE-30Xa-ebpA$^{CTD}$ | Ligation using BamHI and SalI | pQE-30Xa | Amp | 54 |
| | pSJH-547 | pQE-30Xa-ebpB | Ligation using SphI and PstI | pQE-30Xa | Amp | 54 |
| | pSJH-550 | pQE-30Xa-ebpC | Ligation using BamHI and SacI | pQE-30Xa | Amp | 54 |
| | pSJH-687 | pQE-30Xa-ebpAFull | Ligation using BamHI and NheI | pQE-30Xa | Amp | This study |
| | pSJH-688 | pQE-30Xa-ebpAAWAGA | Ligation using BamHI and NheI | pQE-30Xa | Amp | This study |
| | pSJH-689 | pQE-30Xa-ebpA$^{NTD}$ | Ligation using EcoRV | pQE-30Xa | Amp | This study |

TABLE 3

Primers used in this study.

| | Primer name | Primer sequence (5'- to -3')* | Description | Restriction sites | Ref |
|---|---|---|---|---|---|
| Primers used to generate E. coli expression constructs | ALFM01 | 5'-CGCGGATCCATAACAGTAGAGGATTCTGCTAAA-3' (SEQ ID NO: 6) | Forward primer for amplifying ebpA$^{Full}$ and ebpA$^{AWAGA}$ (SEQ ID NO: 1) PCR fragments | BamHI | This study |
| | ALFM02 | 5'-CTAGCTAGCTTAACCAGTTTCAGGTAAAGGAACC-3' (SEQ ID NO: 7) | Reverse primer for amplifying ebpA$^{Full}$ and ebpA$^{AWAGA}$ PCR fragments | NheI | This study |
| | ALFM51 | 5'-CCGGATATCTCATCATCATCGTACTTGATAATGAATTTGAAT-3' (SEQ ID NO: 8) | Reverse primer for amplifying ebpA$^{NTD}$ PCR fragments | EcoRV | This study |
| | ALFM52 | 5'-CCGGATATCAGGGGTTAAAAGAACCAATCGAATTAATAA-3' (SEQ ID NO: 9) | Forward primer for amplifying ebpA$^{NTD}$ PCR fragments | EcoRV | This study |
| | HVN114 | 5'-GCGGGATCCATGAATGGTCGGACAACGTTTCAGCC-3' (SEQ ID NO: 10) | Forward primer for amplifying ebpA$^{CTD}$ PCR fragments | BamHI | 54 |
| | HVN117 | 5'-CCGTCGACTTACAAGCGTCCTATGCCA | Reverse primer for amplifying ebpA$^{CTD}$ | SalI | 54 |

TABLE 3-continued

Primers used in this study.

| Primer name | Primer sequence (5'- to -3')* | Description | Restriction sites | Ref |
|---|---|---|---|---|
| | CCAGTTTCAGG-3' (SEQ ID NO: 11) | PCR fragments | | |

*Restriction site is indicated in underline

References for the Examples

1. Parker D, Callan L, Harwood J, Thompson D L, Wilde M, Gray M. Nursing interventions to reduce the risk of catheter-associated urinary tract infection. Part 1: Catheter selection. J Wound Ostomy Continence Nurs. 2009; 36:23-34.
2. Maki D G, Tambyah P A. Engineering out the risk for infection with urinary catheters. Emerg Infect Dis.2001; 7:342-347.
3. Willson M, Wilde M, Webb M L, Thompson D, Parker D, Harwood J, Callan L, Gray M. Nursing interventions to reduce the risk of catheter-associated urinary tract infection: Part 2: Staff education, monitoring, and care techniques. J Wound Ostomy Continence Nurs. 2009;36:137-154.
4. Nicolle L E. The chronic indwelling catheter and urinary infection in long-term-care facility residents.Infect Control Hosp Epidemiol. 2001;22:316-321.
5. Hidron A I, Edwards J R, Patel J, Horan T C, Sievert D M, Pollock D A, Fridkin S K, National Healthcare Safety Network Team; Participating National Healthcare Safety Network Facilities NHSN annual update: Antimicrobial-resistant pathogens associated with healthcare-associated infections: Annual summary of data reported to the National Healthcare Safety Network at the Centers for Disease Control and Prevention, 2006-2007. Infect Control Hosp Epidemiol. 2008;29:996-1011.
6. Arias C A, Murray B E. Emergence and management of drug-resistant enterococcal infections. Expert Rev Anti Infect Ther. 2008;6:637-655.
7. Cusumano C K, Hultgren S J. Bacterial adhesion—A source of alternate antibiotic targets. IDrugs.2009;12:699-705.
8. Arias C A, Murray B E. The rise of the Enterococcus: Beyond vancomycin resistance. Nat Rev Microbio1.2012; 10:266-278.
9. Cardoso T, Ribeiro O, Aragão IC, Costa-Pereira A, Sarmento A E. Additional risk factors for infection by multidrug-resistant pathogens in healthcare-associated infection: A large cohort study. BMC Infect Dis.2012;12: 375.
10. Paganelli F L, Willems R J, Leavis H L. Optimizing future treatment of enterococcal infections: Attacking the biofilm? Trends Microbiol. 2012;20:40-49.
11. Parker D, Callan L, Harwood J, Thompson D, Webb M L, Wilde M, Willson M. Clinical Practice Continence Subcommittee, Catheter-associated urinary tract infections: Fact sheet. J Wound Ostomy Continence Nurs. 2009;36:156-159.
12. Guiton P S, Hannan T J, Ford B, Caparon M G, Hultgren S J. Enterococcus faecalis overcomes foreign body-mediated inflammation to establish urinary tract infections. Infect Immun. 2012;81:329-339.
13. Lebreton F, Le Bras F, Reffuveille F, Ladjouzi R, Giard J C, Leclercq R, Cattoir V. Galleria mellonella as a model for studying Enterococcus faecium host persistence. J Mol Microbiol Biotechnol. 2011;21:191-196.
14. Guiton P S, Hung C S, Hancock L E, Caparon M G, Hultgren S J. Enterococcal biofilm formation and virulence in an optimized murine model of foreign body-associated urinary tract infections. Infect Immun.2010; 78:4166-4175.
15. Nallapareddy S R, Singh K V, Sillanpää J, Garsin D A, Höök M, Erlandsen S L, Murray B E. Endocarditis and biofilm-associated pili of Enterococcus faecalis. J Clin Invest. 2006;116:2799-2807.
16. Nallapareddy S R, Singh K V, Sillanpää J, Zhao M, Murray B E. Relative contributions of Ebp pili and the collagen adhesin ace to host extracellular matrix protein adherence and experimental urinary tract infection by Enterococcus faecalis OG1 RF. Infect Immun. 2011;79: 2901-2910.
17. Singh K V, Nallapareddy S R, Murray B E. Importance of the ebp (endocarditis- and biofilm-associated pilus) locus in the pathogenesis of Enterococcus faecalis ascending urinary tract infection. J Infect Dis.2007;195: 1671-1677.
18. Nielsen H V, Guiton P S, Kline K A, Port G C, Pinkner J S, Neiers F, Normark S, Henriques-Normark B, Caparon M G, Hultgren S J. The metal ion-dependent adhesion site motif of the Enterococcus faecalis EbpA pilin mediates pilus function in catheter-associated urinary tract infection. MBio. 2012;3:e00177-12.
19. Nielsen H V, Flores-Mireles A L, Kau A L, Kline K A, Pinkner J S, Neiers F, Normark S, Henriques-Normark B, Caparon M G, Hultgren S J. Pilin and sortase residues critical for endocarditis- and biofilm-associated pilus biogenesis in Enterococcus faecalis. J Bacteriol. 2013;195: 4484-4495.
20. Sillanpää J, Chang C, Singh K V, Montealegre M C, Nallapareddy S R, Harvey B R, Ton-That H, Murray B E. Contribution of individual Ebp pilus subunits of Enterococcus faecalis OG1 RF to pilus biogenesis, biofilm formation and urinary tract infection. PLOS One. 2013; 8:e68813.
21. Murcia M, Jirouskova M, Li J, Caller B S, Filizola M. Functional and computational studies of the ligand-associated metal binding site of β3 integrins. Proteins. 2008; 71:1779-1791.
22. Vaidyanathan S, Soni B M, Bingley J, Brown E, Markey S. Prevention of pressure sore caused by indwelling urinary catheters. Spinal Cord. 2002;40:489.
23. Peychl L, Zalud R. Changes in the urinary bladder caused by short-term permanent catheter insertion.Cas Lek Cesk. 2008;147:325-329.
24. Vaidyanathan S, Mansour P, Ueno M, Yamazaki K, Wadhwa M, Soni B M, Singh G, Hughes P L, Watson I D, Sett P. Problems in early diagnosis of bladder cancer in a 25. Davalos D, Akassoglou K. Fibrinogen as a key regulator of inflammation in disease. Semin Immunopathol. 2012; 34:43-62.
26. Jennewein C, Tran N, Paulus P, Ellinghaus P, Eble J A, Zacharowski K. Novel aspects of fibrin(ogen) fragments during inflammation. Mol Med. 2011;17:568-573.
27. Hannan T J, Mysorekar I U, Hung C S, Isaacson-Schmid M L, Hultgren S J. Early severe inflammatory responses to uropathogenic *E. coli* predispose to chronic and recurrent urinary tract infection. PLOS Pathog.2010;6: e1001042.
28. van Opijnen T, Camilli A. A fine scale phenotype—genotype virulence map of a bacterial pathogen.Genome Res. 2012;22:2541-2551.
29. Ernst E, Koenig W. Fibrinogen and cardiovascular risk. Vasc Med. 1997;2:115-125.
30. Zandbergen F, Plutzky J. PPARα in atherosclerosis and inflammation. Biochim Biophys Acta.2007;1771:972-982.
31. Sarwar N, Thompson A J, Di Angelantonio E. Markers of inflammation and risk of coronary heart disease. Dis Markers. 2009;26:217-225.
32. Mosesson M W. Fibrinogen and fibrin structure and functions. J Thromb Haemost. 2005;3:1894-1904.
33. Ackland P. Prevalence, detection, evaluation and management of chronic kidney disease. BMJ.2014;348:f7688.
34. Currie G, Delles C. Proteinuria and its relation to cardiovascular disease. Int J Nephrol Renovasc Dis.2013; 7:13-24.
35. Snyder S, Pendergraph B. Detection and evaluation of chronic kidney disease. Am Fam Physician.2005;72: 1723-1732.
36. Odetoyin W B, Aboderin AO, Ikem R T, Kolawole B A, Oyelese A O. Asymptomatic bacteriuria in patients with diabetes mellitus in Ile-Iffe, South-West Nigeria. East Afr Med J. 2008;85:18-23.
37. Szczepańska M, Szprynger K, Adamczyk P. Effect of urinary tract infections in children with chronic renal failure on peritoneal dialysis. Pol Merkur Lekarski. 2004; 16:223-227.
38. Presterl E, Bognar H, Winkler S, Thalhammer F, Georgopoulos A, Hoffmann W, Breyer S. Sequential parenteral and oral therapy with ofloxacin in urogenital infections. Wien Med Wochenschr. 1992;142:381-385.
39. Khudaier B Y, Tewari R, Shafiani S, Sharma M, Emmanuel R, Sharma M, Taneja N. Epidemiology and molecular characterization of vancomycin resistant Enterococci isolates in India. Scand J Infect Dis.2007;39: 662-670.
40. Guiton P S, Hung C S, Kline K A, Roth R, Kau A L, Hayes E, Heuser J, Dodson K W, Caparon M G, Hultgren S J. Contribution of autolysin and sortase a during *Enterococcus faecalis* DNA-dependent biofilm development. Infect Immun. 2009;77:3626-3638.
41. Webb J S, Van der Mei H C, Nixon M, Eastwood I M, Greenhalgh M, Read S J, Robson G D, Handley P S. Plasticizers increase adhesion of the deteriogenic fungus Aureobasidium pullulans to polyvinyl chloride.Appl Environ Microbiol. 1999;65:3575-3581.
42. Iwanaga S, Gokudan S, Mizuguchi J. In: Recent Advances in Thrombosis and Hemostasis 2008. Tanaka K, Davie E, Ikeda Y, Iwanaga S, Saito H, Sueishi K, editors. Springer; Japan, Tokyo: 2008. pp. 439-461. chap. 31.
43. Delnay K M, Stonehill W H, Goldman H, Jukkola A F, Dmochowski R R. Bladder histological changes associated with chronic indwelling urinary catheter. J Urol. 1999;161:1106-1108. discussion 1108-1109.
44. Liedberg H. Catheter induced urethral inflammatory reaction and urinary tract infection. An experimental and clinical study. Scand J Urol Nephrol Suppl. 1989;124:1-43.
45. Kurosaka Y, Ishida Y, Yamamura E, Takase H, Otani T, Kumon H. A non-surgical rat model of foreign body-associated urinary tract infection with *Pseudomonas aeruginosa*. Microbiol Immunol. 2001;45:9-15.
46. Pinkston K L, Singh K V, Gao P, Wilganowski N, Robinson H, Ghosh S, Azhdarinia A, Sevick-Muraca E M, Murray B E, Harvey B R. Targeting pili in enterococcal pathogenesis. Infect Immun. 2014;82:1540-1547.
47. Mount D W. Using the Basic Local Alignment Search Tool (BLAST) CSH Protoc 2007, pdb top17.2007
48. Altschul S F, Gish W, Miller W, Myers E W, Lipman D J. Basic local alignment search tool. J Mol Biol.1990; 215:403-410.
49. Kelley L A, Sternberg M J E. Protein structure prediction on the Web: A case study using the Phyre server.Nat Protoc. 2009;4:363-371.
50. Hung C S, Dodson K W, Hultgren S J. A murine model of urinary tract infection. Nat Protoc.2009;41 230-1243.
51. Langermann S, Palaszynski S, Barnhart M, Auguste G, Pinkner JS, Burlein J, Barren P, Koenig S, Leath S, Jones CH, Hultgren SJ. Prevention of mucosal *Escherichia coli* infection by FimH-adhesin-based systemic vaccination. Science. 1997;276:607-611.
52. Dunny G M, Brown B L, Clewell D B. Induced cell aggregation and mating in *Streptococcus faecalis*: Evidence for a bacterial sex pheromone. Proc Natl Acad Sci USA. 1978;75:3479-3483.
53. Guiton P S, Hung C S, Kline K A, Roth R, Kau A L, Hayes E, Heuser J, Dodson K W, Caparon M G, Hultgren S J. Contribution of autolysin and Sortase a during *Enterococcus faecalis* DNA-dependent biofilm development. Infection and immunity. 2009;77:3626-3638.
54. Nielsen H V, Guiton P S, Kline K A, Port G C, Pinkner J S, Neiers F, Normark S, Henriques-Normark B, Caparon M G, Hultgren S J. The metal ion-dependent adhesion site motif of the *Enterococcus faecalis* EbpA pilin mediates pilus function in catheter-associated urinary tract infection. MBio. 2012;3:e00177-00112.

What is claimed is:

1. A method of treating an EbpA-associated infection in a subject, the method comprising administering to the subject an effective amount of a vaccine composition comprising SEQ ID NO:3.

2. The method of claim 1, wherein the EbpA-associated infection is a catheter-associated urinary tract infection (CAUTI).

3. The method of claim 2, wherein the CAUTI is *Enterococcus* mediated.

4. The method of claim 3, wherein the *Enterococcus* is *E. faecalis*.

5. The method of claim 1, wherein the vaccine composition is administered at a dose ranging from 0.3 to 100 µg.

6. The method of claim 1, wherein the vaccine composition is administered every 2 to 4 weeks.

7. The method of claim 1, wherein the vaccine composition is administered intramuscularly.

8. The method of claim 1, further comprising administering an antimicrobial agent.

9. The method of claim 1, wherein the vaccine composition disrupts the interaction between EbpA and fibrinogen.

10. The method of claim 1, wherein the vaccine composition comprises more than one SEQ ID NO: 3 linked together.

11. The method of claim 1, wherein SEQ ID NO:3 comprises a fibrinogen-binding domain.

12. The method of claim 1, wherein the vaccine composition comprises an immune effective amount of adjuvant selected from the group consisting of an aluminum salt, calcium salt, iron, zinc, acylated tyrosine, acylated sugars, saccharide, polyphoshazenes, biodegradable microspheres, monophosporyl lipid A, lipid A derivatives quit A, Saponin, QS21, Freund's Incomplete Adjuvant, Merck Adjuvant 65, AS-2, CpG oligonucleotides, bioadhesives and mucoadhesives, microparticles, liposomes, polyoxyethyene ether formulations, polyoxyethylene ester formulations, muramyl peptides or imidazoquinolone compounds.

* * * * *

SEQUENCE LISTING

<160> NUMBER OF SEQ ID NOS: 11

<210> SEQ ID NO 1
<211> LENGTH: 5
<212> TYPE: PRT
<213> ORGANISM: Enterococcus faecalis

<400> SEQUENCE: 1

Ala Trp Ala Gly Ala
1               5

<210> SEQ ID NO 2
<211> LENGTH: 5
<212> TYPE: PRT
<213> ORGANISM: Enterococcus faecalis

<400> SEQUENCE: 2

Asp Trp Ser Gly Ser
1               5

<210> SEQ ID NO 3
<211> LENGTH: 463
<212> TYPE: PRT
<213> ORGANISM: Enterococcus faecalis

<400> SEQUENCE: 3

Pro Glu Lys Ile Thr Val Pro Glu Asn Thr Lys Glu Thr Asn Lys Asn
1               5                   10                  15

Asp Ser Ala Pro Glu Lys Thr Glu Gln Pro Thr Ala Thr Glu Glu Val
            20                  25                  30

Thr Asn Pro Phe Ala Glu Ala Arg Met Ala Pro Ala Thr Leu Arg Ala
        35                  40                  45

Asn Leu Ala Leu Pro Leu Ile Ala Pro Gln Tyr Thr Thr Asp Asn Ser
    50                  55                  60

Gly Thr Tyr Pro Thr Ala Asn Trp Gln Pro Gly Asn Gln Asn Val
65                  70                  75                  80

Leu Asn His Gln Gly Asn Lys Asp Gly Ser Ala Gln Trp Asp Gly Gln
                85                  90                  95

Thr Ser Trp Asn Gly Asp Pro Thr Asn Arg Thr Asn Ser Tyr Ile Glu
            100                 105                 110

Tyr Gly Gly Thr Gly Asp Gln Ala Asp Tyr Ala Ile Arg Lys Tyr Ala
        115                 120                 125

Arg Glu Thr Thr Thr Pro Gly Leu Phe Asp Val Tyr Leu Asn Val Arg
    130                 135                 140

Gly Asn Val Gln Lys Glu Ile Thr Pro Leu Asp Leu Val Leu Val Val
145                 150                 155                 160

Asp Trp Ser Gly Ser Met Asn Glu Asn Asn Arg Ile Gly Glu Val Gln
                165                 170                 175

Lys Gly Val Asn Arg Phe Val Asp Thr Leu Ala Asp Ser Gly Ile Thr
            180                 185                 190

Asn Asn Ile Asn Met Gly Tyr Val Gly Tyr Ser Ser Asp Gly Tyr Asn
        195                 200                 205

Asn Asn Ala Ile Gln Met Gly Pro Phe Asp Thr Val Lys Asn Pro Ile
    210                 215                 220

Lys Asn Ile Thr Pro Ser Ser Thr Arg Gly Gly Thr Phe Thr Gln Lys
225                 230                 235                 240

Ala Leu Arg Asp Ala Gly Asp Met Leu Ala Thr Pro Asn Gly His Lys
                245                 250                 255

Lys Val Ile Val Leu Leu Thr Asp Gly Val Pro Thr Phe Ser Tyr Lys
            260                 265                 270

Val Ser Arg Val Gln Thr Glu Ala Asp Gly Arg Phe Tyr Gly Thr Gln
        275                 280                 285

```
Phe Thr Asn Arg Gln Asp Gln Pro Gly Ser Thr Ser Tyr Ile Ser Gly
    290                 295                 300

Ser Tyr Asn Ala Pro Asp Gln Asn Asn Ile Asn Lys Arg Ile Asn Ser
305                 310                 315                 320

Thr Phe Ile Ala Thr Ile Gly Glu Ala Met Ala Leu Lys Gln Arg Gly
                325                 330                 335

Ile Glu Ile His Gly Leu Gly Ile Gln Leu Gln Ser Asp Pro Arg Ala
                340                 345                 350

Asn Leu Ser Lys Gln Gln Val Glu Asp Lys Met Arg Glu Met Val Ser
            355                 360                 365

Ala Asp Glu Asn Gly Asp Leu Tyr Tyr Glu Ser Ala Asp Tyr Ala Pro
370                 375                 380

Asp Ile Ser Asp Tyr Leu Ala Lys Lys Ala Val Gln Ile Ser Gly Thr
385                 390                 395                 400

Val Val Asn Gly Lys Val Val Asp Pro Ile Ala Glu Pro Phe Lys Tyr
                405                 410                 415

Glu Pro Asn Thr Leu Ser Met Lys Ser Val Gly Pro Val Gln Val Gln
                420                 425                 430

Thr Leu Pro Glu Val Ser Leu Thr Gly Ala Thr Ile Asn Ser Asn Glu
                435                 440                 445

Ile Tyr Leu Gly Lys Gly Gln Glu Ile Gln Ile His Tyr Gln Val
450                 455                 460
```

```
<210> SEQ ID NO 4
<211> LENGTH: 5
<212> TYPE: PRT
<213> ORGANISM: Enterococcus faecalis
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 4

Asp Xaa Ser Xaa Ser
1               5

<210> SEQ ID NO 5
<211> LENGTH: 1102
<212> TYPE: PRT
<213> ORGANISM: Enterococcus faecalis

<400> SEQUENCE: 5

Met Ile Thr Asp Glu Asn Asp Lys Thr Asn Ile Asn Ile Glu Leu Asn
1               5                   10                  15

Leu Leu Asn Gln Thr Glu Gln Pro Leu Gln Arg Glu Ile Gln Leu Lys
            20                  25                  30

Asn Ala Gln Phe Met Asp Thr Ala Val Ile Glu Lys Asp Gly Tyr Ser
        35                  40                  45

Tyr Gln Val Thr Asn Gly Thr Leu Tyr Leu Thr Leu Asp Ala Gln Val
50                  55                  60

Lys Lys Pro Val Gln Leu Ser Leu Ala Val Glu Gln Ser Ser Leu Gln
65                  70                  75                  80

Thr Ala Gln Pro Pro Lys Leu Leu Tyr Glu Asn Asn Glu Tyr Asp Val
                85                  90                  95

Ser Val Thr Ser Glu Lys Ile Thr Val Glu Asp Ser Ala Lys Glu Ser
```

-continued

```
              100                 105                 110
Thr Glu Pro Glu Lys Ile Thr Val Pro Glu Asn Thr Lys Glu Thr Asn
              115                 120                 125
Lys Asn Asp Ser Ala Pro Glu Lys Thr Glu Gln Pro Thr Ala Thr Glu
              130                 135                 140
Glu Val Thr Asn Pro Phe Ala Glu Ala Arg Met Ala Pro Ala Thr Leu
145                 150                 155                 160
Arg Ala Asn Leu Ala Leu Pro Leu Ile Ala Pro Gln Tyr Thr Thr Asp
                      165                 170                 175
Asn Ser Gly Thr Tyr Pro Thr Ala Asn Trp Gln Pro Thr Gly Asn Gln
                  180                 185                 190
Asn Val Leu Asn His Gln Gly Asn Lys Asp Gly Ser Ala Gln Trp Asp
                  195                 200                 205
Gly Gln Thr Ser Trp Asn Gly Asp Pro Thr Asn Arg Thr Asn Ser Tyr
              210                 215                 220
Ile Glu Tyr Gly Gly Thr Gly Asp Gln Ala Asp Tyr Ala Ile Arg Lys
225                 230                 235                 240
Tyr Ala Arg Glu Thr Thr Thr Pro Gly Leu Phe Asp Val Tyr Leu Asn
                      245                 250                 255
Val Arg Gly Asn Val Gln Lys Glu Ile Thr Pro Leu Asp Leu Val Leu
                  260                 265                 270
Val Val Asp Trp Ser Gly Ser Met Asn Glu Asn Asn Arg Ile Gly Glu
                  275                 280                 285
Val Gln Lys Gly Val Asn Arg Phe Val Asp Thr Leu Ala Asp Ser Gly
              290                 295                 300
Ile Thr Asn Asn Ile Asn Met Gly Tyr Val Gly Tyr Ser Ser Asp Gly
305                 310                 315                 320
Tyr Asn Asn Asn Ala Ile Gln Met Gly Pro Phe Asp Thr Val Lys Asn
                      325                 330                 335
Pro Ile Lys Asn Ile Thr Pro Ser Ser Thr Arg Gly Gly Thr Phe Thr
                  340                 345                 350
Gln Lys Ala Leu Arg Asp Ala Gly Asp Met Leu Ala Thr Pro Asn Gly
                  355                 360                 365
His Lys Lys Val Ile Val Leu Leu Thr Asp Gly Val Pro Thr Phe Ser
              370                 375                 380
Tyr Lys Val Ser Arg Val Gln Thr Glu Ala Asp Gly Arg Phe Tyr Gly
385                 390                 395                 400
Thr Gln Phe Thr Asn Arg Gln Asp Gln Pro Gly Ser Thr Ser Tyr Ile
                      405                 410                 415
Ser Gly Ser Tyr Asn Ala Pro Asp Gln Asn Asn Ile Asn Lys Arg Ile
                  420                 425                 430
Asn Ser Thr Phe Ile Ala Thr Ile Gly Glu Ala Met Ala Leu Lys Gln
                  435                 440                 445
Arg Gly Ile Glu Ile His Gly Leu Gly Ile Gln Leu Gln Ser Asp Pro
              450                 455                 460
Arg Ala Asn Leu Ser Lys Gln Gln Val Glu Asp Lys Met Arg Glu Met
465                 470                 475                 480
Val Ser Ala Asp Glu Asn Gly Asp Leu Tyr Tyr Glu Ser Ala Asp Tyr
                      485                 490                 495
Ala Pro Asp Ile Ser Asp Tyr Leu Ala Lys Lys Ala Val Gln Ile Ser
                  500                 505                 510
Gly Thr Val Val Asn Gly Lys Val Asp Pro Ile Ala Glu Pro Phe
                  515                 520                 525
```

```
Lys Tyr Glu Pro Asn Thr Leu Ser Met Lys Ser Val Gly Pro Val Gln
            530                 535                 540

Val Gln Thr Leu Pro Glu Val Ser Leu Thr Gly Ala Thr Ile Asn Ser
545                 550                 555                 560

Asn Glu Ile Tyr Leu Gly Lys Gly Gln Glu Ile Gln Ile His Tyr Gln
                565                 570                 575

Val Arg Ile Gln Thr Glu Ser Glu Asn Phe Lys Pro Asp Phe Trp Tyr
            580                 585                 590

Gln Met Asn Gly Arg Thr Thr Gln Pro Leu Ala Thr Ala Pro Glu Lys
        595                 600                 605

Val Asp Phe Gly Val Pro Ser Gly Lys Ala Pro Gly Val Lys Leu Asn
610                 615                 620

Val Lys Lys Ile Trp Glu Glu Tyr Asp Gln Asp Pro Thr Ser Arg Pro
625                 630                 635                 640

Asp Asn Val Ile Tyr Glu Ile Ser Arg Lys Gln Val Thr Asp Thr Ala
                645                 650                 655

Asn Trp Gln Thr Gly Tyr Ile Lys Leu Ser Lys Pro Glu Asn Asp Thr
            660                 665                 670

Ser Asn Ser Trp Glu Arg Lys Asn Val Thr Gln Leu Ser Lys Thr Ala
        675                 680                 685

Asp Glu Ser Tyr Gln Glu Val Leu Gly Leu Pro Gln Tyr Asn Asn Gln
    690                 695                 700

Gly Gln Ala Phe Asn Tyr Gln Thr Thr Arg Glu Leu Ala Val Pro Gly
705                 710                 715                 720

Tyr Ser Gln Glu Lys Ile Asp Asp Thr Thr Trp Lys Asn Thr Lys Gln
                725                 730                 735

Phe Lys Pro Leu Asp Leu Lys Val Ile Lys Asn Ser Ser Ser Gly Glu
            740                 745                 750

Lys Asn Leu Val Gly Ala Val Phe Glu Leu Ser Gly Lys Asn Val Gln
        755                 760                 765

Thr Thr Leu Val Asp Asn Lys Asp Gly Ser Tyr Ser Leu Pro Lys Asp
    770                 775                 780

Val Arg Leu Gln Lys Gly Glu Arg Tyr Thr Leu Thr Glu Val Lys Ala
785                 790                 795                 800

Pro Ala Gly His Glu Leu Gly Lys Lys Thr Thr Trp Gln Ile Glu Val
                805                 810                 815

Ser Glu Gln Gly Lys Val Ser Ile Asp Gly Gln Glu Val Thr Thr Thr
            820                 825                 830

Asn Gln Val Ile Pro Leu Glu Ile Glu Asn Lys Phe Ser Ser Leu Pro
        835                 840                 845

Ile Arg Ile Arg Lys Tyr Thr Met Gln Asn Gly Lys Gln Val Asn Leu
    850                 855                 860

Ala Glu Ala Thr Phe Ala Leu Gln Arg Lys Asn Ala Gln Gly Ser Tyr
865                 870                 875                 880

Gln Thr Val Ala Thr Gln Lys Thr Asp Thr Thr Gly Leu Ser Tyr Phe
                885                 890                 895

Lys Ile Ser Glu Pro Gly Glu Tyr Arg Met Val Glu Gln Ser Gly Pro
            900                 905                 910

Leu Gly Tyr Asp Thr Leu Ala Gly Asn Tyr Glu Phe Thr Val Asp Lys
        915                 920                 925

Tyr Gly Lys Ile His Tyr Ala Gly Lys Asn Ile Glu Glu Asn Ala Pro
    930                 935                 940
```

-continued

```
Glu Trp Thr Leu Thr His Gln Asn Asn Leu Lys Pro Phe Asp Leu Thr
945                 950                 955                 960

Val His Lys Lys Ala Asp Asn Gln Thr Pro Leu Lys Gly Ala Lys Phe
            965                 970                 975

Arg Leu Thr Gly Pro Asp Thr Asp Ile Glu Leu Pro Lys Asp Gly Lys
            980                 985                 990

Glu Thr Asp Thr Phe Val Phe Glu Asn Leu Lys Pro Gly Lys Tyr Val
            995                 1000                1005

Leu Thr  Glu Thr Phe Thr Pro  Glu Gly Tyr Gln Gly  Leu Lys Glu
    1010                1015                 1020

Pro Ile  Glu Leu Ile Ile Arg  Glu Asp Gly Ser Val  Thr Ile Asp
    1025                1030                 1035

Gly Glu  Lys Val Ala Asp Val  Leu Ile Ser Gly Glu  Lys Asn Asn
    1040                1045                 1050

Gln Ile  Thr Leu Asp Val Thr  Asn Gln Ala Lys Val  Pro Leu Pro
    1055                1060                 1065

Glu Thr  Gly Gly Ile Gly Arg  Leu Trp Phe Tyr Leu  Ile Ala Ile
    1070                1075                 1080

Ser Thr  Phe Val Ile Ala Gly  Val Tyr Leu Phe Ile  Arg Arg Pro
    1085                1090                 1095

Glu Gly  Ser Val
    1100

<210> SEQ ID NO 6
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 6
cgcggatcca taacagtaga ggattctgct aaa                                    33

<210> SEQ ID NO 7
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 7
ctagctagct taaccagttt caggtaaagg aacc                                   34

<210> SEQ ID NO 8
<211> LENGTH: 42
<212> TYPE: DNA
<213> ORGANISM: Artificial Sequence
<220> FEATURE:
<223> OTHER INFORMATION: SYNTHESIZED

<400> SEQUENCE: 8
ccggatatct catcatcatc gtacttgata atgaatttga at                          42

<210> SEQ ID NO 9
<211> LENGTH: 39
<212> TYPE: DNA
<213> ORGANISM: Artificial Sequence
<220> FEATURE:
<223> OTHER INFORMATION: SYNTHESIZED

<400> SEQUENCE: 9
```

```
                              -continued ccggatatca ggggttaaaa gaaccaatcg aattaataa                         39

<210> SEQ ID NO 10
<211> LENGTH: 35
<212> TYPE: DNA
<213> ORGANISM: Artificial Sequence
<220> FEATURE:
<223> OTHER INFORMATION: SYNTHESIZED

<400> SEQUENCE: 10
gcgggatcca tgaatggtcg gacaacgttt cagcc                             35

<210> SEQ ID NO 11
<211> LENGTH: 38
<212> TYPE: DNA
<213> ORGANISM: Artificial Sequence
<220> FEATURE:
<223> OTHER INFORMATION: SYNTHESIZED

<400> SEQUENCE: 11
ccgtcgactt acaagcgtcc tatgccacca gtttcagg                          38
```